US010087455B2

(12) United States Patent
Slade et al.

(10) Patent No.: US 10,087,455 B2
(45) Date of Patent: Oct. 2, 2018

(54) WHEAT WITH REDUCED LIPOXYGENASE ACTIVITY

(71) Applicant: Arcadia Biosciences, Inc., Davis, CA (US)

(72) Inventors: Ann Slade, Davis, CA (US); Michelle Noval, Davis, CA (US); Dayna Loeffler, Davis, CA (US); Jessica Mullenberg, Davis, CA (US); Aaron Holm, Davis, CA (US)

(73) Assignee: ARCADIA BIOSCIENCES, INC., Davis, CA (US)

( * ) Notice: Subject to any disclaimer, the term of this patent is extended or adjusted under 35 U.S.C. 154(b) by 0 days.

(21) Appl. No.: 15/185,579

(22) Filed: Jun. 17, 2016

(65) Prior Publication Data

US 2017/0044566 A1 Feb. 16, 2017

Related U.S. Application Data

(60) Provisional application No. 62/182,299, filed on Jun. 19, 2015.

(51) Int. Cl.
*C12N 15/82* (2006.01)
*A01H 5/10* (2018.01)
*A23L 7/10* (2016.01)
*C12N 9/02* (2006.01)

(52) U.S. Cl.
CPC ........... *C12N 15/8247* (2013.01); *A01H 5/10* (2013.01); *A23L 7/10* (2016.08); *A23L 7/198* (2016.08); *C12N 9/0069* (2013.01); *C12N 15/8243* (2013.01); *C12Y 113/11* (2013.01); *C12Y 113/11012* (2013.01); *A23V 2002/00* (2013.01)

(58) Field of Classification Search
None
See application file for complete search history.

(56) References Cited

U.S. PATENT DOCUMENTS

| 6,660,915 B2 | 12/2003 | Douma et al. |
| 6,696,294 B1 | 2/2004 | Konzak |
| 7,897,850 B2 | 3/2011 | Hirota et al. |
| 2003/0167544 A1 | 9/2003 | Douma et al. |
| 2007/0044171 A1 | 2/2007 | Kovalic et al. |
| 2009/0238935 A1 | 9/2009 | Haynes et al. |
| 2013/0276169 A1 | 10/2013 | Poraty et al. |
| 2014/0099421 A1 | 4/2014 | Zhao et al. |
| 2014/0106052 A1* | 4/2014 | Hawley .................. A21D 6/003 426/556 |
| 2014/0130203 A1 | 5/2014 | La Rosa et al. |
| 2015/0004301 A1 | 1/2015 | Arndt et al. |

FOREIGN PATENT DOCUMENTS

| CN | 102925576 A | 2/2012 |
| WO | 02/096190 A2 | 12/2002 |

OTHER PUBLICATIONS

Garbus et al, Journal of Cereal Science, 2009, vol. 50, pp. 67-73 (cited in the IDS filed Oct. 10, 2017) (Year: 2009).*
Carrera et al, Journal of Cereal Science, 2007, vol. 45, pp. 67-77, cited in the IDS filed Oct. 10, 2017 (Year: 2007).*
Leenhardt et al, J. Agric. Food Chem, 2006, vol. 54, pp. 1710-1715, cited in the IDS fileded Oct. 10, 2017 (Year: 2006).*
BLAST results of SEQ ID No. 3, Genbank ADP02185.1, Sep. 7, 2012 (Year: 2012).*
BLAST results of SEQ ID No. 6, GenBank ADR71857.1, Dec. 9, 2010 (Year: 2010).*
Wang et al, Nature Biotechnology, Sep. 2014, vol. 32, No. 9, pp. 947-952 (Year: 2014).*
Xu, B., et al., 2012. Quality Assurance and Safety of Crops & Foods, 4(1), pp. 26-32.
Xu, B., et al. 2013. Journal of Food Engineering, 117(1), pp. 1-7.
Zhang, et al, J. of Stored Products Research 43:87-91, 2007.
Zhang, W., et al., 2008. Theoretical and Applied Genetics, 117(8), pp. 1361-1377.
Zhang, Y.Y., et al., 2012. Journal of Triticeae Crops, 4, p. 005.
International Search Report and Written Opinion of Intl. Appln. No. PCT/US2016/038071, dated Jan. 4, 2017, 17 pages.
Almeida et al, Cereal Chemistry 91(4):321-326, 2014.
Anthon and Barrett, Journal of Agricultural Food Chemistry 49: 32-37, 2001.
Barone, R., 1999. Journal of agricultural and food chemistry, 47(5), pp. 1924-1931.
Borrelli, G.M., 2000. CIHEAM-Options Mediterraneennes, pp. 497-500.
Borelli 1999.Cereal Chem, 76(3), pp. 335-340.
Butt, M.S., Nasir, M. and Akhtar, S., Sharifik. 2004. Int. J. Food Safety, 4, pp. 1-4.
Carrera et al, Journal of Cereal Science 45:67-77, 2007.
Cato, L., Halmos, A.L. and Small, D.M., 2006. Journal of the Science of Food and Agriculture, 86(11), pp. 1670-1678.
De Simone, V., 2010. Journal of Cereal Science, 52(2), pp. 121-128.
Doblado-Maldonado et al, Journal of Cereal Science 56:119-126, 2012.
Doblado Maldonado et al, Food Chemistry 140:204-209, 2013.
Doblado-Maldonado, A.F., 2012. Thesis University of Nebraska—Lincoln.

(Continued)

Primary Examiner — Eileen B O Hara
(74) Attorney, Agent, or Firm — Husch Blackwell LLP

(57) ABSTRACT

A series of independent human-induced non-transgenic mutations found at one or more of the Lpx genes of wheat; wheat plants having these mutations in one or more of their Lpx genes; and a method of creating and finding similar and/or additional mutations of Lpx by screening pooled and/or individual wheat plants. The wheat plants disclosed herein exhibit decreased lipoxygenase activity without having the inclusion of foreign nucleic acids in their genomes. Additionally, products produced from the wheat plants disclosed herein display increased oxidative stability and increased shelf life without having the inclusion of foreign nucleic acids in their genomes.

23 Claims, 7 Drawing Sheets

Specification includes a Sequence Listing.

(56) References Cited

OTHER PUBLICATIONS

Dong, Z., 2015. Molecular breeding, 35(7), p. 150.
Feng et al, Journal of Cereal Science 52:387-394, 2010.
Feng et al, Molecular Breeding 30:113-124, 2012.
Fritsch et al., JAOCS 54:225, 1977.
Galliard, Journal of Cereal Science 4:179-192, 1986.
Galliard, T., 1986. Journal of Cereal Science, 4(1), pp. 33-50.
Galliard, T., 1983. Rancidity in foods/edited by JC Allen and RJ Hamilton.
Garbus et al, Journal of Cereal Science 50:67-73, 2009.
Garbus et al, Journal of Cereal Science 58:298-304, 2013.
Geng et al, Molecular Breeding 28:117-126, 2011.
Geng, H., 2012. Crop Science, 52(2), pp. 568-576.
Goesaert, H., 2005. Trends in food science & technology, 16(1), pp. 12-30.
Goutam, U., 2013. Australian Journal of Crop Science, 7(4), p. 469.
Guo, G., et al., 2014. Theoretical and applied genetics, 127(10), pp. 2095-2103.
Hamilton-Kemp, T.R., et al., 1987. Phytochemistry, 26(5), pp. 1273-1277.
Hessler, T.G., et al., 2002. Crop Science, 42(5), pp. 1695-1700.
Hidalgo, A. and Brandolini, A., 2012. Food chemistry, 131(4), pp. 1499-1503.
Leenhardt, F., et al., 2006. European Journal of Agronomy, 25(2), pp. 170-176.
Leenhardt, F., et al., 2006. Journal of Agricultural and Food Chemistry, 54(5), pp. 1710-1715.
Loiseau, J., et al., 2001. Seed Science Research, 11(3), pp. 199-211.
Manna, F., et al., 1998. Cereal Research Communications, pp. 23-30.
Marathe, S.A., et al., 2002. International journal of food science & technology, 37(2), pp. 163-168.
Narvel et al, American Society of Agronomy 38:926-928, 1998.
Nicolas, J., et al., 1982. Journal of the Science of Food and Agriculture, 33(4), pp. 365-372.
Pico, J., et al., 2015. Food Research International, 75, pp. 200-215.
Sharma, S., et al., 2014. Storage stability and quality assessment of processed cereal brans. Journal of food science and technology, 51(3), pp. 583-588.
Shiiba, K., Negishi, Y., Okada, K. and Nagao, S., 1991. Cereal Chem, 68(2), pp. 115-122.
Shirasawa, K., et al., 2008. Breeding science, 58(2), pp. 169-176.
Surrey Plant Physiology 39: 65-70, (1964).
Suzuki, Y., et al., 1999. Journal of agricultural and food chemistry, 47(3), pp. 1119-1124.
Umate, Plant Signaling & Behavior 6:335-338, 2011.
Verlotta et al, BMC Plant Biology 10:263, 2010.
Wallace, J.M. and Wheeler, E.L., 1972. America Associate of Cereal chemists, pp. 92-98.
Wang, et al., Food Rev. Int., 15(2), 215-234 (1999).
Warwick, M., et al., J. Sci. Food Agric., 1979, 30, 1131-1138.
Warwick, M., et al., J. Sci. Food Agric., 1980, 31, 316-318.
Wu, P., et al., Scientia Agricultura Sinica, 2015, 48(2): 2017-214.
G. Jakab et al., Plant Physiology, Aug. 2003, vol. 132, No. 4, pp. 2230-2239.
International Preliminary Report on Patentability of Intl. Appln. No. PCT/US2016/038071, dated Dec. 19, 2017, 11 pages.
A. Verlotta et al., BMC Plant Biology, 2010, vol. 10, No. 263, 18 pages.
U. Goutam, et al., Australian Journal of Crop Science, 2013, vol. 7, No. 4, pp. 469-483.
NCBI, GenBack accession No. AHG59317.01 (Apr. 1, 2014).
International Search Report of Intl. Appln. No. PCT/US17/37859, dated Nov. 3, 2017, 4 pages.
Written Opinion of Intl. Appln. No. PCT/US17/37859, dated Nov. 3, 2017, 4 pages.

\* cited by examiner

SEQUENCE LISTING

<160> NUMBER OF SEQ ID NOS: 17

<210> SEQ ID NO 1
<211> LENGTH: 3863
<212> TYPE: DNA
<213> ORGANISM: Triticum aestivum

<400> SEQUENCE: 1

| atgatactgg | gcgggctcat | cgacagcctg | accggcgcga | acaagaacgc | acgtctcaag | 60 |
| ggcacggcgg | tgctgatgag | gaagaacgtg | ctggacctca | ccgacttcgg | cgccaccatc | 120 |
| atggacggca | tcggcgactt | cctcggcaag | ggcgtcacct | gccagcttat | cagctccacc | 180 |
| ctcatcgacc | acgtaagca | gtgcacccct | tcctcttcc | tcctcctcct | ctcctctcct | 240 |
| tactagatat | gtcttttaat | ttgtgttgtc | ggccatggat | gcatggatgt | atctcgatcg | 300 |
| gctaaagata | gagatagcct | cggtcggtcg | gtcgtctta | gctgagcatg | gcatgccat | 360 |
| ggaaagaaga | gacaatagta | gcatggtgcg | tgcaccagag | cttgcagagc | atcggatgct | 420 |
| cgagacaaag | caatagaaca | agcaagcaca | cgtcaaaagt | aactatcaca | acctaaacta | 480 |
| aagctttgaa | ctcgactccc | aacaatcaat | caggttgaca | cgtactagta | aactaaagca | 540 |
| catgtgagaa | cgaacgaact | gcgtgcgtgc | gtgcagacaa | cggcgggcgc | gggaaggtgg | 600 |
| gcgcggaggc | ggagctggag | cagtgggtga | cgagcctgcc | gtcgctgacg | acgggggagt | 660 |

```
ccaagttcgg cctcaccttc gactgggagg tggagaagct gggggtgccc ggcgccatcg      720
tcgtcaacaa ctaccacagc tccgagttcc tgctcaagac ggtcaccctc cacgacgtcc      780
ccggccgcgg caacctctcc ttcgtcgcca actcctggat ctaccccgcc gccacctaca      840
cctacagccg cgtcttcttc gccaacgatg tgagttgtga gcctcccttg tttcctctcc      900
tttcctttcc atttcactgc cttcgtcatt catggtcatt aagtcttctt tgagataaga      960
taagattagt aggtgcagaa tttattccgt gttggtagag aaaaaggata tggctaggtg     1020
cagcagaaga ttgaatgaaa ccggcaccgt ggcaccgtgg taggtgaaga aaactgttgc     1080
ccttgcctga ccaagtgtgc gacctgctgc tgccgggtta tttctttgag ataagacacg     1140
tacgtgggct cacatgaacg caagcatggc tccaccacca tgggacgacc tcggtcgcta     1200 catgccgcc tcagaacttt taaaagatgt tgcatgatac ggtagtagca ctcaatccgg     1260
tttactttgc cgaaacggtg acataaaaca catgaaagaa aaagcgatta tactgctcta     1320
gttggcaaag caaaatcatc taattcacgt acttcttttg tcatgagcaa gccatcgatc     1380
ggcttccggc ctgcaggttc agtgctcgtc taaaatgaca aattttcttg ccatgttacg     1440
cgcgtacaga cgtacctgcc gagccagatg ccggcggcgc tgaagccgta ccgcgacgac     1500
gagctccgga acctgcgggg cgacgatcgg caggggccct accaggagca cgaccgcgtc     1560
taccgctacg acgtctacaa cgacctcggc gagggccgcc cggtcctcgg cggcagcgcc     1620 gagcacccctt acccgcggcg cggccgcacg ggccgcaagc caacgccag cgacccgagc     1680 ctggagagcc ggctgtcgct gctggagcag atctacgtgc cgcgggacga gaagttcggc     1740
cacctcaaga cgtccgactt cctgggctac tccatcaagg ccatcacgca gggcatcctg     1800
ccggcggtgc gcacctacgt cgacaccacc ccggcgagt cgactccctt ccaggacatc     1860
atgaacctct acgagggcgg catcaagctg cccatggtgc ccgccctcga ggagctgcgc     1920
aagcagttcc cgctccagct catcaaggac ctgctcccg tgggcggcga ctcgctgctg     1980
aagctccctg tgccacatat catccaggcg gaccagcagg cgtggaggac cgacgaggag     2040
ttcgcgcgcg aggtgctcgc cggcgtcaac ccggtcatga tcacgcgtct cacggtcagt     2100
caacggttac tatgtgtaga atatgtatgt tgtccatggt gagagcacgc aaatcttact     2160
tggtgttggg tcggcatgca tgcaggagtt cccgccaaaa agtagtcttg accctagcaa     2220
gtttggtgac cacaccagca ccatcacggc ggcacacatc cagaagaacc tcagggcct     2280 caccgtgcag caggtaataa tatacacgat cgagttggcc aacccatcgc gatcaactgt     2340
gatttggtgg gagcaggtct aagtaatttt ggcttgttgc atgcaggcgc tggaaagtaa     2400
caggctctac atacttgatc accacgaccg gttcatgccg ttcctgatcg aagtcaacaa     2460
cctgccggcc aacttcatct acgccaccag gaccctcttc ttcctgcgcg cgacggcag     2520 gctcacgccg ctcgccatcg agctgagcga gcccgtcatc ctgggcggcc tcaccaccgc     2580
caagagcaag gtgtacacgc cggtgccgag cggcagcgtc gaaggctggg tgtgggagtt     2640
cgccaaggcc tacgtcgccg tcaacgactc cggctggcac cagctcgtca gccactggta     2700
cgtgcactac ggattaacca acaatggcg acacacccct caaaaagaa aagaaaaca     2760 atggcgacac tgactcggtg tgattcagtc agtcgatgca caactgacct atgattgaaa     2820
cgtgtaggct gaacacccac gcggtgatgg agccgtttgt gatctcgacg aacggcacc     2880 tcagcgtgac gcaccggtg cacaagctgc tgagcccgca ctaccgcgac accatgacca     2940
tcaacgcgct ggcgcggcag acgctcatca acgccggcgg catcttcgag atgacggtgt     3000
```

| | |
|---|---|
| tcccgggcaa gtttgcgctg ggatgtcgt cggtggtgta caaggactgg aagttcaccg | 3060 |
| agcagggcct gcccgacgat ctcatcaaga gggcatggc ggtggaggac ctatcgagcc | 3120 |
| cttacaaggt gcggcttctg gtgtcggact acccgtacgc ggcggacggg ctggcgatct | 3180 |
| ggcacgccat cgagcagtac gtgggcgagt acctggccat ctactacccg gacgacggcg | 3240 |
| tgctgcgggg cgacacggag ctgcaggcgt ggtggaagga ggcgcgcgag gtcgggcacg | 3300 |
| gcgacctcaa ggacgcgccg tggtggccga ggatgcaggg cgtgggggag ctggccaagg | 3360 |
| cgtgcaccac catcatctgg atcgggtcgg cgctgcacgc ggcggtcaac ttcgggcagt | 3420 |
| acccgtacgc ggggttcctc ccgaaccggc cgacggtgag ccggcgccgc atgccggagc | 3480 |
| ccgggacgga cgcgtacgcg gagctggagc gcgacccgga gcgggccttc atccacacca | 3540 |
| tcaccagcca gatccagacc atcatcggca tctcgctgtt ggaggtgctg tccaaacact | 3600 |
| cctctgacga gctctacctg gggcagcgcg acacgccgga gtggacctcg gaccccaagg | 3660 |
| ccctggaggt gttcaagcgg ttcagcgagc ggctggtgga gatcgagagc aaggtggtgg | 3720 |
| gcatgaacca cgacccgcag ctgttgaacc gcaacgcccc ggccaagctc ccctacatgc | 3780 |
| tgctctaccc caacacctcc gaccacaagg gcgccgccgc cggcctcacc gccaagggca | 3840 |
| tccccaacag catctccatc tga | 3863 |

<210> SEQ ID NO 2
<211> LENGTH: 2586
<212> TYPE: DNA
<213> ORGANISM: Triticum aestivum

<400> SEQUENCE: 2

| | |
|---|---|
| atgatactgg gcgggctcat cgacagcctg accggcgcga acaagaacgc acgtctcaag | 60 |
| ggcacgcgg tgctgatgag gaagaacgtg ctggacctca ccgacttcgg cgccaccatc | 120 |
| atggacggca tcggcgactt cctcggcaag ggcgtcacct gccagcttat cagctccacc | 180 |
| ctcatcgacc acgacaacgg cgggcgcggg aaggtgggcg cggaggcgga gctggagcag | 240 |
| tgggtgacga gcctgccgtc gctgacgacg ggggagtcca agttcggcct caccttcgac | 300 |
| tgggaggtgg agaagctggg ggtgcccggc gccatcgtcg tcaacaacta ccacagctcc | 360 |
| gagttcctgc tcaagacggt caccctccac gacgtccccg gccgcggcaa cctctccttc | 420 |
| gtcgccaact cctggatcta ccccgccgcc acctacacct cagccgcgt cttcttcgcc | 480 |
| aacgatacgt acctgccgag ccagatgccg gcggcgctga agccgtaccg cgacgacgag | 540 |
| ctccggaacc tgcggggcga cgatcggcag gggccctacc aggagcacga ccgcgtctac | 600 |
| cgctacgacg tctacaacga cctcggcgag ggccgcccgg tcctcggcgg cagcgccgag | 660 |
| cacccttacc cgcggcgcgg ccgcacgggc cgcaagccca cgccagcga cccgagcctg | 720 |
| gagagccggc tgtcgctgct ggagcagatc tacgtgccgc gggacgagaa gttcggccac | 780 |
| ctcaagacgt ccgacttcct gggctactcc atcaaggcca tcacgcaggg catcctgccg | 840 |
| gcggtgcgca cctacgtcga caccaccccc ggcgagttcg actccttcca ggacatcatg | 900 |
| aacctctacg agggcggcat caagctgccc atggtgcccg cctcgaggga gctgcgcaag | 960 |
| cagttcccgc tccagctcat caaggacctg ctccccgtgg cggcgactc gctgctgaag | 1020 |
| ctccctgtgc cacatatcat ccaggcggac cagcaggcgt ggaggaccga cgaggagttc | 1080 |
| gcgcgcgagg tgctcgccgg cgtcaaccg gtcatgatca cgcgtctcac ggagttcccg | 1140 |
| ccaaaaagta gtcttgaccc tagcaagttt ggtgaccaca ccagcaccat cacggcggca | 1200 |
| cacatccaga agaacctcga gggcctcacc gtgcagcagg cgctggaaag taacaggctc | 1260 |

-continued

```
tacatacttg atcaccacga ccggttcatg ccgttcctga tcgaagtcaa caacctgccc    1320
ggcaacttca tctacgccac caggaccctc ttcttcctgc gcggcgacgg caggctcacg    1380
ccgctcgcca tcgagctgag cgagcccgtc atcctgggcg cctcaccac cgccaagagc     1440 aaggtgtaca cgccggtgcc gagcggcagc gtcgaaggct gggtgtggga gttcgccaag    1500
gcctacgtcg ccgtcaacga ctccggctgg caccagctcg tcagccactg gctgaacacc    1560
cacgcggtga tggagccgtt tgtgatctcg acgaaccggc acctcagcgt gacgcacccg    1620
gtgcacaagc tgctgagccc gcactaccgc gacaccatga ccatcaacgc gctggcgcgg    1680
cagacgctca tcaacgccgg cggcatcttc gagatgacgg tgttcccggg caagtttgcg    1740
ctggggatgt cgtcggtggt gtacaaggac tggaagttca ccgagcaggg cctgcccgac    1800
gatctcatca agaggggcat ggcggtggag gacctatcga gcccttacaa ggtgcggctt    1860
ctggtgtcgg actacccgta cgcggcggac gggctggcga tctggcacgc catcgagcag    1920
tacgtgggcg agtacctggc catctactac ccggacgacg cgtgctgcg gggcgacacg     1980 gagctgcagg cgtggtggaa ggaggcgcgc gaggtcgggc acggcgacct caaggacgcg    2040
ccgtggtggc cgaggatgca gggcgtgggg gagctggcca aggcgtgcac caccatcatc    2100
tggatcgggt cggcgctgca cgcggcggtc aacttcgggc agtacccgta cgcggggttc    2160
ctcccgaacc ggccgacggt gagccggcgc cgcatgccgg agcccgggac ggacgcgtac    2220
gcggagctgg agcgcgaccc ggagcgggcc ttcatccaca ccatcaccag ccagatccag    2280
accatcatcg gcatctcgct gttggaggtg ctgtccaaac actcctctga cgagctctac    2340
ctggggcagc gcgacacgcc ggagtggacc tcggacccca aggccctgga ggtgttcaag    2400
cggttcagcg agcggctggt ggagatcgag agcaaggtgg tgggcatgaa ccacgacccg    2460
cagctgttga accgcaacgg cccggccaag ctcccctaca tgctgctcta ccccaacacc    2520
tccgaccaca agggcgccgc cgccggcctc accgccaagg gcatccccaa cagcatctcc    2580
atctga                                                              2586
```

<210> SEQ ID NO 3
<211> LENGTH: 861
<212> TYPE: PRT
<213> ORGANISM: Triticum aestivum

<400> SEQUENCE: 3

```
Met Ile Leu Gly Gly Leu Ile Asp Ser Leu Thr Gly Ala Asn Lys Asn
1               5                   10                  15

Ala Arg Leu Lys Gly Thr Ala Val Leu Met Arg Lys Asn Val Leu Asp
            20                  25                  30

Leu Thr Asp Phe Gly Ala Thr Ile Met Asp Gly Ile Gly Asp Phe Leu
        35                  40                  45

Gly Lys Gly Val Thr Cys Gln Leu Ile Ser Ser Thr Leu Ile Asp His
    50                  55                  60

Asp Asn Gly Gly Arg Gly Lys Val Gly Ala Glu Ala Glu Leu Glu Gln
65                  70                  75                  80

Trp Val Thr Ser Leu Pro Ser Leu Thr Thr Gly Glu Ser Lys Phe Gly
                85                  90                  95

Leu Thr Phe Asp Trp Glu Val Glu Lys Leu Gly Val Pro Gly Ala Ile
            100                 105                 110

Val Val Asn Asn Tyr His Ser Ser Glu Phe Leu Leu Lys Thr Val Thr
        115                 120                 125
```

Leu His Asp Val Pro Gly Arg Gly Asn Leu Ser Phe Val Ala Asn Ser
130                 135                 140

Trp Ile Tyr Pro Ala Ala Thr Tyr Thr Tyr Ser Arg Val Phe Phe Ala
145                 150                 155                 160

Asn Asp Thr Tyr Leu Pro Ser Gln Met Pro Ala Ala Leu Lys Pro Tyr
                165                 170                 175

Arg Asp Asp Glu Leu Arg Asn Leu Arg Gly Asp Asp Arg Gln Gly Pro
            180                 185                 190

Tyr Gln Glu His Asp Arg Val Tyr Arg Tyr Asp Val Tyr Asn Asp Leu
            195                 200                 205

Gly Glu Gly Arg Pro Val Leu Gly Gly Ser Ala Glu His Pro Tyr Pro
210                 215                 220

Arg Arg Gly Arg Thr Gly Arg Lys Pro Asn Ala Ser Asp Pro Ser Leu
225                 230                 235                 240

Glu Ser Arg Leu Ser Leu Leu Glu Gln Ile Tyr Val Pro Arg Asp Glu
                245                 250                 255

Lys Phe Gly His Leu Lys Thr Ser Asp Phe Leu Gly Tyr Ser Ile Lys
            260                 265                 270

Ala Ile Thr Gln Gly Ile Leu Pro Ala Val Arg Thr Tyr Val Asp Thr
            275                 280                 285

Thr Pro Gly Glu Phe Asp Ser Phe Gln Asp Ile Met Asn Leu Tyr Glu
290                 295                 300

Gly Gly Ile Lys Leu Pro Met Val Pro Ala Leu Glu Glu Leu Arg Lys
305                 310                 315                 320

Gln Phe Pro Leu Gln Leu Ile Lys Asp Leu Leu Pro Val Gly Gly Asp
                325                 330                 335

Ser Leu Leu Lys Leu Pro Val Pro His Ile Ile Gln Ala Asp Gln Gln
            340                 345                 350

Ala Trp Arg Thr Asp Glu Glu Phe Ala Arg Glu Val Leu Ala Gly Val
            355                 360                 365

Asn Pro Val Met Ile Thr Arg Leu Thr Glu Phe Pro Pro Lys Ser Ser
370                 375                 380

Leu Asp Pro Ser Lys Phe Gly Asp His Thr Ser Thr Ile Thr Ala Ala
385                 390                 395                 400

His Ile Gln Lys Asn Leu Glu Gly Leu Thr Val Gln Gln Ala Leu Glu
                405                 410                 415

Ser Asn Arg Leu Tyr Ile Leu Asp His His Asp Arg Phe Met Pro Phe
            420                 425                 430

Leu Ile Glu Val Asn Asn Leu Pro Gly Asn Phe Ile Tyr Ala Thr Arg
            435                 440                 445

Thr Leu Phe Phe Leu Arg Gly Asp Gly Arg Leu Thr Pro Leu Ala Ile
450                 455                 460

Glu Leu Ser Glu Pro Val Ile Leu Gly Gly Leu Thr Thr Ala Lys Ser
465                 470                 475                 480

Lys Val Tyr Thr Pro Val Pro Ser Gly Ser Val Glu Gly Trp Val Trp
                485                 490                 495

Glu Phe Ala Lys Ala Tyr Val Ala Val Asn Asp Ser Gly Trp His Gln
            500                 505                 510

Leu Val Ser His Trp Leu Asn Thr His Ala Val Met Glu Pro Phe Val
            515                 520                 525

Ile Ser Thr Asn Arg His Leu Ser Val Thr His Pro Val His Lys Leu
530                 535                 540

Leu Ser Pro His Tyr Arg Asp Thr Met Thr Ile Asn Ala Leu Ala Arg

```
                         545                 550                 555                 560
Gln Thr Leu Ile Asn Ala Gly Gly Ile Phe Glu Met Thr Val Phe Pro
                    565                 570                 575
Gly Lys Phe Ala Leu Gly Met Ser Ser Val Val Tyr Lys Asp Trp Lys
                580                 585                 590
Phe Thr Glu Gln Gly Leu Pro Asp Asp Leu Ile Lys Arg Gly Met Ala
            595                 600                 605
Val Glu Asp Leu Ser Ser Pro Tyr Lys Val Arg Leu Leu Val Ser Asp
        610                 615                 620
Tyr Pro Tyr Ala Ala Asp Gly Leu Ala Ile Trp His Ala Ile Glu Gln
625                 630                 635                 640
Tyr Val Gly Glu Tyr Leu Ala Ile Tyr Tyr Pro Asp Asp Gly Val Leu
                645                 650                 655
Arg Gly Asp Thr Glu Leu Gln Ala Trp Trp Lys Glu Ala Arg Glu Val
                660                 665                 670
Gly His Gly Asp Leu Lys Asp Ala Pro Trp Trp Pro Arg Met Gln Gly
            675                 680                 685
Val Gly Glu Leu Ala Lys Ala Cys Thr Thr Ile Ile Trp Ile Gly Ser
        690                 695                 700
Ala Leu His Ala Ala Val Asn Phe Gly Gln Tyr Pro Tyr Ala Gly Phe
705                 710                 715                 720
Leu Pro Asn Arg Pro Thr Val Ser Arg Arg Met Pro Glu Pro Gly
                725                 730                 735
Thr Asp Ala Tyr Ala Glu Leu Glu Arg Asp Pro Glu Arg Ala Phe Ile
                740                 745                 750
His Thr Ile Thr Ser Gln Ile Gln Thr Ile Ile Gly Ile Ser Leu Leu
            755                 760                 765
Glu Val Leu Ser Lys His Ser Ser Asp Glu Leu Tyr Leu Gly Gln Arg
        770                 775                 780
Asp Thr Pro Glu Trp Thr Ser Asp Pro Lys Ala Leu Glu Val Phe Lys
785                 790                 795                 800
Arg Phe Ser Glu Arg Leu Val Glu Ile Glu Ser Lys Val Val Gly Met
                805                 810                 815
Asn His Asp Pro Gln Leu Leu Asn Arg Asn Gly Pro Ala Lys Leu Pro
                820                 825                 830
Tyr Met Leu Leu Tyr Pro Asn Thr Ser Asp His Lys Gly Ala Ala Ala
            835                 840                 845
Gly Leu Thr Ala Lys Gly Ile Pro Asn Ser Ile Ser Ile
        850                 855                 860

<210> SEQ ID NO 4
<211> LENGTH: 4263
<212> TYPE: DNA
<213> ORGANISM: Triticum aestivum

<400> SEQUENCE: 4
atgatactgg gcgggctcgt cgacagcctg accggcgcga caagagcgc acggctccag    60 ggcacggtgg tgctcatgag gaagaacgtg ctggacctca cgacttcgg cgccaccatc   120 atggacggca tcggcgagtt catcggcaag ggcgtcacct gccagcttat cagctccacc   180
ctcgtcgacc acgtaagca gtgcaccatt ctcctcttcc tcctcctcct ctccttggta   240
gatatttctt ttgtgttgtc ggccatggat gcatggatgt atctcgatcg gctaaagaat   300
gatagataga tagccatggt cggtcgtctt tagctgagca tgggcatgga agaagagac   360
```

-continued

```
gagagcatgg tgcgtgcacc agagcttaca gagcaccaga tgctccagac aaagcaatag    420
aacaagcaag acacgtcgc caaaagcaac aaacacaacc taaactaaag cacaaagacg    480
tagcgatgaa aaaagcatcg tgggcagatg ctctaaccat gcgagaccgt gctccgtgca    540
gacaacggcg ggcgtgggaa ggtgggcgcg gaggcggagc tggagcagtg ggtgacgagc    600
ctgccgtcgc tgacgacggg ggagtccaag ttcggcctca ccttcgactg ggaggtggag    660
aagctgggcg tgccgggcgc catcatcgtc aacaaccacc acagctccga gttcctgctc    720
aagaccgtca ccctccacga cgtccccggc cgcggcaacc tctccttcgt cgccaactcc    780
tggatctacc ccgttggcag ctacacctac agccgcgtct tcttcgccaa cgatgtgagt    840
tgtgacttgt gagccttgcc tttcctctcc tttcctttttc actggcttcc tcattcatgg    900
tcatttaagt cttctctgag ataagataag attagtaggt gcagaattta ttccatgttg    960
gtagaaaaaa gatatggcta ggtgcagcag aagattgaat gaatgtggca ccgtggttgg    1020
tgaagacaac tgctgcccctt gactgacctg ctgctgggtt cttcctttgg gataagaaca    1080
ccgagcgaga cacgtacgta cgtgagctca acgaaccca tggctccacc tccatgacct    1140
gatccttccc ttgaaacgac ctaagatagt tacatggccg agcccagaac aaactttaa    1200 aaagagatgc tgcatagtca tgatacagtg acataataaa acacatgaaa gaagaggcga    1260
ttattgctct agttggcaaa gcaaaataat ctactaactc ttgtgtagta ctactagcta    1320
gcaacatacg tacgggagtt cttttgtcat aaacaagcga tcgatcggct tcctgcaggt    1380
tcagtgctca tctaaaatga caaatttttt ggtatgtgta cctacgcgca gacgtacctg    1440
ccgagccaga tgccagcggc gctgaagccg taccgcgacg acgagctccg gaacctgcgg    1500
ggcgacgacc ggcagggccc ctaccaggag cacgaccgcg tctaccgcta cgacgtctac    1560
aacgacctcg cgcagggccg ccccgtcctc ggcggcagcg ccgagcaccc ctatccgcgc    1620
cgcggccgca ccgggcgcaa gcccaacgcc aacgacccga gcttggagag ccggctgtcg    1680
ctgctggagc agatctacgt gccgcgggac gagaagttcg ccacctcaa gacgtccgac    1740 ttcctgggct actccatcaa ggccatcacg cagggcatcc tgccggcggt gcgcacctac    1800
gtcgacacca cccccggcga gttcgactcc ttccaggaca tcatcaacct ctacgagggc    1860
ggcatcaagc tgcccaacgt ccccgccctc gaggagctgc gcaagcagtt cccgctccag    1920
ctcatcaagg acctcctccc cgtgggtggc gactcgctgc tcaagctccc cgtccccac    1980 atcatccagg cggaccagca ggcgtggcgg accgacgagg agttctcccg ggaggtcctt    2040
gccggcgtca cccggtcat gatcacgcgt ctcacggtga gtcaacaata attgaacagt    2100
cttactaaag gcccgttcgg aggctctcca ctcctcaact ctctcccgga gcggccggag    2160
cttcagttta aaattatgga gtggccgaag aggtactccg cagatccttg tattctgcgg    2220
agctgggcca gtgccgaaca gggcctaagt ctcagtcgat ctatatccga cagatcttac    2280
attaagattc ttttcagttt ttcttttttct tttttgcat gttatatcaa atttgactaa    2340
gacttcatta aatctcggtc gacagaaact tagccacaca ccataattga acgatgaatg    2400
agtatgctat ccatggatcg agaaccgaga ggtgagagcg tgcctgatct taatttgtgt    2460
tgggtggcat gcatacagga gttcccgcca aaaagtagtc tggaccctag caagtttggt    2520
gaccacacca gcaccgtcac ggcggcgcac atcgagaaaa acctcgaagg cctcaccgtg    2580
cagcaggtaa taatactaca atacacgagt cggccaaccc atcgcgatca actgtgattt    2640
gatggaagca ggtgtaacta attttggcat gttgcaactt gttgcatgca ggcccttgaa    2700
agcaaccggt tgtacatcct tgatcaccac gaccggttca tgccgttcct catcgacgtc    2760
```

```
aacaacctgc ccggcaactt catctacgcc acgaggaccc tcttcttcct gcgcggcgac    2820
ggcaggctca cgccgctcgc catcgagctc agcgagcctg tcatacaggg cggcctcacc    2880
accgccaaga gcaaggtgta cacgccggtg ccgagcggca gcgtcgaagg atgggtgtgg    2940
gagttcgcca aggcctacgt cgccgtcaac gactctgggt ggcaccagct cgtcagccac    3000
tggtacgtgc actacggact aaccaaacaa ctgagaacag tcttactaag tctcagtcga    3060
tctatatccg acactgactc ggtgtgattc agtcagtcga tgcacaactg acctatgatt    3120
gaaacgtgca ggctgaacac tcatgcggtg atggagccgt tgtgatctc gacgaaccgg     3180 cagctcagcg tgacgcaccc ggtgcacaag ctgctgagcc cgcactaccg cgacacgatg    3240
accatcaacg cgctagcgcg gcagacgctc atcaacgccg gcggcatctt cgagatgacg    3300
gtgttcccgg gcaagttcgc gttggggatg tcgtcagtgg tgtacaagga ctggaagttc    3360
acggagcagg gcctgcccga cgatctcatc aagaggtacg taccaagtat aatgtactaa    3420
tgaaactgtg ttacaaatca tgcttttaga tgactgacga cacatacgtg gtgcataaca    3480
aaaaaatgca ggggcatggc ggtggaggac ccgtcgagcc cgtacaaggt gaggctgctg    3540
gtgtctgact acccgtacgc ggcggacggg ctggcgatct ggcacgccat cgagcagtac    3600
gtgagcgagt acctggccat ttactacccg aacgatggcg tggtgcaggg cgacgtggag    3660
ctgcaggcgt ggtggaagga ggtcgcgag gtgggcacg cgacctcaa ggtcgcgcca      3720 tggtggccga ggatgcaagc cgtgggcgag ctggccaagg cgtgcaccac catcatctgg    3780
atcgggtcgg cgctgcatgc ggcggtcaac ttcgggcagt acccatacgc ggggttcctc    3840
ccgaaccggc cgacggtgag ccggcgccgc atgccggagc cggggaccga gcagtacgcg    3900
gagctggagc gcgaccccga gcgggccttc atccacacca tcactagcca gatccagacc    3960
atcatcggca tctcgctgct ggaggtgctg tcgaagcact cctccgacga gctctacctc    4020
gggcagcgtg acacgccgga gtggacctcg gaccccaagg ccctggaggt gttcaagcgg    4080
ttcagcgagc ggctagcgga gatcgagagc aaggtggtgg gcatgaacca cgacccgcag    4140
ctgttgaacc gcaacggtcc ggccaagttc ccctacatgt tgctctaccc caacacctcc    4200
gatcacaagg gcgccgccgc cgggctcacc gctaagggca tccccaacag catctccatc    4260
tga                                                                  4263
```

<210> SEQ ID NO 5
<211> LENGTH: 2586
<212> TYPE: DNA
<213> ORGANISM: Triticum aestivum

<400> SEQUENCE: 5

```
atgatactgg gcgggctcgt cgacagcctg accggcgcga caagagcgc acggctccag      60 ggcacggtgg tgctcatgag gaagaacgtg ctggacctca cgacttcgg cgccaccatc     120 atggacggca tcgcgagtt catcggcaag ggcgtcacct gccagcttat cagctccacc     180
ctcgtcgacc acgacaacgg cgggcgtggg aaggtgggcg cggaggcgga gctggagcag    240
tgggtgacga gcctgccgtc gctgacgacg gggagtcca agttcggcct caccttcgac     300
tgggaggtgg agaagctggg cgtgccggc gccatcatcg tcaacaacca ccacagctcc     360
gagttcctgc tcaagaccgt caccctccac gacgtccccg ccgcggcaa cctctccttc     420 gtcgccaact cctggatcta ccccgttggc agctacacct cagccgcgt cttcttcgcc     480 aacgatacgt acctgccgag ccagatgcca gcggcgctga agccgtaccg cgacgacgag    540
```

```
ctccggaacc tgcggggcga cgaccggcag ggcccctacc aggagcacga ccgcgtctac    600
cgctacgacg tctacaacga cctcggcgag ggccgccccg tcctcggcgg cagcgccgag    660
caccccctatc cgcgccgcgg ccgcaccggg cgcaagccca cgccaacga cccgagcttg    720
gagagccggc tgtcgctgct ggagcagatc tacgtgccgc gggacgagaa gttcggccac    780
ctcaagacgt ccgacttcct gggctactcc atcaaggcca tcacgcaggg catcctgccg    840
gcggtgcgca cctacgtcga caccaccccc ggcgagttcg actccttcca ggacatcatc    900
aacctctacg agggcggcat caagctgccc aacgtccccg ccctcgagga gctgcgcaag    960
cagttcccgc tccagctcat caaggacctc ctccccgtgg gtggcgactc gctgctcaag   1020
ctccccgtcc cccacatcat ccaggcggac cagcaggcgt ggcggaccga cgaggagttc   1080
tcccgggagg tccttgccgg cgtcaacccg gtcatgatca cgcgtctcac ggagttcccg   1140
ccaaaaagta gtctggaccc tagcaagttt ggtgaccaca ccagcaccgt cacggcggcg   1200
cacatcgaga aaaacctcga aggcctcacc gtgcagcagg cccttgaaag caaccggttg   1260
tacatccttg atcaccacga ccggttcatg ccgttcctca tcgacgtcaa caacctgccc   1320
ggcaacttca tctacgccac gaggacccct ttcttcctgc gcggcgacgg caggctcacg   1380
ccgctcgcca tcgagctcag cgagcctgtc atacaggggcg gcctcaccac cgccaagagc   1440
aaggtgtaca cgccggtgcc gagcggcagc gtcgaaggat gggtgtggga gttcgccaag   1500
gcctacgtcg ccgtcaacga ctctgggtgg caccagctcg tcagccactg gctgaacact   1560
catgcggtga tggagccgtt tgtgatctcg acgaaccggc agctcagcgt gacgcacccg   1620
gtgcacaagc tgctgagccc gcactaccgc gacacgatga ccatcaacgc gctagcgcgg   1680
cagacgctca tcaacgccgg cggcatcttc gagatgacgg tgttcccggg caagttcgcg   1740
ttggggatgt cgtcagtggt gtacaaggac tggaagttca cggagcaggg cctgcccgac   1800
gatctcatca agaggggcat ggcggtggag acccgtcga gcccgtacaa ggtgaggctg   1860
ctggtgtctg actacccgta cgcggcggac gggctggcga tctggcacgc catcgagcag   1920
tacgtgagcg agtacctggc catttactac ccgaacgatg gcgtggtgca gggcgacgtg   1980
gagctgcagg cgtggtggaa ggaggtgcgc gaggtgggc acggcgacct caaggtcgcg   2040
ccatggtggc cgaggatgca agccgtgggc gagctggcca aggcgtgcac caccatcatc   2100
tggatcgggt cggcgctgca tgcggcggtc aacttcgggc agtacccata cgcggggttc   2160
ctcccgaacc ggccgacggt gagccggcgc cgcatgccgg agccggggac cgagcagtac   2220
gcggagctgg agcgcgaccc ggagcgggcc ttcatccaca ccatcactag ccagatccag   2280
accatcatcg gcatctcgct gctggaggtg ctgtcgaagc actcctccga cgagctctac   2340
ctcgggcagc gtgacacgcc ggagtggacc tcggaccccca aggccctgga ggtgttcaag   2400
cggttcagcg agcggctagc ggagatcgag agcaaggtgg tgggcatgaa ccacgacccg   2460
cagctgttga accgcaacgg tccggccaag ttccctaca tgttgctcta ccccaacacc   2520
tccgatcaca agggcgccgc cgccgggctc accgctaagg gcatccccaa cagcatctcc   2580
atctga                                                            2586
```

<210> SEQ ID NO 6
<211> LENGTH: 861
<212> TYPE: PRT
<213> ORGANISM: Triticum aestivum

<400> SEQUENCE: 6

Met Ile Leu Gly Gly Leu Val Asp Ser Leu Thr Gly Ala Asn Lys Ser

```
1               5                   10                  15
Ala Arg Leu Gln Gly Thr Val Val Leu Met Arg Lys Asn Val Leu Asp
                20                  25                  30

Leu Asn Asp Phe Gly Ala Thr Ile Met Asp Gly Ile Gly Glu Phe Ile
                35                  40                  45

Gly Lys Gly Val Thr Cys Gln Leu Ile Ser Ser Thr Leu Val Asp His
                50                  55                  60

Asp Asn Gly Gly Arg Gly Lys Val Gly Ala Glu Ala Glu Leu Glu Gln
65                  70                  75                  80

Trp Val Thr Ser Leu Pro Ser Leu Thr Thr Gly Glu Ser Lys Phe Gly
                85                  90                  95

Leu Thr Phe Asp Trp Glu Val Glu Lys Leu Gly Val Pro Gly Ala Ile
                100                 105                 110

Ile Val Asn Asn His His Ser Ser Glu Phe Leu Leu Lys Thr Val Thr
                115                 120                 125

Leu His Asp Val Pro Gly Arg Gly Asn Leu Ser Phe Val Ala Asn Ser
            130                 135                 140

Trp Ile Tyr Pro Val Gly Ser Tyr Thr Tyr Ser Arg Val Phe Phe Ala
145                 150                 155                 160

Asn Asp Thr Tyr Leu Pro Ser Gln Met Pro Ala Ala Leu Lys Pro Tyr
                165                 170                 175

Arg Asp Asp Glu Leu Arg Asn Leu Arg Gly Asp Asp Arg Gln Gly Pro
                180                 185                 190

Tyr Gln Glu His Asp Arg Val Tyr Arg Tyr Asp Val Tyr Asn Asp Leu
                195                 200                 205

Gly Glu Gly Arg Pro Val Leu Gly Gly Ser Ala Glu His Pro Tyr Pro
            210                 215                 220

Arg Arg Gly Arg Thr Gly Arg Lys Pro Asn Ala Asn Asp Pro Ser Leu
225                 230                 235                 240

Glu Ser Arg Leu Ser Leu Leu Glu Gln Ile Tyr Val Pro Arg Asp Glu
                245                 250                 255

Lys Phe Gly His Leu Lys Thr Ser Asp Phe Leu Gly Tyr Ser Ile Lys
                260                 265                 270

Ala Ile Thr Gln Gly Ile Leu Pro Ala Val Arg Thr Tyr Val Asp Thr
            275                 280                 285

Thr Pro Gly Glu Phe Asp Ser Phe Gln Asp Ile Ile Asn Leu Tyr Glu
            290                 295                 300

Gly Gly Ile Lys Leu Pro Asn Val Pro Ala Leu Glu Glu Leu Arg Lys
305                 310                 315                 320

Gln Phe Pro Leu Gln Leu Ile Lys Asp Leu Leu Pro Val Gly Gly Asp
                325                 330                 335

Ser Leu Leu Lys Leu Pro Val Pro His Ile Ile Gln Ala Asp Gln Gln
            340                 345                 350

Ala Trp Arg Thr Asp Glu Glu Phe Ser Arg Glu Val Leu Ala Gly Val
            355                 360                 365

Asn Pro Val Met Ile Thr Arg Leu Thr Glu Phe Pro Pro Lys Ser Ser
            370                 375                 380

Leu Asp Pro Ser Lys Phe Gly Asp His Thr Ser Thr Val Thr Ala Ala
385                 390                 395                 400

His Ile Glu Lys Asn Leu Glu Gly Leu Thr Val Gln Gln Ala Leu Glu
                405                 410                 415

Ser Asn Arg Leu Tyr Ile Leu Asp His His Asp Arg Phe Met Pro Phe
            420                 425                 430
```

```
Leu Ile Asp Val Asn Asn Leu Pro Gly Asn Phe Ile Tyr Ala Thr Arg
        435                 440                 445

Thr Leu Phe Phe Leu Arg Gly Asp Gly Arg Leu Thr Pro Leu Ala Ile
    450                 455                 460

Glu Leu Ser Glu Pro Val Ile Gln Gly Gly Leu Thr Thr Ala Lys Ser
465                 470                 475                 480

Lys Val Tyr Thr Pro Val Pro Ser Gly Ser Val Glu Gly Trp Val Trp
                485                 490                 495

Glu Phe Ala Lys Ala Tyr Val Ala Val Asn Asp Ser Gly Trp His Gln
            500                 505                 510

Leu Val Ser His Trp Leu Asn Thr His Ala Val Met Glu Pro Phe Val
        515                 520                 525

Ile Ser Thr Asn Arg Gln Leu Ser Val Thr His Pro Val His Lys Leu
    530                 535                 540

Leu Ser Pro His Tyr Arg Asp Thr Met Thr Ile Asn Ala Leu Ala Arg
545                 550                 555                 560

Gln Thr Leu Ile Asn Ala Gly Gly Ile Phe Glu Met Thr Val Phe Pro
                565                 570                 575

Gly Lys Phe Ala Leu Gly Met Ser Ser Val Val Tyr Lys Asp Trp Lys
            580                 585                 590

Phe Thr Glu Gln Gly Leu Pro Asp Asp Leu Ile Lys Arg Gly Met Ala
        595                 600                 605

Val Glu Asp Pro Ser Ser Pro Tyr Lys Val Arg Leu Leu Val Ser Asp
    610                 615                 620

Tyr Pro Tyr Ala Ala Asp Gly Leu Ala Ile Trp His Ala Ile Glu Gln
625                 630                 635                 640

Tyr Val Ser Glu Tyr Leu Ala Ile Tyr Tyr Pro Asn Asp Gly Val Val
                645                 650                 655

Gln Gly Asp Val Glu Leu Gln Ala Trp Trp Lys Glu Val Arg Glu Val
            660                 665                 670

Gly His Gly Asp Leu Lys Val Ala Pro Trp Trp Pro Arg Met Gln Ala
        675                 680                 685

Val Gly Glu Leu Ala Lys Ala Cys Thr Thr Ile Ile Trp Ile Gly Ser
    690                 695                 700

Ala Leu His Ala Ala Val Asn Phe Gly Gln Tyr Pro Tyr Ala Gly Phe
705                 710                 715                 720

Leu Pro Asn Arg Pro Thr Val Ser Arg Arg Met Pro Glu Pro Gly
                725                 730                 735

Thr Glu Gln Tyr Ala Glu Leu Glu Arg Asp Pro Glu Arg Ala Phe Ile
            740                 745                 750

His Thr Ile Thr Ser Gln Ile Gln Thr Ile Ile Gly Ile Ser Leu Leu
        755                 760                 765

Glu Val Leu Ser Lys His Ser Ser Asp Glu Leu Tyr Leu Gly Gln Arg
    770                 775                 780

Asp Thr Pro Glu Trp Thr Ser Asp Pro Lys Ala Leu Glu Val Phe Lys
785                 790                 795                 800

Arg Phe Ser Glu Arg Leu Ala Glu Ile Glu Ser Lys Val Val Gly Met
                805                 810                 815

Asn His Asp Pro Gln Leu Leu Asn Arg Asn Gly Pro Ala Lys Phe Pro
            820                 825                 830

Tyr Met Leu Leu Tyr Pro Asn Thr Ser Asp His Lys Gly Ala Ala Ala
        835                 840                 845
```

Gly Leu Thr Ala Lys Gly Ile Pro Asn Ser Ile Ser Ile
    850                 855                 860

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
tggtgagagc acgcaaatct tacttgg                                          27

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
cgtttcaatc ataggtcagt tgtgcatcga                                       30

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
cgcgtacggg tagtccgaca ccagaag                                          27

<210> SEQ ID NO 10
<211> LENGTH: 31
<212> TYPE: DNA
<213> ORGANISM: Artificial Sequence
<220> FEATURE:
<223> OTHER INFORMATION: Primer

<400> SEQUENCE: 10
gcatgccatg gaaagaagag acaatagtag c                                     31

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
tgcgtgctct caccatggac aacatacata                                       30

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
gcaggcgctg gaaagtaaca ggctct                                           26

<210> SEQ ID NO 13
<211> LENGTH: 27
<212> TYPE: DNA

<213> ORGANISM: Artificial Sequence
<220> FEATURE:
<223> OTHER INFORMATION: Primer

<400> SEQUENCE: 13
tggacgagac gaagctccga tgtacca                                     27

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
gaggtgagag cgtgcctgat cttaatttg                                   29

<210> SEQ ID NO 15
<211> LENGTH: 2373
<212> TYPE: DNA
<213> ORGANISM: Triticum aestivum

<400> SEQUENCE: 15
caccgctgta acagccccat tgtctagctc aaagaactct ctcatggcca caattacatc      60
aggaggaagc tgctctttga actttacagc gaaggcatcc agggtggcag tggtgacgtc     120
ctgcccgttc ttgatgatgc ccaggctgcg gccaataaac tgctcagccg cctgtgccgc     180
cggcgtcgtt gctgcgagga cagcagggcg cctgatcctc tgcagggaga ggccacccac     240
cttggagatc ttcacgccag cgagagtttt ccgacgggct gccggcttcc tgggtggtgt     300
tgaagcaggg gaaggaggga gatccggggc agacatcaag agcgcaggct ggcgagcaca     360
gaacagtggt tccgggagag ccaccccag gcttggcaca agcagctcag caagccccgc      420
cggcaacacg tcatcatctg cacgtttacg agcccgtgga gatgtcgggg ttcgctgcag     480
ggggccactg ctgaggacgg tggtgtagg agatgcctca aagccggag gcgtactgg        540 cgagacgtgg aggaggggc tcaacatgga gaccggcgag caaagctcaa tgagtgctgg     600
actcctctct tgaatggcct ctgtagcaac cctagcctca tcacgcttgg agggggtgg      660 tgagcggagc acggacttgg gggagagggg cggcgaagcc ggaggagtgc gggcgtccct     720
tgagtcccgc ctggcactgc ctgggcgcgc gtgcctatac gggctgcgac cacgagcctc     780
caccggagca gccagagcgg tggccggagg ggctcgaccc atctccaggg cgcaagcctc     840
ggggtcgcag actgcgccgg agccgaagag gagagggggcg cgcgccggagc ccaagaggac    900 aggggcggcg gccggcgggg gcggcggcga tgcagcgcgc ctgcggccgt cgcggttgcc     960
gcgatggtca tccctgcttc ccctgtcttg gtcatgccgc tgatcgtcgc gtggcgcacg    1020
ggaaaggctc ctgtggacac gtgcaccgct gtcttgacct cccctggacg cgtcgcgccc    1080
gtcgcggcca cgaccgcggt caccatcttc atctcgatcg cgccgatcct gacgcacggg    1140
acaagagacg cgctcacgcc tgtcgcgagc tttggcctcg ccatccacga tgttgtagcg    1200
ccacgtctcg gtcggcggac tattcacaca accgatgcgt cgccgctctc ggcccgcgtg    1260
catgtatggc gcgccccgcc gctcgcggac gcgtacgttt ggccgccaaa tccaccggac    1320
gcaaagatat atcctcgtcg tagcgacgga aggacgcttg catgtatgga tggagaagcc    1380
ggtgaaacaa aagggaaaac aagatggacg ccgccgtctc gccaatctcg cccacccaca    1440
ctagatcccg gcgctccatg gagacttggg gaagacacgt ccccccaactc tataatgccg    1500 cctccagcgc cgccgtggag gaaccggagt tgcggaagat gtattggaca ctagtgcgcg    1560

```
gccaccaccc ggacgaagcc aaacgaaaac ctaaccctac agctatctac aaacggaatg    1620
catgcaccac tcggccaact attcacacga ccaacgcgtc gccgctctcg gtccgcatgt    1680
atgtatggcg cgccccgccg gtcgccgacg cgtacgtttg accgccaaat gcaccggacg    1740
caaaaatatg tcctcgtcgc agcgacgtgc gcggatgccc catccctgga gctggaccgc    1800
gccatgcgaa agacgagccg ggcgcgtcgc cgtccggcgc tgcgggtagt ccgatccgat    1860
cgagccagcc gctacgcgcc ggcgccgctt gcagcagaaa aggacggggc gatggatcca    1920
tcgcaacaag cgcgggcagg cgccacgcca tccacgtaac agccaggcca agaaaactcg    1980
tgtacgaagc tccgtgctca gcgctgggca cgcgcgcgct ctcgccgcac ccccaccccc    2040
tataaattgg ccggcccgcg ctgcgacctc ctcacacgct ttccctcaca caacacacac    2100
ccatctcctt ccgcacagct ctccaccgaa aggcactggt agtgcagttg aagtagcgac    2160
ggtactgaaa tagcagcaag atgatactgg gcgggctcat cgacagcctg accggcgcga    2220
acaagaacgc acgtctcaag ggcacggcgg tgctgatgag gaagaacgtg ctggacctca    2280
ccgacttcgg cgccaccatc atggacggca tcggcgactt cctcggcaag ggcgtcacct    2340
gccagcttat cagctccacc ctcatcgacc acg                                 2373

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
tcatgccgct gatcgtcgc                                                 19

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
cttgctgcta tttcagtacc g                                              21
```

WHEAT WITH REDUCED LIPOXYGENASE ACTIVITY

CROSS REFERENCE TO RELATED APPLICATIONS

This application claims priority to U.S. Provisional Patent Application No. 62/182,299 filed Jun. 19, 2015, which is incorporated herein by reference in its entirety.

FIELD

In one embodiment, the disclosure relates to mutations in one or more lipoxygenase 1 (Lpx1) genes. In one embodiment, the disclosure relates to human-induced non-transgenic mutations in one or more Lpx1 genes of wheat and wheat plants. In still another embodiment, human-induced non-transgenic mutations are in the Lpx1 genes in the B or D genome.

In one embodiment, the disclosure relates to wheat plants having wheat seeds and wheat flour with increased oxidative stability as a result of non-transgenic mutations in at least one of the Lpx1 genes. In another embodiment, the disclosure relates to a method that utilizes non-transgenic means to create wheat plants having mutations in at least one of their Lpx1 genes. In yet another embodiment, the disclosure relates to wheat flour and wheat-based food and beverage products made from the seeds of these wheat plants having mutations in at least one of their Lpx1 genes.

SUBMISSION OF SEQUENCE LISTING

The contents of the electronic submission of the text file Sequence Listing, which is named ARC-38806.txt, which was created on Sep. 6, 2016, and is 38 KB in size, is incorporated herein by reference in its entirety.

BACKGROUND

Wheat is an important and strategic cereal crop for the majority of the world's populations. It is the most important staple food of about two billion people (36% of the world population). Worldwide, wheat provides nearly 55% of the carbohydrates and 20% of the food calories consumed globally. It exceeds in acreage and production every other grain crop (including rice, maize, etc.) and is therefore, the most important cereal grain crop of the world, which is cultivated over a wide range of climatic conditions. The understanding of genetics and genome organization using molecular markers is of great value for genetic and plant breeding purposes.

The world's main wheat producing regions are China, India, United States, Russian Federation, France, Australia, Germany, Ukraine, Canada, Turkey, Pakistan, Argentina, Kazakhstan and United Kingdom. Most of the currently cultivated wheat varieties belong *Triticum aestivum* L., which is known as common bread wheat and valued for bread making. The greatest portion of the wheat flour produced is used for bread making.

Bread wheat is a hexaploid, with three complete genomes termed A, B and D in the nucleus of each cell. Each of these genomes is almost twice the size of the human genome and consists of around 5,500 million nucleotides. Durum wheat, also known as macaroni wheat or pasta wheat (*Triticum durum* or *Triticum turgidum* subsp. *durum*), is the major tetraploid species of wheat of commercial importance, which is widely cultivated today. Durum wheat has two complete genomes, A and B, and is widely used for making pasta.

Wheat is a widely studied plant, but in some cases, development of new traits is hampered by limited genetic diversity in today's commercial wheat cultivars and also because the bread wheat genome typically has three functionally redundant copies of each gene (called homoeologs), and therefore, single gene alterations usually do not produce any readily visible phenotype such as those that have been found in diploid corn. Often in bread wheat, altered variants of all three homoeologs must be combined genetically in order to evaluate their effects.

Improving the shelf life of whole grain flour is important to meet the increasing food demands of the world population. Whole grain products offer many health advantages such as reducing the risk of chronic diseases such as coronary heart disease, type 2 diabetes, and some types of cancer. Whole grain products can also help improve body weight management and digestive health. Despite these health benefits, greater than 95% of the United States population consume below the recommended daily allowance of whole grains. Consumption of whole grain products are lower due to the bitter and off flavors that develop more rapidly in whole grain flour due to the susceptibility of its lipid fraction to hydrolytic and oxidative rancidity by lipases, lipoxygenases and other enzymes. Improving shelf-life and sensory characteristics of whole grain flour and food products by improving oxidative stability could positively affect consumer acceptance of whole grain products.

Lipoxygenase (Lpx), linoleate: oxygen oxidoreductase; (EC 1.13.11.12) is a class of non-heme iron-containing dioxygenases that catalyse the positional and specific dioxygenation of polyunsaturated fatty acids that contain 1,4-cis, cis pentadiene structures to produce the corresponding hydroperoxides. Lpx are key enzymes catalyzing the oxidation of polyunsaturated fatty acids. Lpxs are non-heme iron-containing dioxygenases, and are monomeric proteins with molecular mass ranging from 94 to 105 kDa in plants. There are many Lpx genes in plant genomes. For example, the *Arabidopsis* genome contains 6 Lpx genes and the rice genome contains 14 Lpx genes. Wheat, which has a genome size 108 times larger than *Arabidopsis* and 36 times larger than rice, has not yet been fully characterized for Lpx genes. At least 3 known wheat Lpx gene families, each with at least one homoeolog on the A, B and D genomes, have been identified to date. Lpx1 and Lpx3 are on chromosome 4 and Lpx2 is on chromosome 5. A quantitative trait locus for lipoxygenase activity has also recently been reported on chromosome 1A in durum wheat.

In plants, products of the lipoxygenase reaction have been shown to have roles in several processes, such as vegetative growth, wounding, response to herbivore and pathogen attack and also mobilization of storage lipids during germination. In rice, double mutants of two different genes, Lox1 and Lox2, but not single mutations in Lox3, improved germination and stability of intact grains for up to 42 months.

In durum wheat, radicals produced during the intermediate states of polyunsaturated fatty acid hydroperoxidation can cause oxidation of carotenoid pigments, and consequently a loss of the yellow flour color preferred for pasta products. Wheat lipoxygenases have been characterized in durum wheat due to efforts to increase yellow carotenoid levels in those varieties. A deletion allele in the durum wheat LpxB1.1 gene (called Lpx-B1.1c) in particular was found associated with improved yellow color in pasta products.

Durum wheat lines with low lipoxygenase activity were also associated with a reduction of Lpx-3 transcript levels in the late stages of grain filling.

In addition to the LpxB1.1 gene, the wheat B genome has an additional copy of the Lpx1 gene that is present either as LpxB1.2 or LpxB1.3. In both durum and bread wheat, the A genome Lpx1 gene is encoded by a pseudogene called LpxA1-like (GenBank FJ518909). Durum wheat does not have the D genome, but an Lpx1 gene in the D genome of bread wheat has also been identified, and the sequence recently deposited in GenBank (KC679302).

In bread wheat, lipases and lipoxygenases play a role in lipid degradation, which can contribute to wheat products with decreased nutritional quality, decreased functional properties and decreased sensory acceptability. Lipoxygenase activity in bread wheat leads to degradation of carotenoids and decreased nutritional value. Since multiple Lpx genes (Lpx1, 2 and 3) are all expressed in the wheat grain each with one or more potential homoeologs in the A, B and D genomes, it is unclear if altering one gene or gene family could positively affect oxidative stability of whole grain flour in bread wheat. Mutations in the lipoxygenase genes in the wheat genome provide a potential pathway for providing increased oxidative stability in wheat flour and products derived therefrom. The disclosure herein demonstrates that novel alleles in the Lpx1 gene significantly improve shelf-life of whole grain flour.

SUMMARY

In one embodiment, the disclosure relates to mutations in one or more lipoxygenase 1 (Lpx1) genes. In one embodiment, the disclosure relates to non-transgenic mutations in one or more Lpx1 genes. In one embodiment, one or more mutations are in the Lpx1 gene of the B genome. In another embodiment, one or more mutations are the Lpx1 gene of the D genome.

In one embodiment, the disclosure relates to multiple non-transgenic mutations in the Lpx gene including but not limited to 1, 2, 3, 4, 5, 6, 7, 8, 9, 10, and greater than 10 mutations.

In one embodiment, the disclosure relates to non-transgenic mutations in the Lpx-B1.2 gene of the B genome including but not limited to 1, 2, 3, 4, 5, 6, 7, 8, 9, 10, and greater than 10 mutations.

In one embodiment, the disclosure relates to non-transgenic mutations in the Lpx-D1 gene of the D genome including but not limited to 1, 2, 3, 4, 5, 6, 7, 8, 9, 10, and greater than 10 mutations.

In another embodiment, the disclosure relates to non-transgenic mutations in the Lpx B1.2 gene of the B genome including but not limited to 1, 2, 3, 4, 5, 6, 7, 8, 9, 10, and non-transgenic mutations in the Lpx-D1 gene of the D genome including but not limited to 1, 2, 3, 4, 5, 6, 7, 8, 9, 10, and greater than 10 mutations.

In another embodiment, the disclosure relates to a wheat plant, wheat seeds, wheat plant parts, and progeny thereof with decreased lipoxygenase activity compared to wild type wheat plant, wheat seeds, wheat plant parts, and progeny thereof.

In another embodiment, the disclosure relates to a wheat plant, wheat seeds, wheat plant parts, and progeny thereof with increased oxidative stability compared to wild type wheat plant, wheat seeds, wheat plant parts, and progeny thereof.

In another embodiment, this invention relates to a wheat plant, wheat seeds, wheat plant parts, and progeny thereof having reduced lipoxygenase activity compared to the wild type wheat plant, wherein the reduction in lipoxygenase activity is caused by a human-induced non-transgenic mutation in one or more of the wheat plant's Lpx1 genes. In another embodiment, the Lpx1 enzyme has reduced activity.

In another embodiment, the disclosure relates to a wheat plant containing one or more mutated Lpx1 genes, as well as seeds, pollen, plant parts and progeny of that plant.

In another embodiment, the disclosure relates to wheat seeds and wheat flour with increased shelf life and improved sensory characteristics having reduced Lpx1 enzyme activity caused by a human-induced non-transgenic mutation in one or more Lpx1 genes.

In another embodiment, the disclosure relates to food, beverage, and food and beverage products incorporating wheat seeds and wheat flour having reduced Lpx1 enzyme activity caused by a human-induced non-transgenic mutation in one or more Lpx1 genes.

In another embodiment, this disclosure relates to a wheat plant having reduced activity of one or more Lpx1 enzymes compared to the wild type wheat plants, created by the steps of obtaining plant material from a parent wheat plant, inducing at least one mutation in at least one copy of an Lpx1 gene of the plant material by treating the plant material with a mutagen to create mutagenized plant material (e.g., seeds or pollen), analyzing progeny wheat plants to detect at least one mutation in at least one copy of an Lpx1 gene, selecting progeny wheat plants that have at least one mutation in at least one copy of an Lpx1 gene, and optionally, crossing progeny wheat plants that have at least one mutation in at least one copy of an Lpx1 gene with other progeny wheat plants that have at least one mutation in a different copy of an Lpx1 gene, and repeating the cycle of identifying progeny wheat plants having mutations and optionally crossing the progeny wheat plants having mutations with other progeny wheat plants having mutations to produce progeny wheat plants with reduced Lpx1 enzyme activity. In another embodiment, the method comprises growing or using the mutagenized plant material to produce progeny wheat plants.

BRIEF DESCRIPTION OF THE SEQUENCE LISTING

The nucleic acid sequences listed in the accompanying sequence listing are shown using standard letter abbreviations for nucleotide bases. Only one strand of each nucleic acid sequence is shown, but the complementary strand is understood to be included by any reference to the displayed strand. In the accompanying sequence listing:

SEQ ID NO: 1 shows a *Triticum aestivum* gene for Lipoxygenase 1, D genome, Lpx-D1 exons 1-6 (3,863 base pairs).

SEQ ID NO: 2 shows the Lpx-D1 coding sequence of SEQ ID NO: 1 (2,586 base pairs).

SEQ ID NO: 3 shows the Lpx-D1 protein sequence of SEQ ID NO. 2 (862 amino acids).

SEQ ID NO: 4 shows a *Triticum aestivum* gene for Lipoxygenase 1, B genome, Lpx-B1.2 exons 1-7 (4,263 base pairs).

SEQ ID NO: 5 shows the Lpx-B1.2 coding sequence of SEQ ID NO. 4 (2,586 base pairs).

SEQ ID NO: 6 shows the Lpx-B1.2 protein sequence of SEQ ID NO. 5 (862 amino acids).

SEQ ID NOs: 7-14 show exemplary homoeolog specific primers that have proven useful in identifying useful mutations within the Lpx-D1 and Lpx-B1.2 gene sequences.

SEQ ID NO: 15 shows the Lpx-D1 promoter sequence and first exon for SEQ ID NO:1 SEQ ID NO: 16-17 show exemplary homoeolog specific primers that have proven useful in identifying useful mutations within the Lpx-D1 promoter.

DETAILED DESCRIPTION

Definitions

Figure 1:
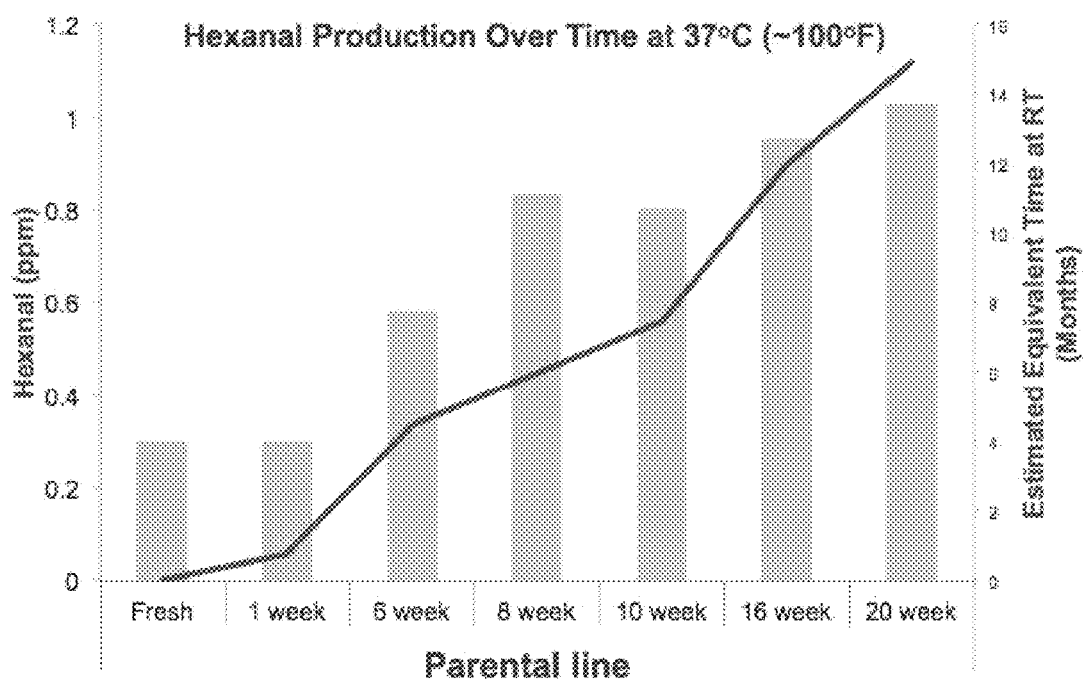
FIG. 1 is a bar graph showing the increase in hexanal production of whole grain flour as an indicator of rancidity during an accelerated aging time course at 37° C.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, the term "allele" is any of one or more alternative forms of a gene, all of which relate to one trait or characteristic. In a diploid cell or organism, the two alleles of a given gene occupy corresponding loci on a pair of homologous chromosomes. An allele can be "wild-type" indicating the parental sequence at a particular nucleotide position, or "mutant" indicating a different nucleotide than the parental sequence. The term "heterozygous" indicates one wild-type and one mutant allele at a particular nucleotide position, and the term "homozygous" indicates two of the same allele at a particular nucleotide position.

As used herein, the terms "altering", "increasing", "increased", "reducing", "reduced", "inhibited" or the like are considered relative terms, i.e. in comparison with the wild-type or unaltered state. The "level of a protein" refers to the amount of a particular protein, for example Lpx, which may be measured by any means known in the art such as, for example, Western blot analysis, or mass spectrometry or other immunological means. The "level of an enzyme activity" refers to the amount of a particular enzyme measured in an enzyme assay. It would be appreciated that the level of activity of an enzyme might be altered in a mutant but not the expression level (amount) of the protein itself. Conversely, the amount of protein might be altered but the activity remain the same if a more or less active protein is produced. Reductions in both amount and activity are also possible such as, for example, when a gene encoding the enzyme is inactivated. In certain embodiments, the reduction in the level of protein or activity is by at least 10% or by at least 20% or by at least 30% or by at least 40% or by at least 50% or by at least 60% compared to the level of protein or activity in the endosperm of unmodified wheat, or by at least 70%, or by at least 80% or by at least 85% or by at least 90% or at least 95%. The reduction in the level of the protein or enzyme activity or gene expression may occur at any stage in the development of the grain, particularly during the grain filling stage, or at all stages of grain development through to maturity.

As used herein, amino acid or nucleotide sequence "identity" and "similarity" are determined from an optimal global alignment between the two sequences being compared. An optimal global alignment is achieved using, for example, the Needleman-Wunsch algorithm (Needleman and Wunsch, 1970, J. Mol. Biol. 48:443-453). Sequences may also be aligned using algorithms known in the art including but not limited to CLUSTAL V algorithm or the BLASTN or BLAST 2 sequence programs.

"Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions. A "conservative" substitution is any substitution that has a positive score in the Blosum62 substitution matrix (Henikoff and Henikoff, 1992, Proc. Natl. Acad. Sci. USA 89: 10915-10919).

By the statement "sequence A is n % similar to sequence B," it is meant that n % of the positions of an optimal global alignment between sequences A and B consists of identical residues or nucleotides and conservative substitutions. By the statement "sequence A is n % identical to sequence B," it is meant that n % of the positions of an optimal global alignment between sequences A and B consists of identical residues or nucleotides.

As used herein, "increase in shelf life" refers to an increase in the time period for which the product can remain sellable or useable. For example, millers commonly stamp 'use by' dates after milling for whole grain flour in the United States. A typical "use by" date may be four months. An "increase in shelf life" would extend the use by date.

As used herein, the term "plant" includes reference to an immature or mature whole plant, including a plant from which seed or grain or anthers have been removed. A seed or embryo that will produce the plant is also considered to be the plant.

As used herein, the term "plant parts" includes plant protoplasts, plant cell tissue cultures from which wheat plants can be regenerated, plant calli, plant clumps, and plant cells that are intact in plants or parts of plants, such as embryos, pollen, ovules, pericarp, seed, flowers, florets, heads, spikes, leaves, roots, root tips, anthers, and the like.

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers, and to longer chains generally referred to as proteins. Polypeptides may contain amino acids other than the 20 gene-encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature and they are well known to those of skill in the art. It will be appreciated that the same type of modification may be present in the same or varying degree at several sites in a given polypeptide.

As used herein, an "Lpx1 derivative" refers to a Lpx1 protein/peptide/polypeptide sequence that possesses biological activity that is substantially reduced as compared to the biological activity of the whole Lpx1 protein/peptide/polypeptide sequence. In other words, it refers to a polypeptide of a modified Lpx1 protein that has reduced Lpx1 enzymatic activity. The term "Lpx1 derivative" encompasses the "fragments" or "chemical derivatives" of a modified Lpx1 protein/peptide.

As used herein, the term "polynucleotide(s)" generally refers to any polyribonucleotide or poly-deoxyribonucleotide, which may be unmodified RNA or DNA or modified RNA or DNA. This definition includes, without limitation, single- and double-stranded DNA, DNA that is a mixture of single- and double-stranded regions or single-, double- and triple-stranded regions, cDNA, single- and double-stranded RNA, and RNA that is a mixture of single- and double-stranded regions, hybrid molecules comprising DNA and RNA that may be single-stranded or, more typically, double-stranded, or triple-stranded regions, or a mixture of single- and double-stranded regions. The term "polynucleotide(s)" also embraces short nucleotides or fragments, often referred to as "oligonucleotides," that due to mutagenesis are not 100% identical but nevertheless code for the same amino acid sequence.

A "reduced or non-functional fragment," as is used herein, refers to a nucleic acid sequence that encodes for a Lpx1 protein that has reduced biological activity as compared the protein coding of the whole nucleic acid sequence. In other words, it refers to a nucleic acid or fragment(s) thereof that substantially retains the capacity of encoding a Lpx1 polypeptide of the invention, but the encoded Lpx1 polypeptide has reduced activity.

The term "fragment," as used herein, refers to a polynucleotide sequence, (e.g, a PCR fragment) which is an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art.

With reference to polynucleotides of the disclosure, the term "isolated polynucleotide" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated polynucleotide" may comprise a PCR fragment. In another embodiment, the "isolated polynucleotide" may comprise a DNA molecule inserted into a vector, such as a plasmid or virus vector, or integrated into the genomic DNA of a prokaryote or eukaryote. An "isolated polynucleotide molecule" may also comprise a cDNA molecule.

A wheat plant is defined herein as any plant of a species of the genus *Triticum*, which species is commercially cultivated, including, for example, *Triticum aestivum* L. ssp. *aestivum* (common or bread wheat), other subspecies of *Triticum aestivum, Triticum turgidum* L. ssp. *durum* (durum wheat, also known as macaroni or hard wheat), *Triticum monococcum* L. ssp. *monococcum* (cultivated einkorn or small spelt), *Triticum timopheevi* ssp. *timopheevi, Triticum turgigum* L. ssp. *dicoccon* (cultivated emmer), and other subspecies of *Triticum turgidum* (Feldman). The wheat may be hexaploid wheat having an AABBDD type genome, or tetraploid wheat having an AABB type genome. Since genetic variation in wheat transferred to certain related species, including rye and barley by hybridization, the disclosure also includes the hybrid species thus formed, including triticale that is a hybrid between bread wheat and rye. In one embodiment, the wheat plant is of the species *Triticum aestivum*, and preferably of the subspecies *aestivum*. Alternatively, since mutations or transgenes can be readily transferred from *Triticum aestivum* to durum wheat, the wheat is preferably *Triticum turgidum* L. ssp. *Durum*.

In one embodiment, the disclosure relates to non-transgenic mutations in one or more Lpx1 genes. In another embodiment, the disclosure describes wheat plants exhibiting seeds with deceased Lpx1 activity as compared to wild type wheat seeds without the inclusion of foreign nucleic acids in the wheat plant genome. In yet another embodiment, the disclosure describes wheat plants exhibiting seeds with increased oxidative stability as compared to wild type wheat seeds, without the inclusion of foreign nucleic acids in the wheat plant genome. In yet another embodiment, the disclosure describes wheat plants exhibiting seeds producing flour with increased shelf life as compared to wild type wheat seeds, without the inclusion of foreign nucleic acids in the wheat plant genome.

In still another embodiment, the disclosure relates to a series of independent human-induced non-transgenic mutations in one or more Lpx1 genes; wheat plants having one or more of these mutations in at least one Lpx1 gene thereof; and a method of creating and identifying similar and/or additional mutations in at least one Lpx1 gene of wheat. Additionally, the disclosure relates to wheat plants exhibiting seed with decreased Lpx1 activity and/or increased oxidative stability and/or shelf life as compared to wild type wheat seed, without the inclusion of foreign nucleic acids in the plants' genomes.

I. Lpx1 Mutations

A. Lpx1 Genes

In one embodiment, the disclosure relates to one or more non-transgenic mutations in the Lpx1 genes including the promoter. In another embodiment, the invention relates to one or more mutations in the Lpx1 gene. In one embodiment, the disclosure relates to multiple non-transgenic mutations in the Lpx1 gene including but not limited to 1, 2, 3, 4, 5, 6, 7, 8, 9, 10, and greater than 10 mutations.

In another embodiment, the Lpx1 gene may contain one or more non-transgenic mutations recited in Tables 1, 2 and 3 and corresponding mutations in homoeologues and combinations thereof.

In another embodiment, the disclosure relates to corresponding mutations to the one or more non-transgenic mutations disclosed herein in the Lpx1 gene in a corresponding homoeologue. By way of example, an identified mutation in the Lpx-D1 gene of the D genome may be a beneficial mutation in the Lpx1 gene of the B and/or A genome. One of ordinary skill in the art will understand that the mutation in the homoeologue may not be in the exact location.

One of ordinary skill in the art understands there is natural variation in the genetic sequences of the Lpx1 genes in different wheat varieties.

The inventors have determined that to achieve a oxidative stability in wheat plants, mutations that reduce Lpx1 gene function are desirable. Preferred mutations include missense and nonsense changes, including mutations that prematurely truncate the translation of one or more Lpx1 proteins from messenger RNA, such as those mutations that create a stop codon within the coding region of an Lpx1 messenger RNA. Such mutations include insertions, deletions, repeat sequences, splice junction mutations, modified open reading frames (ORFs) and point mutations. Some stop codon mutations are more effective than others because not all stop codon mutations reduce lipoxygenase activity to the same extent.

In still another embodiment, one or more mutations are in the Lpx-B1.2 gene of the B genome. In still another embodiment, one or more mutations are in the Lpx-D1 gene of the D genome. In another embodiment, one or more mutations are in the Lpx-B1.2 and Lpx-D1 genes of the B and D genomes.

1. B Genome

In one embodiment, the disclosure relates to multiple non-transgenic mutations in the Lpx gene of the B genome including but not limited to 1, 2, 3, 4, 5, 6, 7, 8, 9, 10, and greater than 10 mutations. In one embodiment, one or more non-transgenic mutations are in both alleles of the Lpx gene in the B genome. In another embodiment, the non-transgenic mutations are identical in both alleles of the Lpx gene of the B genome.

In one embodiment, one or more mutations are in the Lpx-B1.1a gene of the B genome. In one embodiment, the disclosure relates to multiple non-transgenic mutations in the Lpx-B1.1a gene including but not limited to 1, 2, 3, 4, 5, 6, 7, 8, 9, 10, and greater than 10 mutations.

In one embodiment, one or more mutations are in the Lpx-B1.1b gene of the B genome. In one embodiment, the disclosure relates to multiple non-transgenic mutations in the Lpx-B1.1b gene including but not limited to 1, 2, 3, 4, 5, 6, 7, 8, 9, 10, and greater than 10 mutations.

In one embodiment, one or more mutations are in the Lpx-B1.1c gene of the B genome. In one embodiment, the disclosure relates to multiple non-transgenic mutations in the Lpx-B1.1c gene including but not limited to 1, 2, 3, 4, 5, 6, 7, 8, 9, 10, and greater than 10 mutations.

In one embodiment, one or more mutations are in the Lpx-B1.2 gene of the B genome. In one embodiment, the disclosure relates to multiple non-transgenic mutations in the Lpx-B1.2 gene including but not limited to 1, 2, 3, 4, 5, 6, 7, 8, 9, 10, and greater than 10 mutations.

In one embodiment, one or more mutations are in the Lpx-B1.3 gene of the B genome. In one embodiment, the disclosure relates to multiple non-transgenic mutations in the Lpx-B1.3 gene including but not limited to 1, 2, 3, 4, 5, 6, 7, 8, 9, 10, and greater than 10 mutations.

The following mutations identified in Tables 1, 2 and 3 are exemplary of the mutations created and identified according to various embodiments disclosed herein. They are offered by way of illustration, not limitation. It is to be understood that the mutations below are merely exemplary and that similar mutations are also contemplated.

One exemplary mutation in Table 1 is G2982A, resulting in a change from guanine to adenine at nucleotide position 2982 identified according to its position in the sequence of Lpx-B1.2 SEQ ID NO: 4. This mutation results in a change from tryptophan to a stop (*) codon at amino acid position 510 (W510*) identified according to its position in the expressed protein of Lpx-B1.2 (SEQ ID NO: 6).

Table 1 provides examples of mutations created and identified in Lpx-B1.2 in the B genome of wheat plants, variety Express. Nucleotide and amino acid changes are identified according to their positions in SEQ ID NOs: 4 and 6, respectively. Zygosity refers to whether the mutation is heterozygous (Het) or homozygous (Hom) in the M2 plant.

TABLE 1

Representative mutations in the Lpx-B1.2 gene in the B genome

| Primer SEQ IDs | Nucleotide Change (SEQ ID NO: 4) | A.A. Mutation (SEQ ID NO: 6) | PSSM | SIFT | Description | Zygosity |
|---|---|---|---|---|---|---|
| 8, 14 | G2536A | V397I | −12.9 | 1.00 | 1705D03 | Hom |
| 8, 14 | C2563T | L406F | | | 2316C07 | Hom |
| 8, 14 | G2691A | Splice Junction | | | 2171F09 | Hom |
| 8, 14 | C2695T | L415F | | | 2330B06 | Hom |
| 8, 14 | G2722A | D424N | | | 1705E09 | Hom |
| 8, 14 | C2728T | H426Y | | | 2194G09 | Het |
| 8, 14 | C2749T | L433F | | | 2333E09 | Het |
| 8, 14 | C2770T | P440S | | | 1730E05 | Het |
| 8, 14 | C2771T | P440L | | | 2177E04 | Het |
| 8, 14 | C2800T | L450F | 8.1 | 0.06 | 2193D10 | Hom |
| 8, 14 | T2810A | L453Q | 22.4 | 0.00 | 1711F03 | Het |
| 8, 14 | G2816A | G455D | −4.6 | 1.00 | 2178B03 | Hom |
| 8, 14 | G2818A | D456N | 5.1 | 0.26 | 2179F05 | Het |

TABLE 1-continued

Representative mutations in the Lpx-B1.2 gene in the B genome

| Primer SEQ IDs | Nucleotide Change (SEQ ID NO: 4) | A.A. Mutation (SEQ ID NO: 6) | PSSM | SIFT | Description | Zygosity |
|---|---|---|---|---|---|---|
| 8, 14 | G2822A | G457D | 14.6 | 0.02 | 1705F02 | Het |
| 8, 14 | G2825A | R458K | 4.4 | 0.00 | 2171F04 | Hom |
| 8, 14 | C2831T | T460M | −2.1 | 0.04 | 2196D10 | Het |
| 8, 14 | C2833T | P461S | 26.1 | 0.01 | 2169G03 | Het |
| 8, 14 | G2839A | A463T | 20.8 | 0.01 | 2177D04 | Hom |
| 8, 14 | G2854A | E468K | −3.0 | 1.00 | 1743D06 | Het |
| 8, 14 | C2858T | P469L | 28.0 | 0.00 | 2179B06 | Hom |
| 8, 14 | C2879T | T476I |  |  | 2171G11 | Het |
| 8, 14 | C2882T | T477I |  |  | 2328B06 | Hom |
| 8, 14 | G2884A | A478T |  |  | 2196D11 | Het |
| 8, 14 | C2885T | A478V |  |  | 2328E04 | Het |
| 8, 14 | C2903T | T484M |  |  | 1744F11 | Het |
| 8, 14 | G2918A | G489D |  |  | 2322F06 | Hom |
| 8, 14 | G2921A | S490N |  |  | 1706A05 | Hom |
| 8, 14 | G2926A | E492K |  |  | 2330A10 | Het |
| 8, 14 | G2929A | G493R |  |  | 2328A08 | Het |
| 8, 14 | G2933A | W494* |  |  | 1721E07 | Hom |
| 8, 14 | G2941A | E497K | −0.5 | 0.93 | 1712C12 | Het |
| 8, 14 | T2944G | F498V | 5.5 | 0.01 | 1706E05 | Hom |
| 8, 14 | C2948T | A499V | 21.1 | 0.00 | 2178D09 | Hom |
| 8, 14 | G2962A | A504T | 4.1 | 0.56 | 2322E05 | Het |
| 8, 14 | C2963T | A504V | 3.0 | 0.41 | 1705C08 | Het |
| 8, 14 | G2971A | D507N | 8.4 | 0.12 | 2172H04 | Het |
| 8, 14 | C2975T | S508F | −2.9 | 0.82 | 2195C02 | Hom |
| 8, 14 | G2977A | G509R | 12.5 | 0.33 | 1705B01 | Het |
| 8, 14 | G2982A | W510* |  |  | 2175D04 | Het |

In one embodiment, the disclosure relates to a polynucleotide of the Lpx-B1.2 gene in the B genome with one or more non-transgenic mutations listed in Table 1 and corresponding to SEQ ID NO: 4. In another embodiment, the polynucleotide with one or more non-transgenic mutations listed in Table 1 is 85%, 86%, 87%, 88%, 89%, 90%, 91%, 92%, 93%, 94%, 95%, 96%, 97%, 98%, 99% or greater than 99% identical to SEQ ID NO: 4. In yet another embodiment, the polynucleotide with one or more non-transgenic mutations listed in Table 1 is 85%, 86%, 87%, 88%, 89%, 90%, 91%, 92%, 93%, 94%, 95%, 96%, 97%, 98%, 99% or greater than 99% similar to SEQ ID NO: 4.

In still another embodiment, the polynucleotide with one or more non-transgenic mutation listed in Table 1 codes for a Lpx-B1.2 protein, wherein the Lpx-B1.2 protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 6. In still another embodiment, the polynucleotide with one or more non-transgenic mutation listed in Table 1 codes for a Lpx-B1.2 protein, wherein the Lpx-B1.2 protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 6.

2. D Genome

In one embodiment, the disclosure relates to multiple non-transgenic mutations in the Lpx-D1 gene of the D genome including but not limited to 1, 2, 3, 4, 5, 6, 7, 8, 9, 10, and greater than 10 mutations. In one embodiment, one or more non-transgenic mutations are in both alleles of the Lpx-D1 gene in the D genome. In another embodiment, the non-transgenic mutations are identical in both alleles of the Lpx-D1 gene of the D genome.

In one embodiment, one or more mutations are in the Lpx-D1 gene of the D genome. In one embodiment, the disclosure relates to multiple non-transgenic mutations in the Lpx-D1 gene including but not limited to 1, 2, 3, 4, 5, 6, 7, 8, 9, 10, and greater than 10 mutations.

One exemplary mutation in Table 2 is G2629A, resulting in a change from guanine to adenine at nucleotide position 2629 identified according to its position in the sequence of Lpx-D1 SEQ ID NO: 1. This mutation results in a change from tryptophan to a stop (*) codon at amino acid position 494 (W494*) identified according to its position in the expressed Lpx-D1 protein (SEQ ID NO: 3).

Table 2 provides representative examples of mutations created and identified in Lpx-D1 in the D genome of wheat plants, variety Express. Nucleotide and amino acid changes are identified according to their positions in SEQ ID NOs: 1 and 3, respectively. Zygosity refers to whether the mutation is heterozygous (Het) or homozygous (Hom) in the M2 plant.

TABLE 2

Representative mutations in the Lpx-D1 gene in the D genome

| Primer SEQ IDs | Nucleotide Mutation (SEQ ID NO: 1) | A.A. Mutation (SEQ ID NO: 3) | PSSM | SIFT | Description | Zygosity |
|---|---|---|---|---|---|---|
| 10, 11 | G592A | G70E |  |  | 1404C02 | Het |
| 10, 11 | G626A | W81* |  |  | 1686F04 | Hom |

TABLE 2-continued

Representative mutations in the Lpx-D1 gene in the D genome

| Primer SEQ IDs | Nucleotide Mutation (SEQ ID NO: 1) | A.A. Mutation (SEQ ID NO: 3) | PSSM | SIFT | Description | Zygosity |
|---|---|---|---|---|---|---|
| 10, 11 | G627A | V82M | | | 4543C04 | Het |
| 10, 11 | C631T | T83M | | | 2171A08 | Het |
| 10, 11 | G685A | W101* | | | 1686E09 | Hom |
| 10, 11 | G693A | E104K | | | 2316D03 | Het |
| 10, 11 | C709T | P109L | | | 4831G10 | Hom |
| 10, 11 | G712A | G110D | | | 2322A03 | Hom |
| 10, 11 | C742T | S120F | | | 4831B07 | Het |
| 10, 11 | C753T | L124F | | | 4818D09 | Het |
| 10, 11 | C780T | P133S | | | 1685C06 | Hom |
| 10, 11 | C781T | P133L | | | 4547F12 | Het |
| 10, 11 | G789A | G136S | | | 2171A10 | Het |
| 10, 11 | C795T | L138F | | | 2165E05 | Het |
| 10, 11 | C799T | S139F | | | 1745F10 | Hom |
| 10, 11 | C1516T | R185W | | | 1737C05 | Het |
| 10, 11 | C1451T | T163M | 16.4 | 0.01 | 2319H03 | Het |
| 10, 11 | G1588A | G209S | 12.9 | 0.05 | 2176A11 | Hom |
| 10, 11 | C1471T | P170S | 26.2 | 0.00 | 1333E02 | Het |
| 10, 11 | C1472T | P170L | 28.2 | 0.00 | 2195F07 | Het |
| 10, 11 | G1498A | D179N | | | 4831E12 | Het |
| 10, 11 | G1646A | R228H | 22.2 | 0.00 | 4544B07 | Het |
| 10, 11 | G1517A | R185Q | | | 2169E08 | Hom |
| 10, 11 | G1519A | G186S | | | 2164D07 | Hom |
| 10, 11 | G1520A | G186D | | | 2172E07 | Hom |
| 10, 11 | C1531T | Q190* | | | 2172A05 | Hom |
| 10, 11 | G1534A | G191R | | | 2196D06 | Het |
| 10, 11 | C1538T | P192L | | | 2167C03 | Het |
| 10, 11 | G1546A | E195K | | | 2168C11 | Het |
| 10, 11 | G1556A | R198H | 24.0 | 0.00 | 4831D09 | Hom |
| 10, 11 | G1558A | V199I | −2.4 | 1.00 | 1745A09 | Het |
| 10, 11 | C1832T | P290L | 11.4 | 0.25 | 2162B10 | Hom |
| 10, 11 | C1587T | L208= | | | 2165H01 | Hom |
| 10, 11 | G1591A | E210K | 7.9 | 0.15 | 2322B05 | Het |
| 10, 11 | G1966A | G335S | | | 2322B05 | Het |
| 10, 11 | C1600T | P213S | | | 2166H07 | Het |
| 10, 11 | C1601T | P213L | | | 1333G02 | Hom |
| 10, 11 | C1987T | P342S | | | 1402C09 | Het |
| 10, 11 | G1609A | G216S | | | 1334G03 | Hom |
| 10, 11 | G1610A | G216D | | | 1344F01 | Hom |
| 10, 11 | C1633T | P224S | 25.6 | 0.00 | 1333D05 | Hom |
| 10, 11 | G1642A | G227S | 18.2 | 0.49 | 2175A08 | Hom |
| 10, 11 | G1651A | G230S | 13.2 | 0.04 | 2166C06 | Het |
| 10, 11 | C1661T | P233L | 14.7 | 0.06 | 2189H08 | Hom |
| 10, 11 | C1675T | P238S | 13.0 | 0.09 | 1738G07 | Hom |
| 10, 11 | G1679A | S239N | −5.7 | 1.00 | 1344D02 | Het |
| 10, 11 | G1684A | E241K | 12.1 | 0.05 | 2163H01 | Het |
| 10, 11 | G1691A | R243Q | | | 4544B01 | Hom |
| 10, 11 | C1720T | P253S | | | 2191E11 | Hom |
| 10, 11 | C1721T | P253L | | | 4818F12 | Hom |
| 10, 11 | C1723T | R254W | | | 1738B10 | Het |
| 10, 11 | G1724A | R254Q | | | 2171B11 | Het |
| 10, 11 | G1738A | G259S | | | 2324H10 | Het |
| 10, 11 | C1744T | L261F | | | 2335C01 | Het |
| 10, 11 | C1772T | S270F | | | 4543H09 | Hom |
| 10, 11 | G1780A | A273T | | | 2176C11 | Het |
| 10, 11 | G2032A | D357N | 10.5 | 0.17 | 2176C11 | Het |
| 10, 11 | C1805T | A281V | | | 2169B04 | Het |
| 10, 11 | C1814T | T284I | | | 2320B12 | Het |
| 10, 11 | G1819A | V286I | | | 1737E05 | Hom |
| 10, 11 | C1829T | T289I | | | 2322E10 | Hom |
| 10, 11 | C1831T | P290S | 4.9 | 0.83 | 2191F11 | Hom |
| 10, 11 | G1863A | M300I | 4.6 | 0.40 | 2323A10 | Het |
| 10, 11 | G1873A | E304K | 4.5 | 0.34 | 1686D09 | Hom |
| 10, 11 | G1880A | G306D | 13.1 | 0.04 | 1344E07 | Hom |
| 10, 11 | G1909A | E316K | | | 1738D03 | Hom |
| 10, 11 | C1930T | P323S | | | 2320A07 | Hom |
| 10, 11 | A2051T | E363V | 10.1 | 0.50 | 2175E03 | Het |
| 7, 9 | C2279T | L409F | | | 1703B07 | Het |
| 7, 8 | G2386A | Splice Junction | | | 2196A02 | Het |
| 7, 8 | G2397A | S417N | | | 1702D04 | Het |
| 7, 9 | C2414T | L423F | | | 1355F01 | Hom |
| 7, 9 | C2423T | H426Y | | | 1703D03 | Het |
| 7, 8 | G2430A | R428Q | | | 2168H07 | Het |
| 7, 8 | C2438T | P431S | | | 2190C02 | Het |

TABLE 2-continued

Representative mutations in the Lpx-D1 gene in the D genome

| Primer SEQ IDs | Nucleotide Mutation (SEQ ID NO: 1) | A.A. Mutation (SEQ ID NO: 3) | PSSM | SIFT | Description | Zygosity |
|---|---|---|---|---|---|---|
| 7, 8 | G2450A | E435K | | | 1721F01 | Hom |
| 7, 8 | G2453A | V436I | | | 1722C08 | Hom |
| 7, 8 | C2466T | P440L | | | 2169B06 | Hom |
| 7, 9 | G2468A | G441S | | | 1459G11 | Hom |
| 7, 8 | C2487T | T447I | 20.6 | 0.00 | 1729F08 | Het |
| 7, 9 | G2490A | R448K | 24.0 | 0.00 | 1687D06 | Hom |
| 7, 9 | G2508A | R454H | 12.7 | 0.11 | 1457C09 | Hom |
| 7, 8 | C2528T | P461S | 26.1 | 0.01 | 1721E07 | Het |
| 7, 9 | C2529T | P461L | 9.7 | 0.26 | 1456D06 | Het |
| 12, 13 | G2549A | E468K | −3.0 | 1.00 | 2334B03 | Hom |
| 7, 9 | C2553T | P469L | 28.0 | 0.00 | 1705F03 | Het |
| 7, 9 | G2564A | G473S | | | 1743G02 | Het |
| 12, 13 | C3306T | L677F | 11.4 | 0.05 | 4752E11 | Het |
| 12, 13 | C2574T | T476I | | | 2330D08 | Hom |
| 7, 8 | C2577T | T477I | | | 1717E01 | Het |
| 7, 9 | G2591A | V482M | | | 1333B11 | Hom |
| 7, 9 | C2600T | P485S | | | 1686A07 | Hom |
| 12, 13 | C2606T | P487S | | | 2317A11 | Hom |
| 12, 13 | G2610A | S488N | | | 2334D05 | Het |
| 7, 9 | G2613A | G489D | | | 1339F04 | Hom |
| 12, 13 | G2616A | S490N | | | 4776G10 | Het |
| 12, 13 | G2624A | G493S | | | 1748G05 | Het |
| 12, 13 | G2625A | G493D | | | 4752H09 | Het |
| 7, 9 | G2629A | W494* | | | 1416F05 | Het |
| 7, 9 | G2636A | E497K | −0.5 | 0.93 | 1704D07 | Hom |
| 12, 13 | C2658T | A504V | 3.0 | 0.41 | 2335E07 | Hom |
| 7, 9 | G2666A | D507N | 8.4 | 0.12 | 1689A03 | Het |
| 12, 13 | T2675A | W510R | 4.0 | 0.37 | 2317A08 | Hom |
| 12, 13 | G2676A | W510* | | | 2197F06 | Het |
| 12, 13 | G2677A | W510* | | | 1748B07 | Het |
| 7, 9 | C2684T | L513F | 6.1 | 0.12 | 1686B10 | Hom |
| 12, 13 | G2827A | Splice Junction | | | 2319D08 | Hom |
| 12, 13 | G2828A | W517* | | | 2161C05 | Het |
| 12, 13 | G2841A | A522T | 4.2 | 0.24 | 4543C12 | Het |
| 7, 9 | G2849A | M524I | 2.5 | 0.47 | 1339E01 | Het |
| 7, 9 | G2850A | E525K | 18.1 | 0.01 | 1464D10 | Hom |
| 7, 9 | C2853T | P526S | 13.9 | 0.08 | 1705D11 | Het |
| 12, 13 | G2875A | R533Q | 25.7 | 0.00 | 4543C06 | Hom |
| 7, 9 | G2884A | S536N | 17.7 | 0.15 | 1703G05 | Hom |
| 12, 13 | C2895T | P540S | 25.5 | 0.00 | 2316E11 | Hom |
| 7, 9 | G2898A | V541M | 10.6 | 0.02 | 1333A08 | Hom |
| 12, 13 | C2919T | H548Y | 25.9 | 0.00 | 4546A09 | Het |
| 12, 13 | C2932T | T552I | | | 1427B11 | Hom |
| 12, 13 | G3252A | D659N | 27.6 | 0.00 | 4548F10 | Het |
| 12, 13 | A2944T | N556I | | | 2189H07 | Hom |
| 12, 13 | G2946A | A557T | | | 1428A10 | Hom |
| 12, 13 | C2953T | A559V | | | 4551F08 | Hom |
| 12, 13 | C2955T | R560W | | | 1435F06 | Het |
| 7, 9 | G2956A | R560Q | | | 1334G09 | Het |
| 12, 13 | G2993A | M572I | | | 4684G04 | Het |
| 7, 9 | C3003T | P576S | | | 1711C07 | Het |
| 12, 13 | G3022A | G582E | | | 2320E08 | Het |
| 12, 13 | G3049A | W591* | | | 4549G07 | Het |
| 12, 13 | G3060A | E595K | 10.4 | 0.36 | 4546D04 | Hom |
| 12, 13 | C3072T | P599S | 17.1 | 0.03 | 2161B07 | Hom |
| 12, 13 | C3073T | P599L | 11.6 | 0.13 | 1748A11 | Het |
| 12, 13 | G3105A | E610K | | | 2319H09 | Het |
| 12, 13 | G3108A | D611N | | | 4684E07 | Het |
| 12, 13 | G3133A | R619Q | | | 2328H04 | Hom |
| 12, 13 | C3160T | A628V | 19.0 | 0.03 | 4548E09 | Hom |
| 12, 13 | G3162A | A629T | 3.6 | 0.39 | 4544D10 | Hom |
| 12, 13 | G3165A | D630N | 11.7 | 0.06 | 4544C09 | Hom |
| 12, 13 | G3181A | W635* | | | 2189B08 | Het |
| 12, 13 | G3204A | G643S | −4.5 | 0.92 | 1444C10 | Hom |
| 12, 13 | G3207A | E644K | 8.5 | 0.36 | 1402C09 | Het |
| 12, 13 | G3216A | A647T | 3.9 | 0.44 | 4818F10 | Het |
| 12, 13 | C3256T | T660M | 9.0 | 0.22 | 2319B05 | Hom |
| 12, 13 | G3272A | W665* | | | 4544H06 | Hom |
| 12, 13 | G3275A | W666* | | | 1435D10 | Hom |
| 12, 13 | G3282A | A669T | 5.2 | 0.05 | 2330C04 | Hom |
| 12, 13 | G3288A | E671K | 7.7 | 0.45 | 1749D11 | Hom |
| 12, 13 | G3295A | G673E | 22.6 | 0.00 | 1402B04 | Hom |
| 12, 13 | C3297T | H674Y | 15.0 | 0.71 | 1402C07 | Hom |

TABLE 2-continued

Representative mutations in the Lpx-D1 gene in the D genome

| Primer SEQ IDs | Nucleotide Mutation (SEQ ID NO: 1) | A.A. Mutation (SEQ ID NO: 3) | PSSM | SIFT | Description | Zygosity |
|---|---|---|---|---|---|---|
| 12, 13 | C3318T | P681S | 12.8 | 0.71 | 2330B06 | Het |
| 12, 13 | G3345A | G690R | | | 2330B06 | Het |
| 12, 13 | C3319T | P681L | 16.2 | 0.30 | 2161G09 | Hom |
| 12, 13 | G3339A | G688S | | | 4543D12 | Het |
| 12, 13 | G3364A | C696Y | 22.1 | 0.00 | 2194A08 | Hom |
| 12, 13 | C3370T | T698I | 1.8 | 0.34 | 2319D05 | Hom |
| 12, 13 | G3379A | W701* | | | 4543G08 | Hom |
| 12, 13 | G3385A | G703E | 5.9 | 0.01 | 2189D07 | Hom |
| 12, 13 | G3390A | A705T | 14.9 | 0.02 | 2334D08 | Hom |
| 12, 13 | G3399A | A708T | 10.9 | 0.06 | 4544E04 | Het |
| 12, 13 | C3400T | A708V | 19.8 | 0.00 | 2330E08 | Hom |
| 12, 13 | G3415A | G713E | 18.0 | 0.01 | 4547D06 | Het |
| 12, 13 | G3432A | G719R | 14.4 | 0.01 | 2193G12 | Hom |
| 12, 13 | C3438T | L721F | −1.9 | 0.30 | 2197A05 | Hom |
| 12, 13 | C3441T | P722S | 17.4 | 0.01 | 2197D11 | Hom |
| 12, 13 | C3454T | T726M | 13.4 | 0.05 | 1444B07 | Hom |
| 12, 13 | G3456A | V727M | −1.3 | 0.27 | 2334A02 | Hom |
| 12, 13 | C3462T | R729W | 6.1 | 0.08 | 2330A11 | Het |
| 12, 13 | C3481T | P735L | | | 4551G10 | Het |
| 12, 13 | G3483A | G736R | | | 2193F12 | Hom |
| 12, 13 | G3484A | G736E | | | 2320B08 | Hom |
| 12, 13 | G3492A | A739T | | | 1444B06 | Het |
| 12, 13 | G3498A | A741T | | | 1428C06 | Hom |
| 12, 13 | G3501A | E742K | | | 4545B08 | Hom |
| 12, 13 | G3513A | D746N | | | 4551F09 | Het |
| 12, 13 | C3517T | P747L | | | 4549D10 | Het |
| 12, 13 | G3831A | A852T | | | 4831D05 | Hom |
| 12, 13 | G3585A | V770M | 12.7 | 0.00 | 4547H07 | Het |
| 12, 13 | C3601T | S775F | 19.0 | 0.00 | 1427A06 | Hom |
| 12, 13 | C3627T | R784C | | | 4755H09 | Het |
| 12, 13 | G3628A | R784H | | | 4752C09 | Hom |
| 12, 13 | G3643A | W789* | | | 4544B07 | Het |
| 12, 13 | G3644A | W789* | | | 2335D03 | Hom |
| 12, 13 | C3655T | P793L | | | 4548B05 | Hom |
| 12, 13 | G3666A | E797K | | | 2197G10 | Het |

In one embodiment, the disclosure relates to multiple non-transgenic mutations in the Lpx promoter of the D genome including but not limited to 1, 2, 3, 4, 5, 6, 7, 8, 9, 10, and greater than 10 mutations. In one embodiment, one or more non-transgenic mutations are in both alleles of the Lpx-D1 promoter in the D genome. In another embodiment, the non-transgenic mutations are identical in both alleles of the Lpx-D1 promoter of the D genome.

In one embodiment, one or more mutations are in the Lpx-D1 promoter of the D genome. In one embodiment, the disclosure relates to multiple non-transgenic mutations in the Lpx-D1 promoter including but not limited to 1, 2, 3, 4, 5, 6, 7, 8, 9, 10, and greater than 10 mutations.

Table 3 provides representative examples of mutations created and identified in Lpx-D1 promoter in the D genome of wheat plants, variety Express. Nucleotide changes are identified according to their positions in SEQ ID NO: 15. Zygosity refers to whether the mutation is heterozygous (Het) or homozygous (Hom) in the M2 plant.

TABLE 3

Representative mutations in the Lpx-D1 promoter in the D genome

| Primer SEQ IDs | Nucleotide Mutation (SEQ ID NO: 15) | Description | Zygosity |
|---|---|---|---|
| 16, 17 | C1275T | 1687E12 | Het |
| 16, 17 | C1276T | 1706B01 | Hom |
| 16, 17 | C1292T | 1686C07 | Hom |
| 16, 17 | C1292T | 1686C07 | Hom |
| 16, 17 | C1339T | 1705B01 | Het |
| 16, 17 | G1349A | 1686F08 | Het |
| 16, 17 | C1411T | 1687F07 | Het |
| 16, 17 | C1418T | 1685F01 | Hom |
| 16, 17 | G1538A | 1691D07 | Hom |
| 16, 17 | G1546A | 1705A09 | Het |
| 16, 17 | G1602A | 1691F03 | Het |
| 16, 17 | G1736A | 1685E01 | Hom |
| 16, 17 | C1752T | 1705H10 | Hom |
| 16, 17 | C1834T | 1686B02 | Hom |
| 16, 17 | C1857T | 1705H08 | Hom |
| 16, 17 | G1907A | 1684F07 | Hom |
| 16, 17 | G1935A | 1691D05 | Het |
| 16, 17 | C1276T | 1738F01 | Hom |
| 16, 17 | C1282T | 1752H03 | Hom |
| 16, 17 | C1333T | 1743B10 | Hom |
| 16, 17 | G1407A | 2162C07 | Het |
| 16, 17 | G1421A | 1738B02 | Het |
| 16, 17 | G1474A | 2163B03 | Het |
| 16, 17 | C1485T | 1750C09 | Het |
| 16, 17 | C1502T | 2162C05 | Het |
| 16, 17 | G1547A | 2163B05 | Het |
| 16, 17 | G1558A | 1751C10 | Het |

TABLE 3-continued

Representative mutations in the Lpx-D1 promoter in the D genome

| Primer SEQ IDs | Nucleotide Mutation (SEQ ID NO: 15) | Description | Zygosity |
|---|---|---|---|
| 16, 17 | C1625T | 1741D12 | Het |
| 16, 17 | C1627T | 1737B09 | Hom |
| 16, 17 | C1655T | 1737H08 | Het |
| 16, 17 | C1752T | 1737G07 | Hom |
| 16, 17 | C1792T | 1743G08 | Hom |
| 16, 17 | G1795A | 1738E08 | Het |
| 16, 17 | G1839A | 1737G06 | Hom |
| 16, 17 | G1846A | 1741G03 | Het |
| 16, 17 | G1897A | 1741F06 | Het |
| 16, 17 | G1907A | 1750H06 | Het |
| 16, 17 | G1940A | 1741F07 | Het |
| 16, 17 | C2102T | 1752G03 | Het |
| 16, 17 | C1238T | 2164C02 | Het |
| 16, 17 | C1276T | 2168C09 | Het |
| 16, 17 | C1277T | 2168D09 | Het |
| 16, 17 | G1352A | 2171C12 | Het |
| 16, 17 | C1414T | 2169C01 | Het |
| 16, 17 | G1518A | 2171F05 | Hom |
| 16, 17 | G1532A | 2167E08 | Het |
| 16, 17 | C1565T | 2168B09 | Het |
| 16, 17 | G1697A | 2168E07 | Het |
| 16, 17 | C1715T | 2166A12 | Het |
| 16, 17 | C1779T | 2166F08 | Het |
| 16, 17 | C1814T | 2171E05 | Het |
| 16, 17 | G1858A | 2168D11 | Het |
| 16, 17 | G1871A | 2168E03 | Het |
| 16, 17 | C1888T | 2166E01 | Het |
| 16, 17 | G1911A | 2163A08 | Het |
| 16, 17 | G1939A | 2166B08 | Het |
| 16, 17 | G1269A | 2176H02 | Het |
| 16, 17 | G1269A | 2176F08 | Het |
| 16, 17 | G1291A | 2176D11 | Hom |
| 16, 17 | G1297A | 2176G02 | Hom |
| 16, 17 | C1315T, C1569T | 2190B11 | Het |
| 16, 17 | C1484T | 2190C05 | Hom |
| 16, 17 | C1504T | 2189C02 | Het |
| 16, 17 | G1512A | 2172H08 | Het |
| 16, 17 | G1518A | 2171H10 | Het |
| 16, 17 | G1546A | 2176G08 | Hom |
| 16, 17 | C1557T | 2189H06 | Het |
| 16, 17 | C1568T | 2172E03 | Hom |
| 16, 17 | G1634A | 2191E06 | Het |
| 16, 17 | C1695T | 2189B06 | Het |
| 16, 17 | C1709T | 2178B11 | Het |
| 16, 17 | C1715T | 2178E01 | Het |
| 16, 17 | C1725T | 2176C04 | Hom |
| 16, 17 | G1759A | 2175C11 | Het |
| 16, 17 | C1785T | 2175F08 | Het |
| 16, 17 | G1824A | 2190D02 | Het |
| 16, 17 | G1844A | 2189G09 | Het |
| 16, 17 | C1121T | 2196G02 | Het |
| 16, 17 | C1279T | 2196F05 | Het |
| 16, 17 | C1312T | 2196A05 | Hom |
| 16, 17 | G1382A | 2195E02 | Het |
| 16, 17 | C1484T | 2194C07 | Het |
| 16, 17 | C1705T | 2194F11 | Het |
| 16, 17 | G1731A | 2192A08 | Het |
| 16, 17 | G1821A | 2330B06 | Het |
| 16, 17 | G1822A, G1940A | 2195D06 | Het |
| 16, 17 | C1856T | 2319A05 | Het |
| 16, 17 | G1887A | 2195C03 | Hom |
| 16, 17 | G1906A | 2196B02 | Het |
| 16, 17 | C1414T | 4545F03 | Hom |
| 16, 17 | C1483T | 4546E11 | Het |
| 16, 17 | G1526A | 4547G04 | Het |
| 16, 17 | C1831T | 4543C05 | Hom |
| 16, 17 | G1845A | 4544A03 | Hom |
| 16, 17 | G1966A | 4547G09 | Het |

In one embodiment, the invention relates to a polynucleotide of the Lpx1 gene in the D genome with one or more non-transgenic mutations listed in Table 2 and corresponding to SEQ ID NO: 1. In another embodiment, the polynucleotide with one or more non-transgenic mutations listed in Table 2 is 85%, 86%, 87%, 88%, 89%, 90%, 91%, 92%, 93%, 94%, 95%, 96%, 97%, 98%, 99% or greater than 99% identical to SEQ ID NO: 1. In yet another embodiment, the polynucleotide with one or more non-transgenic mutations listed in Table 2 is 85%, 86%, 87%, 88%, 89%, 90%, 91%, 92%, 93%, 94%, 95%, 96%, 97%, 98%, 99% or greater than 99% similar to SEQ ID NO: 1.

In still another embodiment, the polynucleotide with one or more non-transgenic mutation listed in Table 2 codes for a Lpx-D1 protein, wherein the Lpx-D1 protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 3. In still another embodiment, the polynucleotide with one or more non-transgenic mutation listed in Table 2 codes for a Lpx-D1 protein, wherein the Lpx-D1 protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 3.

In still another embodiment, the invention relates to a polynucleotide of the Lpx-D1 promoter in the D genome with one or more non-transgenic mutations listed in Table 3 and corresponding to SEQ ID NO: 15. In another embodiment, the polynucleotide with one or more non-transgenic mutations listed in Table 3 is 85%, 86%, 87%, 88%, 89%, 90%, 91%, 92%, 93%, 94%, 95%, 96%, 97%, 98%, 99% or greater than 99% identical to SEQ ID NO: 15. In yet another embodiment, the polynucleotide with one or more non-transgenic mutations listed in Table 3 is 85%, 86%, 87%, 88%, 89%, 90%, 91%, 92%, 93%, 94%, 95%, 96%, 97%, 98%, 99% or greater than 99% similar to SEQ ID NO: 15.

B. Lpx1 Proteins

In yet another embodiment, the disclosure relates to one or more non-transgenic mutations in the Lpx1 genes (as discussed above in the section entitled Lpx1 Mutations) that result in an Lpx1 protein with one or more mutations as compared to wild type Lpx1 protein. In one embodiment, the non-transgenic mutations include but are not limited to the mutations recited in Tables 1-3, corresponding mutations in homoeologues, and combinations thereof.

In another embodiment, the disclosure relates to one or more non-transgenic mutations in the Lpx1 gene or promoter that inhibits production of the Lpx1 protein. In some embodiments, a mutation in the Lpx1 gene or promoter reduces expression of the Lpx1 protein. In other embodiments, a mutation in the Lpx1 gene or promoter creates an unstable or reduced function Lpx1 protein. In another embodiment, the non-transgenic mutations include but are not limited to the mutations recited in Tables 1-3, corresponding mutations in homoeologues, and combinations thereof.

1. Expression Level of Lpx1 Proteins

In another embodiment, the expression level of Lpx1 proteins with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type Lpx1 protein.

In yet another embodiment, the expression level of Lpx-D1 protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type Lpx-D1 protein.

In still another embodiment, the expression level of Lpx-B1.1a protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type Lpx-B1.1a protein.

In still another embodiment, the expression level of Lpx-B1.1b protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type Lpx-B1.1b protein.

In still another embodiment, the expression level of Lpx-B1.1c protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type Lpx-B1.1c protein.

In still another embodiment, the expression level of Lpx-B1.2 protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type Lpx-B1.2 protein.

In still another embodiment, the expression level of Lpx-B1.3 protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type Lpx-B1.3 protein.

2. Activity of Lpx1 Proteins

In yet another embodiment, the lipoxygenase activity of the Lpx protein with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% of the activity level of the wild type Lpx1 protein. In another embodiment, the Lpx1 protein with one or more mutations disclosed herein has no activity or zero activity as compared to wild type Lpx1 protein.

In yet another embodiment, the lipoxygenase activity of the Lpx1 protein with one or more mutations disclosed herein is from 1-10% or from 10-30% or from 30-50% or from 50-70% or from 70-80% or from 80-90% or from 90-95% of the activity level of the wild type Lpx1 protein.

In yet another embodiment, the lipoxygenase activity of the Lpx1 protein from the Lpx-D1 gene with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% of the activity level of the wild type Lpx-D1 protein. In another embodiment, the Lpx-D1 protein with one or more mutations disclosed herein has no activity or zero activity as compared to wild type Lpx-D1 protein.

In yet another embodiment, the lipoxygenase activity of the Lpx1 protein from the Lpx-D1 gene with one or more mutations disclosed herein is from 1-10% or from 10-30% or from 30-50% or from 50-70% or from 70-80% or from 80-90% or from 90-95% of the activity level of the wild type Lpx-D1 protein.

In yet another embodiment, the lipoxygenase activity of the Lpx1 protein from the Lpx-B1.1a gene with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% of the activity level of the wild type Lpx-B1.1a protein. In another embodiment, the Lpx-B1.1a protein with one or more mutations disclosed herein has no activity or zero activity as compared to wild type Lpx-B1.1a protein.

In yet another embodiment, the lipoxygenase activity of the Lpx1 protein from the Lpx-B1.1a gene with one or more mutations disclosed herein is from 1-10% or from 10-30% or from 30-50% or from 50-70% or from 70-80% or from 80-90% or from 90-95% of the activity level of the wild type Lpx-B1.1a protein.

In yet another embodiment, the lipoxygenase activity of the Lpx1 protein from the Lpx-B1.1b gene with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% of the activity level of the wild type Lpx1 protein. In another embodiment, the Lpx-B1.1b protein with one or more mutations disclosed herein has no activity or zero activity as compared to wild type Lpx-B1.1b protein.

In yet another embodiment, the lipoxygenase activity of the Lpx1 protein from the Lpx-B1.1b gene with one or more mutations disclosed herein is from 1-10% or from 10-30% or from 30-50% or from 50-70% or from 70-80% or from 80-90% or from 90-95% of the activity level of the wild type Lpx-B1.1b protein.

In yet another embodiment, the lipoxygenase activity of the Lpx1 protein from the Lpx-B1.1c gene with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% of the activity level of the wild type Lpx-B1.1c protein.

In yet another embodiment, the lipoxygenase activity of the Lpx1 protein from the Lpx-B1.1c gene with one or more mutations disclosed herein is from 1-10% or from 10-30% or from 30-50% or from 50-70% or from 70-80% or from 80-90% or from 90-95% of the activity level of the wild type Lpx-B1.1c protein.

In yet another embodiment, the lipoxygenase activity of the Lpx1 protein from the Lpx-B1.2 gene with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% of the activity level of the wild type Lpx-B1.2 protein.

In yet another embodiment, the lipoxygenase activity of the Lpx1 protein from the Lpx-B1.2 gene with one or more mutations disclosed herein is from 1-10% or from 10-30% or from 30-50% or from 50-70% or from 70-80% or from 80-90% or from 90-95% of the activity level of the wild type Lpx-B1.2 protein.

In yet another embodiment, the lipoxygenase activity of the Lpx1 protein from the Lpx-B1.3 gene with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% of the activity level of the wild type Lpx-B1.3 protein.

In yet another embodiment, the lipoxygenase activity of the Lpx1 protein produced from the Lpx-B1.3 gene with one or more mutations disclosed herein is from 1-10% or from 10-30% or from 30-50% or from 50-70% or from 70-80% or from 80-90% or from 90-95% of the activity level of the wild type Lpx-B1.3 protein.

C. Oxidative Stability/Increased Shelf Life

In yet another embodiment, the disclosure relates to one or more non-transgenic mutations in an Lpx1 gene (as discussed above in the section entitled Lpx1 Mutations) that results in increased shelf life.

In yet another embodiment, the disclosure relates to one or more non-transgenic mutations in an Lpx1 gene (as discussed above in the section entitled Lpx1 Mutations) that results in increased oxidative stability of flour made from wheat grains with one or more Lpx1 mutations as compared to wild type wheat grains. In one embodiment, the non-transgenic mutations include but are not limited to the mutations recited in Tables 1-3, corresponding mutations in homoeologues, and combinations thereof.

In yet another embodiment, the shelf life of whole grain flour made from wheat grains with one or more Lpx1 mutations disclosed herein is increased from the typical shelf life of whole grain flour. Millers commonly stamp 'use by' dates of 3-9 months after milling for whole grain flour in the United States, but this shelf life can be reduced to 1-3 months by high storage temperatures and humidity. Shelf life can be determined by sensory characteristics of the flour and products made from it including color, flavor, texture, aroma, performance or overall preference of the finished product. Trained panelists can be used to assess differences between materials.

In yet another embodiment, shelf life of whole grain flour made from wheat grain with one or more mutations disclosed herein is increased by 1-9 months, or 2-10 months, or 3-11 months, or 4-12 months, or 5-13 months, or 6-14 months, or 7-15 months, or 8-16 months, or 9-17 months, or 10-18 months or 11-19 months, or 12-20 months, or 13-21 months, or 14-22 months, or 15-23 or 16-24 months as compared to the shelf life of whole grain flour made from wild-type grain.

In yet another embodiment, shelf life of whole grain flour made from wheat grain with one or more mutations disclosed herein is increased by 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, or greater than 30 months as compared to the shelf life of whole grain flour made from wild-type grain.

In yet another embodiment, the oxidative stability of whole grain flour made from wheat grain with one or more mutations disclosed herein is increased due to the decreased production of the decomposition products of fatty acids that can affect the smell or flavor of the product. Not to be bound by any particular theory, the oxidative stability of whole grain flour made from wheat grain with one or more mutations disclosed herein is increased due to the decreased production of the decomposition products of fatty acids.

In yet another embodiment, the production of decomposition products of fatty acids, including but not limited to hexanal, or nonenal, or trihydroxydecanoic acid, among others is decreased in whole grain flour made from wheat grain with one or more mutations disclosed herein.

In still another embodiment, the production of decomposition products of fatty acids, including but not limited to hexanal, or nonenal, or trihydroxydecanoic acid, is decreased in whole grain flour made from wheat grain with one or more mutations disclosed herein by 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% as compared to the production of degradation products of fatty acids in whole grain flour made from the wild-type grain.

In another embodiment, the production of decomposition products of fatty acids, including but not limited to hexanal, or nonenal, or trihydroxydecanoic acid, is decreased in whole grain flour made from wheat grain with one or more mutations disclosed herein from 1% to 5%, or from 5% to 10%, or from 10% to 15%, or from 15% to 20%, or from 20% to 25%, or from 25% to 30%, or from 30% to 35%, or from 35% to 40%, or from 40% to 45%, or from 45% to 50%, or from 50% to 55%, or from 55% to 60%, or from 65% to 70%, or from 70% to 75%, or from 75% to 80%, or from 80% to 85%, or from 85% to 90%, or from 90% to 95%, or from 95% to 99%, or by more than 99% as compared to the production of degradation products of fatty acids in whole grain flour made from the wild-type grain.

In another embodiment, the production of decomposition products of fatty acids, including but not limited to hexanal, or nonenal, or trihydroxydecanoic acid, is decreased in whole grain flour made from wheat grain with one or more mutations disclosed herein by at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95% as compared to the production of degradation products of fatty acids in whole grain flour made from the wild-type grain.

In another embodiment, the production of trihydroxydecanoic acid (pinellic acid) is decreased in whole grain flour or dough or bread or other products made from wheat grain with one or more mutations disclosed herein from 1% to 5%, or from 5% to 10%, or from 10% to 15%, or from 15% to 20%, or from 20% to 25%, or from 25% to 30%, or from 30% to 35%, or from 35% to 40%, or from 40% to 45%, or from 45% to 50%, or from 50% to 55%, or from 55% to 60%, or from 65% to 70%, or from 70% to 75%, or from 75% to 80%, or from 80% to 85%, or from 85% to 90%, or from 90% to 95%, or from 95% to 99%, or by more than 99% as compared to the production of pinellic acid in whole grain flour made from the wild-type grain.

In another embodiment, the production of trihydroxydecanoic acid (pinellic acid) is decreased in whole grain flour or dough or bread or other products made from wheat grain with one or more mutations disclosed herein by at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95% as compared to the production of pinellic acid in whole grain flour made from the wild-type grain.

III. Transgenes

In one embodiment, the disclosure relates to a transgenic plant that comprises a transgene that encodes a polynucleotide, which down-regulates the expression of the Lpx1 gene and/or the activity of the Lpx1 protein. Examples of such polynucleotides include, but are not limited to, antisense polynucleotide, a sense polynucleotide, a catalytic polynucleotide, an artificial microRNA or a duplex RNA molecule.

In one embodiment, the disclosure relates to a wheat plant comprising a transgene that reduces the expression of the Lpx1 gene and/or activity of the Lpx1 protein, wherein grain from the wheat plant has increased oxidative stability or increased shelf-life as compared to grains from a wild type plant.

A. Antisense Polynucleotides

The term "antisense polynucleotide" shall be taken to refer to a DNA or RNA, or combination thereof, molecule that is complementary to at least a portion of a specific mRNA molecule encoding Lpx1 and capable of interfering with a post-transcriptional event such as mRNA translation.

An antisense polynucleotide in a plant will hybridize to a target polynucleotide under physiological conditions. As used herein, the term "an antisense polynucleotide which hybridizes under physiological conditions" means that the polynucleotide (which is fully or partially single stranded) is at least capable of forming a double stranded polynucleotide with mRNA encoding a protein.

Antisense molecules may include sequences that correspond to the structural gene or for sequences that effect control over the gene expression or splicing event. For example, the antisense sequence may correspond to the targeted coding region of Lpx1 or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences, which may function to stabilize the molecule.

B. Catalytic Polynucleotides

The term catalytic polynucleotide/nucleic acid refers to a DNA molecule or DNA-containing molecule (also known in the art as a "deoxyribozyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain").

The ribozymes in plants disclosed herein and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase.

As with antisense polynucleotides described herein, the catalytic polynucleotides should also be capable of hybridizing a target nucleic acid molecule (for example mRNA encoding LPX1) under "physiological conditions," namely those conditions within a plant cell.

C. RNA Interference

RNA interference (RNAi) is particularly useful for specifically inhibiting the production of a particular protein. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering, WO 99/32619, WO 99/53050, WO 99/49029, and WO 01/34815.

In one example, a DNA is introduced that directs the synthesis of an at least partly double stranded (duplex) RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridize should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

In one embodiment, small interfering RNA ("siRNA") molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the barley plant in which it is to be introduced, e.g., as determined by standard BLAST search.

D. microRNA

MicroRNA regulation is a clearly specialized branch of the RNA silencing pathway that evolved towards gene regulation, diverging from conventional RNAi/Post transcriptional Gene Silencing (PTGS). MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression.

E. Co-suppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for the antisense sequences described above. In some instances the additional copy of the gene sequence interferes with the expression of the target plant gene. Reference is made to WO 97/20936 and EP 0465572 for methods of implementing co-suppression approaches.

IV. Genomic Editing

In one embodiment, the disclosure relates to a plant with reduced expression of the Lpx1 gene and/or reduced activity of the Lpx1 protein, wherein reduced expression of the Lpx1 gene and/or reduced activity of the Lpx1 protein is achieved by genomic editing.

In one embodiment, the disclosure relates to a wheat plant with a genomically edited Lpx1 gene, wherein grain from the wheat plant has increase oxidative stability or increased shelf life as compared to grains from a wild type plant.

Genome editing, or genome editing with engineered nucleases (GEEN), is a type of genetic engineering in which DNA is inserted, replaced, or removed from a genome using artificially engineered nucleases, or "molecular scissors." The nucleases create specific double-stranded breaks (DSBs) at desired locations in the genome, and harness the cell's endogenous mechanisms to repair the induced break by natural processes of homologous recombination (HR) and nonhomologous end-joining (NHEJ). There are currently four main families of engineered nucleases being used: Zinc finger nucleases (ZFNs), Transcription Activator-Like Effector Nucleases (TALENs), the CRISPR/Cas system, and engineered meganuclease with a re-engineered homing endonucleases.

A. Zinc Finger Nucleases (ZFNs)

Zinc-finger nucleases (ZFNs) are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms.

ZFNs consist of an engineered zinc finger DNA-binding domain fused to the cleavage domain of the FoId restriction endonuclease. ZFNs can be used to induce double-stranded breaks (DSBs) in specific DNA sequences and thereby promote site-specific homologous recombination with an exogenous template. The exogenous template contains the sequence that is to be introduced into the genome.

Publicly available methods for engineering zinc finger domains include: (1) Context-dependent Assembly (CoDA), (2) Oligomerized Pool Engineering (OPEN), and (3) Modular Assembly.

In one embodiment, the disclosure relates to reducing expression of the Lpx1 gene and/or reducing activity of the Lpx1 protein using ZFNs.

B. Transcription Activator-Like Effector Nucleases (TALENs)

TALEN is a sequence-specific endonuclease that consists of a transcription activator-like effector (TALE) and a FokI endonuclease. TALE is a DNA-binding protein that has a highly conserved central region with tandem repeat units of 34 amino acids. The base preference for each repeat unit is determined by two amino acid residues called the repeat-variable di-residue (RVD), which recognizes one specific nucleotide in the target DNA. Arrays of DNA-binding repeat units can be customized for targeting specific DNA sequences. As with ZFNs, dimerization of two TALENs on targeted specific sequences in a genome results in FokI-dependent introduction of DSBs, stimulating homology directed repair (HDR) and Non-homologous end joining (NHEJ) repair mechanisms.

In one embodiment, the disclosure relates to reducing expression of the Lpx1 gene and/or reducing activity of the Lpx1 protein using TALENs.

C. CRISPR/Cas System

The Clustered Regularly Interspaced Short Palindromic Repeats (CRISPR) Type II system is an RNA-Guided Endonuclease technology for genome engineering. There are two distinct components to this system: (1) a guide RNA and (2) an endonuclease, in this case the CRISPR associated (Cas) nuclease, Cas9.

The guide RNA is a combination of the endogenous bacterial crRNA and tracrRNA into a single chimeric guide RNA (gRNA) transcript. The gRNA combines the targeting specificity of the crRNA with the scaffolding properties of the tracrRNA into a single transcript. When the gRNA and the Cas9 are expressed in the cell, the genomic target sequence can be modified or permanently disrupted.

The gRNA/Cas9 complex is recruited to the target sequence by the base-pairing between the gRNA sequence and the complementarity to the target sequence in the genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the wild-type Cas9 can cut both strands of DNA causing a Double Strand Break (DSB). Cas9 will cut 34 nucleotides upstream of the PAM sequence. A DSB can be repaired through one of two general repair pathways: (1) NHEJ DNA repair pathway or (2) the HDR pathway. The NHEJ repair pathway often results in insertions/deletions (InDels) at the DSB site that can lead to frameshifts and/or premature stop codons, effectively disrupting the open reading frame (ORF) of the targeted gene.

The HDR pathway requires the presence of a repair template, which is used to fix the DSB. HDR faithfully copies the sequence of the repair template to the cut target sequence. Specific nucleotide changes can be introduced into a targeted gene by the use of HDR with a repair template.

In one embodiment, the disclosure relates to reducing expression of the Lpx1 gene and/or reducing activity of the Lpx1 protein using the CRISPR/cas9 system.

D. Meganuclease with Re-Engineered Homing Nuclease

Meganucleases are endodeoxyribonucleases characterized by a large recognition site (double-stranded DNA sequences of 12 to 40 base pairs); as a result this site generally occurs only once in any given genome. For example, the 18-base pair sequence recognized by the I-SceI meganuclease would on average require a genome twenty times the size of the human genome to be found once by chance (although sequences with a single mismatch occur about three times per human-sized genome). Meganucleases are therefore considered to be the most specific naturally occurring restriction enzymes.

Among meganucleases, the LAGLIDADG family of homing endonucleases has become a valuable tool for the study of genomes and genome engineering over the past fifteen years. By modifying their recognition sequence through protein engineering, the targeted sequence can be changed.

In one embodiment, the disclosure relates to reducing expression of the Lpx1 gene and/or reducing activity of the Lpx1 protein using a meganuclease with a re-engineered homing nuclease.

V. Wheat Cultivars

In one embodiment, a wheat cultivar having at least one Lpx gene that is diploid, tetraploid, or hexaploid may be used. In another embodiment, the wheat is *Triticum aestivum*.

In one embodiment, any cultivar of wheat can be used to create mutations in an Lpx gene. In one embodiment, any cultivar of wheat can be used to create mutations in an Lpx-D1 gene. In another embodiment, any cultivar of wheat can be used to create mutations in an Lpx-B1.1a gene. In another embodiment, any cultivar of wheat can be used to create mutations in an Lpx-B1.1b gene. In another embodiment, any cultivar of wheat can be used to create mutations in an Lpx-B1.1c gene. In another embodiment, any cultivar of wheat can be used to create mutations in an Lpx-B1.2 gene. In another embodiment, any cultivar of wheat can be used to create mutations in an Lpx-B1.3 gene. In another embodiment, any cultivar of wheat can be used to create mutations in an Lpx-A1 gene.

In one embodiment, any cultivar of wheat can be used as lines to cross Lpx mutations into different cultivars.

In another embodiment, any cultivar of wheat having at least one Lpx gene may be used including but not limited to hard red spring wheat, hard white winter wheat, durum wheat, soft white spring wheat, soft white winter wheat, hard red winter wheat, common wheat, spelt wheat, emmer wheat, pasta wheat and turgidum wheat.

In one embodiment, hard red spring wheat includes but is not limited to Bullseye, Cabernet, Cal Rojo, Hank, Joaquin, Kelse, Lariat, Lassik, Malbec, Mika, PR 1404, Redwing, Summit 515, SY 314, Triple IV, Ultra, WB-Patron, WB-Rockland, Yecora Rojo, Accord, Aim, Anza, Baker, Beth Hashita, Bonus, Borah, Brim, Brooks, Buck Pronto, Butte 86, Cavalier, Challenger, Chief, Ciano T79, Colusa, Companion, Copper, Cuyama, Dash 12, Eldon, Enano, Express, Expresso, Jefferson, Genero F81, Grandin, Helena 554, Hollis, Imuris T79, Inia 66R, Jerome, Kern, Len, Marshall, McKay, Nomad, Northwest 10, Oslo, Pavon F76, Pegasus, Pitic 62, Poco Red, Powell, Probrand 711, Probrand 751, Probrand 771, Probrand 775, Probred, Prointa Queguay, Prointa Quintal, Rich, RSI 5, Sagittario, Scarlet, Serra, Shasta, Solano, Spillman, Sprite, Stander, Stellar, Stoa, Success, Summit, Sunstar 2, Sunstar King, Tadinia, Tammy, Tanori 71, Tara 2000, Tempo, Tesia T79, Topic, UI Winchester, Vance, Vandal, W444, Wampum, Wared, WB-Fuzion, Westbred 906R, Westbred 911, Westbred 926, Westbred 936, Westbred Discovery, Westbred Rambo, Yolo, and Zeke.

In another embodiment, hard white wheat includes but is not limited to Blanca Fuerte, Blanca Grande 515, Blanca Royale, Clear White, Patwin, Patwin 515, WB-Cristallo, WB-Paloma, WB-Perla, Alta Blanca, Blanca Grande, Delano, Golden Spike, ID377S, Klasic, Lochsa, Lolo, Macon, Otis, Phoenix, Pima 77, Plata, Pristine, Ramona 50, Siete Cerros 66, Vaiolet, and Winsome.

In yet another embodiment, durum wheat includes but is not limited to Crown, Desert King, Desert King HP, Duraking, Fortissimo, Havasu, Kronos, Maestrale, Normanno, Orita, Platinum, Q-Max, RSI 59, Saragolla, Tango, Tipai, Topper, Utopia, Volante, WB-Mead, Westmore, Aldente, Aldura, Altar 84, Aruba, Bittern, Bravadur, Candura, Cortez, Deluxe, Desert Titan, Durex, Durfort, Eddie, Germains 5003D, Imperial, Kofa, Levante, Matt, Mead, Mexicali 75, Minos, Modoc, Mohawk, Nudura, Ocotillo, Produra, Reva, Ria, Septre, Sky, Tacna, Titan, Trump, Ward, Westbred 803, Westbred 881, Westbred 883, Westbred 1000D, Westbred Laker, Westbred Turbo, and Yavaros 79.

In another embodiment, soft white spring wheat includes but is not limited to Alpowa, Alturas, Babe, Diva, JD, New Dirkwin, Nick, Twin, Whit, Blanca, Bliss, Calorwa, Centennial, Challis, Dirkwin, Eden, Edwall, Fielder, Fieldwin, Jubilee, Louise, Owens, Penawawa, Pomerelle, Sterling, Sunstar Promise, Super Dirkwin, Treasure, UI Cataldo, UI Pettit, Urquie, Vanna, Waduel, Waduel 94, Wakanz, Walladay, Wawawai, Whitebird, and Zak.

In still another embodiment, soft white winter wheat includes but is not limited to AP Badger, AP Legacy, Brundage 96, Bruneau, Cara, Goetze, Legion, Mary, Skiles, Stephens, SY Ovation, Tubbs, WB-Junction, WB-528, Xerpha, Yamhill, Barbee, Basin, Bitterroot, Bruehl, Castan, Chukar, Coda, Daws, Edwin, Eltan, Faro, Finch, Foote, Gene, Hill 81, Hiller, Hubbard, Hyak, Hyslop, Idaho 587, Kmor, Lambert, Lewjain, MacVicar, Madsen, Malcolm, Masami, McDermid, Moro, Nugaines, ORCF-101, ORCF-102, ORCF-103, Rod, Rohde, Rulo, Simon, Salute, Temple, Tres, Tubbs 06, UICF-Brundage, WB-523, and Weatherford.

In another embodiment, hard red winter wheat includes but is not limited to Andrews, Archer, Batum, Blizzard, Bonneville, Boundary, Declo, Deloris, Finley, Garland, Hatton, Hoff, Longhorn, Manning, Meridian, Promontory, Vona, Wanser, Winridge.

In another embodiment, common wheat (hexaploid, free threshing), *Triticum aestivum* ssp *aestivum* includes but is not limited to Sonora, Wit Wolkoring, Chiddam Blanc De Mars, India-Jammu, Foisy.

In still another embodiment, spelt wheat (hexaploid, not free threshing), *Triticum aestivum* ssp *spelta* includes but is not limited to Spanish Spelt, Swiss Spelt.

In yet another embodiment, Emmer Wheat (tetraploid), *Triticum turgidum* ssp. *dicoccum* includes but is not limited to Ethiopian Blue Tinge.

In another embodiment, pasta wheat (tetraploid, free threshing), *Triticum turgidum* ssp *durum* includes but is not limited to Blue Beard, *Durum*-Iraq.

In yet another embodiment, *Turgidum* Wheat (tetraploid, free threshing), *Triticum turgidum* ssp *turgidum* includes but is not limited to Akmolinka, Maparcha.

In one embodiment, a cultivar of wheat having at least one Lpx1 gene with substantial percent identity to SEQ ID NO: 1, SEQ ID NO: 2, SEQ ID NO: 4, SEQ ID NO: 5, and SEQ ID NO. 15 may be used with the methods and compositions disclosed herein.

As used herein with regard to the wheat cultivars, "substantial percent identity" means that the DNA sequence of the gene is sufficiently similar to SEQ ID NO: 1, 2, 4, and 5 at the nucleotide level to code for a substantially similar protein, allowing for allelic differences (or alternate mRNA splicing) between cultivars. In accordance with one embodiment of the invention, "substantial percent identity" may be present when the percent identity in the coding region between the Lpx1 gene and SEQ ID NO: 1, 2, 4, and 5 is as low as about 85%, provided that the percent identity in the conserved regions of the gene is higher (e.g., at least about 90%). Preferably the percent identity in the coding region is 85-90%, more preferably 90-95%, and optimally, it is above 95%. Thus, one of skill in the art may prefer to utilize a wheat cultivar having commercial popularity or one having specific desired characteristics in which to create the Lpx1-mutated wheat plants, without deviating from the scope and intent of the present invention. Alternatively, one of skill in the art may prefer to utilize a wheat cultivar having few polymorphisms, such as an in-bred cultivar, in order to facilitate screening for mutations within one or more Lpx1 genes in accordance with the present invention.

VI. Representative Methodology for Identification of Lpx1 Mutations

In order to create and identify the Lpx1 mutations and wheat plants disclosed herein, a method known as TILLING (Targeting Induced Local Lesions IN Genomes) was utilized. See McCallum et al., *Nature Biotechnology* 18:455-457, 2000; McCallum et al., *Plant Physiology*, 123:439-442, 2000; U.S. Publication No. 20040053236; and U.S. Pat. No. 5,994,075, all of which are incorporated herein by reference. In the basic TILLING methodology, plant materials, such as seeds, are subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation are grown into adult M3 plants and screened for the phenotypic characteristics associated with the gene of interest.

The hexaploid cultivar Express was used.

In one embodiment, seeds from wheat are mutagenized and then grown into M1 plants. The M1 plants are then allowed to self-pollinate and seeds from the M1 plant are grown into M2 plants, which are then screened for mutations in their Lpx1 loci. While M1 plants can be screened for mutations in accordance with alternative embodiments of the invention, one advantage of screening the M2 plants is that all somatic mutations correspond to germline mutations.

One of skill in the art will understand that a variety of wheat plant materials, including, but not limited to, seeds, pollen, plant tissue or plant cells, may be mutagenized in order to create the Lpx-mutated wheat plants disclosed herein. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen, thus these M1 plants may then be screened for Lpx1 mutations instead of waiting until the M2 generation.

Mutagens that create primarily point mutations and deletions, insertions, transversions, and or transitions, such as chemical mutagens or radiation, may be used to create the mutations. Mutagens conforming with the method of the invention include, but are not limited to, ethyl methanesulfonate (EMS), methylmethane sulfonate (MMS), N-ethyl-N-nitrosourea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7, 12 dimethyl-benz(a) anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9 [3-(ethyl-2-chloro-ethypaminopropylamino] acridine dihydrochloride (ICR-170), formaldehyde, fast neutrons, and gamma irradiation. Spontaneous mutations in a Lpx1 gene that may not have been directly caused by the mutagen can also be identified.

Other methods such as genome editing can also be used to alter the sequence of a target gene including its promoter to up or down regulate expression or activity. These methods are known to those skilled in the art, and include CRISPR, Talens, Zinc finger nucleases and miRNA among other methods. For example, see a review of these methods by Xiong et al. *Horticulture Research* 2: 15019, 2015.

Any suitable method of plant DNA preparation now known or hereafter devised may be used to prepare the wheat plant DNA for Lpx1 mutation screening. For example, see Chen & Ronald, *Plant Molecular Biology Reporter* 17:53-57, 1999; Stewart and Via, *Bio Techniques* 14:748-749, 1993. Additionally, several commercial kits designed for this purpose are available, including kits from Qiagen (Valencia, Calif.) and Qbiogene (Carlsbad, Calif.).

In one embodiment, prepared DNA from individual wheat plants are pooled in order to expedite screening for mutations in one or more Lpx1 genes of the entire population of plants originating from the mutagenized plant tissue. The size of the pooled group may be dependent upon the sensitivity of the screening method used. Preferably, groups of two or more individual wheat plants are pooled.

In another embodiment, after the DNA samples are pooled, the pools are subjected to Lpx1 sequence-specific amplification techniques, such as Polymerase Chain Reaction (PCR). For a general overview of PCR, see *PCR*

Protocols: A Guide to Methods and Applications (Innis, Gelfand, Sninsky, and White, eds.), Academic Press, San Diego, 1990.

Any primer specific to an Lpx1 locus or the sequences immediately adjacent to one of these loci may be utilized to amplify the Lpx1 sequences within the pooled DNA sample. Preferably, the primer is designed to amplify the regions of the Lpx1 locus where useful mutations are most likely to arise. Most preferably, the primer is designed to detect exonic regions of one or more Lpx1 genes. Additionally, it is preferable for the primer to target known polymorphic sites to design genome specific primers in order to ease screening for point mutations in a particular genome.

In one embodiment, primers are designed based upon the Lpx-D1 and Lpx-B1.2 DNA sequences (SEQ ID NOs: 1, 2, 4, 5 and 15). Exemplary primers (SEQ ID NOs: 7-14, 16 and 17) that have proven useful in identifying useful mutations within the Lpx1 sequences are shown in Table 4. These primers are also detailed in the Sequence Listing appended hereto.

TABLE 4

Exemplary TILLING Primers

| | | |
|---|---|---|
| SEQ ID NO: 7 | TaLpx1D_4_L-1 | TGGTGAGAGCACGCAAATCTTACTTGG |
| SEQ ID NO: 8 | TaLpxB1.2-D1-5R1 | CGTTTCAATCATAGGTCAGTTGTGCATCGA |
| SEQ ID NO: 9 | TaLpx1D_67_R_3 | CGCGTACGGGTAGTCCGACACCAGAAG |
| SEQ ID NO: 10 | TaLpx1D_In1_L4 | GCATGCCATGGAAAGAAGAGACAATAGTAGC |
| SEQ ID NO: 11 | TaLpx1D_3_R-1 | TGCGTGCTCTCACCATGGACAACATACATA |
| SEQ ID NO: 12 | TaLpx1D_Ex5_L6 | GCAGGCGCTGGAAAGTAACAGGCTCT |
| SEQ ID NO: 13 | TaLpx1D_Ex7_R3 | TGGACGAGACGAAGCTCCGATGTACCA |
| SEQ ID NO: 14 | TaLpx1.2B_4_L-1 | GAGGTGAGAGCGTGCCTGATCTTAATTTG |
| SEQ ID NO: 16 | LpxD1proL | TCATGCCGCTGATCGTCGC |
| SEQ ID NO: 17 | LpxD1proR | CTTGCTGCTATTTCAGTACCG |

In another embodiment, the PCR amplification products may be screened for Lpx1 mutations using any method that identifies nucleotide differences between wild type and mutant sequences. These may include, for example, without limitation, sequencing, denaturing high pressure liquid chromatography (dHPLC), constant denaturant capillary electrophoresis (CDCE), temperature gradient capillary electrophoresis (TGCE) (see Li et al., Electrophoresis 23(10):1499-1511, 2002), or by fragmentation using enzymatic cleavage, such as used in the high throughput method described by Colbert et al., Plant Physiology 126:480-484, 2001. Preferably, the PCR amplification products are incubated with an endonuclease that preferentially cleaves mismatches in heteroduplexes between wild type and mutant sequences.

In another embodiment, cleavage products are electrophoresed using an automated sequencing gel apparatus, and gel images are analyzed with the aid of a standard commercial image-processing program.

In yet another embodiment, once an M2 plant having a mutated Lpx1 gene sequence is identified, the mutations are analyzed to determine their effect on the expression, translation, and/or activity of an Lpx1 enzyme. In one embodiment, the PCR fragment containing the mutation is sequenced, using standard sequencing techniques, in order to determine the exact location of the mutation in relation to the overall Lpx1 sequence. Each mutation is evaluated in order to predict its impact on protein function (i.e., from completely tolerated to causing loss-of-function) using bioinformatics tools such as SIFT (Sorting Intolerant from Tolerant; Ng and Henikoff, Nucleic Acids Research 31:3812-3814, 2003), PSSM (Position-Specific Scoring Matrix; Henikoff and Henikoff, Computer Applications in the Biosciences 12:135-143, 1996) and PARSESNP (Taylor and Greene, Nucleic Acids Research 31:3808-3811, 2003). For example, a SIFT score that is less than 0.05 and a large change in PSSM score (e.g., roughly 10 or above) indicate a mutation that is likely to have a deleterious effect on protein function. These programs are known to be predictive, and it is understood by those skilled in the art that the predicted outcomes are not always accurate.

In another embodiment, if the initial assessment of a mutation in the M2 plant indicates it to be of a useful nature and in a useful position within an Lpx1 gene, including its promoter, then further phenotypic analysis of the wheat plant containing that mutation may be pursued. In hexaploid wheat, mutations in each of the A, B and D genomes usually must be combined before a phenotype can be detected. In tetraploid wheat, A and B genome mutations are combined. In addition, the mutation containing plant can be backcrossed or outcrossed two times or more in order to eliminate background mutations at any generation. Then the backcrossed or outcrossed plant can be self-pollinated or crossed in order to create plants that are homozygous for the Lpx1 mutations.

Several physical characteristics of these homozygous Lpx1 mutant plants are assessed to determine if the mutation results in a useful phenotypic change in the wheat plant without resulting in undesirable negative effects, such as significantly reduced seed yields.

VII. Methods of Producing a Wheat Plant

In another embodiment, the disclosure relates to a method for producing a wheat plant with increased oxidative stability. In another embodiment, the invention relates to a method for producing a wheat plant with an increased shelf-life.

In another embodiment, the disclosure relates to a method of out-crossing Lpx1 gene mutations to wild type wheat.

In another embodiment, the disclosure relates to a method for producing a wheat plant having increased oxidative stability and products from grain of said wheat plant having increased shelf life. In still another embodiment, the invention relates to a method for producing a wheat plant having reduced activity of one or more Lpx1 enzymes compared to the wild type wheat plants.

In one embodiment, the method comprises inducing at least one non-transgenic mutation in at least one copy of an Lpx1 gene in plant material or plant parts from a parent wheat plant; growing or using the mutagenized plant material to produce progeny wheat plants; analyzing mutagenized plant material and/or progeny wheat plants to detect at least one mutation in at least one copy of a Lpx1 gene; and selecting progeny wheat plants that have at least one mutation in at least one copy of an Lpx1 gene.

In another embodiment, the method further comprises crossing progeny wheat plants that have at least one mutation in at least one copy of an Lpx1 gene with other progeny wheat plants that have at least one mutation in a different copy of an Lpx1 gene. The process of identifying progeny wheat plants with mutations and crossing said progeny wheat plants with other progeny wheat plants, which have mutations, can be repeated to produce progeny wheat plants with reduced Lpx1 enzyme activity.

In another embodiment, the level of activity of the Lpx1 protein in the wheat plant is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, or 95-99% of the level of activity of the Lpx1 protein in the wild type plant.

A. Methods of Producing a Wheat Plant with One or More Mutations in the Lpx1 Gene in More than One Genome In still another embodiment, the disclosure relates to a method for producing a wheat plant comprising inducing at least one non-transgenic mutation in at least one copy of an Lpx1 gene in plant material from a parent wheat plant that comprises a mutation in an Lpx1 gene; growing or using the mutagenized plant material to produce progeny wheat plants; and selecting progeny wheat plants that have at least one mutation in at least two copies of an Lpx1 gene. For example, the parent wheat plant may have a mutation in an Lpx-D1 gene of the D genome. The selected progeny wheat plants may have a mutation in an Lpx-D1 gene of the D genome and one or more mutations in the Lpx1 gene of the B genome. This example is provided merely for clarification and should not limit the methods disclosed herein.

In yet another embodiment, the invention relates to a method for producing a wheat plant comprising inducing at least one non-transgenic mutation in at least one copy of an Lpx1 gene in plant material from a parent wheat plant that comprises at least one mutation in two Lpx1 genes; growing or using the mutagenized plant material to produce progeny wheat plants; and selecting progeny wheat plants that have at least one mutation in three copies of an Lpx1 gene. In this embodiment, there would be at least one mutation in the Lpx1 gene of the A, B and D genomes.

In another embodiment, the disclosure relates to a method for producing a wheat plant comprising crossing a first wheat plant that has at least one non-transgenic mutation in a first Lpx1 gene with a second wheat plant that has at least one non-transgenic mutation in a second Lpx1 gene; and selecting progeny wheat plants that have at least one mutation in at least two copies of an Lpx1 gene.

In another embodiment, the disclosure relates to a method for producing a wheat plant comprising crossing a first wheat plant that has at least one non-transgenic mutation in a first and second Lpx1 gene with a second wheat plant that has at least one non-transgenic mutation in a third Lpx1 gene; and selecting progeny wheat plants that have at least one mutation in all three copies of an Lpx1 gene. In this embodiment, there would be at least one mutation in the Lpx1 gene of the A, B and D genomes.

VIII. Wheat Plant, Wheat Seed and Parts of Wheat Plant

In one embodiment, a wheat plant is produced according to the methods disclosed herein. In another embodiment, the wheat plant, wheat seed or parts of a wheat plant have one or more mutations in an Lpx1 gene. In another embodiment, the wheat plant, wheat seed or parts of a wheat plant have one or more mutations in Lpx1 genes.

In another embodiment, the disclosure relates to a wheat plant, wheat seed or parts of a wheat plant comprising one or more non-transgenic mutations in the Lpx1 gene. In another embodiment, the disclosure relates to a wheat plant, wheat seed or parts of a wheat plant comprising at least one non-transgenic mutation in the Lpx1 gene in each of two genomes. In still another embodiment, the disclosure relates to a wheat plant, wheat seed or parts of a wheat plant comprising at least one non-transgenic mutation in the Lpx1 gene in each of three genomes.

In one embodiment, the wheat plant, wheat seed or parts of a wheat plant comprises one or more non-transgenic mutations in both alleles of the Lpx1 gene in the A genome. In another embodiment, the non-transgenic mutations are identical in both alleles of the Lpx1 gene of the A genome.

In one embodiment, the wheat plant, wheat seed or parts of a wheat plant comprises one or more non-transgenic mutations in both alleles of the Lpx1 gene in the B genome. In another embodiment, the non-transgenic mutations are identical in both alleles of the Lpx1 gene of the B genome.

In one embodiment, the wheat plant, wheat seed or parts of a wheat plant comprises one or more non-transgenic mutations in both alleles of the Lpx1 gene in the D genome. In another embodiment, the non-transgenic mutations are identical in both alleles of the Lpx1 gene of the D genome.

In another embodiment, the wheat plant, wheat seed or parts of the wheat plant comprise a polynucleotide with one or more non-transgenic mutations listed in Table 1 and is 85%, 86%, 87%, 88%, 89%, 90%, 91%, 92%, 93%, 94%, 95%, 96%, 97%, 98%, 99% or greater than 99% identical or similar to SEQ ID NO: 4.

In still another embodiment, the wheat plant, wheat seed or parts of a wheat plant comprise a polynucleotide with one or more non-transgenic mutations listed in Table 1 that codes for a Lpx1 protein, wherein the Lpx1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 6.

In another embodiment, the wheat plant, wheat seed or parts of the wheat plant comprise a polynucleotide with one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 4.

In still another embodiment, the wheat plant, wheat seed or parts of a wheat plant comprise a polynucleotide with one or more non-transgenic mutations that codes for a Lpx1 protein, wherein the Lpx1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 6.

In another embodiment, the wheat plant, wheat seed or parts of the wheat plant comprise a polynucleotide with one or more non-transgenic mutations listed in Table 2 and is 85%, 86%, 87%, 88%, 89%, 90%, 91%, 92%, 93%, 94%, 95%, 96%, 97%, 98%, 99% or greater than 99% identical or similar to SEQ ID NO: 1.

In still another embodiment, the wheat plant, wheat seed or parts of a wheat plant comprise a polynucleotide with one or more non-transgenic mutations listed in Table 2 that codes for a Lpx1 protein, wherein the Lpx1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 3.

In another embodiment, the wheat plant, wheat seed or parts of the wheat plant comprise a polynucleotide with one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 2.

In still another embodiment, the wheat plant, wheat seed or parts of a wheat plant comprise a polynucleotide with one or more non-transgenic mutations that codes for a Lpx1 protein, wherein the Lpx1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 3.

In another embodiment, the wheat plant, wheat seed or parts of a wheat plant has one or more mutations in the Lpx1 gene including but not limited to one or more mutations enumerated in Tables 1-3 and corresponding mutations in the homoeologues. A wheat plant, wheat seed or parts of a wheat plant can be generated having 1, 2, 3, 4, 5, 6, 7, 8, 9, 10, 11, 12, 13, 14, 15, 16, 17, 18, 19, 20, 21, 22, 23, 24, 25 or greater than 25 of the mutations disclosed herein including but not limited to the mutations disclosed in Tables 1, 2 and 3, as well as mutations in the corresponding homoeologues.

In another embodiment, the wheat seed containing one or more mutations disclosed herein germinates at a rate comparable to wild type wheat seed. In still another embodiment, the wheat seed containing one or more mutations disclosed herein has physical characteristics, including but not limited to size, weight, length, comparable to wild type wheat seed.

In still another embodiment, the wheat plants containing one or more mutations disclosed herein has fertility comparable wild type wheat plants.

IX. Grain, Flour and Starch

In another embodiment, the disclosure relates to a wheat grain, flour or starch comprising one or more non-transgenic mutations in the Lpx1 gene. In another embodiment, the invention relates to wheat grain comprising an embryo, wherein the embryo comprises one or more non-transgenic mutations in an Lpx1 gene.

In another embodiment, the wheat grain, flour or starch comprises one or more non-transgenic mutations in the Lpx1 genes including but not limited to the mutations recited in Tables 1-3 and the corresponding mutations in homoeologues.

In still another embodiment, the disclosure relates to a wheat grain or flour comprising at least one non-transgenic mutation in the Lpx1 gene in one, two or three genomes.

In still another embodiment, the invention relates to a wheat grain, flour or starch comprising one or more non-transgenic mutations in the Lpx-D1 gene. In another embodiment, the non-transgenic mutations are identical in both alleles of the Lpx-D1 gene of the D genome.

In one embodiment, the wheat grain, flour or starch comprises one or more non-transgenic mutations in both alleles of the Lpx-B1.1a gene in the B genome. In another embodiment, the non-transgenic mutations are identical in both alleles of the Lpx-B1.1a gene of the B genome.

In one embodiment, the wheat grain, flour or starch comprises one or more non-transgenic mutations in both alleles of the Lpx-B1.1b gene in the B genome. In another embodiment, the non-transgenic mutations are identical in both alleles of the Lpx-B1.1b gene of the B genome.

In one embodiment, the wheat grain, flour or starch comprises one or more non-transgenic mutations in both alleles of the Lpx-B1.1c gene in the B genome. In another embodiment, the non-transgenic mutations are identical in both alleles of the Lpx-B1.1c gene of the B genome.

In one embodiment, the wheat grain, flour or starch comprises one or more non-transgenic mutations in both alleles of the Lpx-B1.2 gene in the B genome. In another embodiment, the non-transgenic mutations are identical in both alleles of the Lpx-B1.2 gene of the B genome.

In one embodiment, the wheat grain, flour or starch comprises one or more non-transgenic mutations in both alleles of the Lpx-B1.3 gene in the B genome. In another embodiment, the non-transgenic mutations are identical in both alleles of the Lpx-B1.3 gene of the B genome.

In one embodiment, the disclosure relates to wheat grain, wheat flour or starch comprising a polynucleotide of the Lpx-D1 promoter in the D genome with one or more non-transgenic mutations listed in Table 3 and corresponding to SEQ ID NO: 15. In another embodiment, the wheat grain or wheat flour comprise a polynucleotide with one or more non-transgenic mutations listed in Table 3 and is 85%, 86%, 87%, 88%, 89%, 90%, 91%, 92%, 93%, 94%, 95%, 96%, 97%, 98%, 99% or greater than 99% identical or similar to SEQ ID NO: 15.

In one embodiment, the disclosure relates to wheat grain, wheat flour or starch comprising a polynucleotide of the Lpx-D1 gene in the D genome with one or more non-transgenic mutations listed in Table 2 and corresponding to SEQ ID NO: 1. In another embodiment, the wheat grain or wheat flour comprise a polynucleotide with one or more non-transgenic mutations listed in Table 2 and is 85%, 86%, 87%, 88%, 89%, 90%, 91%, 92%, 93%, 94%, 95%, 96%, 97%, 98%, 99% or greater than 99% identical or similar to SEQ ID NO: 1.

In still another embodiment, wheat grain, wheat flour or starch comprise a polynucleotide with one or more non-transgenic mutations listed in Table 2 that codes for a Lpx1 protein, wherein the Lpx1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 3.

In one embodiment, the disclosure relates to wheat grain, wheat flour or starch comprising a polynucleotide of the Lpx-B1.2 gene in the B genome with one or more non-transgenic mutations listed in Table 1 and corresponding to SEQ ID NO: 4. In another embodiment, the wheat grain or wheat flour comprise a polynucleotide with one or more non-transgenic mutations listed in Table 1 and is 85%, 86%, 87%, 88%, 89%, 90%, 91%, 92%, 93%, 94%, 95%, 96%, 97%, 98%, 99% or greater than 99% identical or similar to SEQ ID NO: 4.

In still another embodiment, wheat grain, wheat flour or starch comprise a polynucleotide with one or more non-transgenic mutations listed in Table 1 that codes for a Lpx-B1.2 protein, wherein the Lpx-B1.2 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 6.

In still another embodiment, the disclosure relates to wheat grain or flour comprising an endosperm and a reduced gene expression level, activity or expression level and activity of the Lpx1 gene as compared to wild type wheat grain or flour.

In yet another embodiment, the disclosure relates to wheat grain or flour with one or more mutations in the Lpx1 gene exhibiting increased shelf life as compared to wild type wheat grain or flour. In another embodiment, wheat grain or flour with one or more mutations in the Lpx1 gene exhibits from 25-30%, 30-35%, 35-40%, 45-50%, 50-55%, 55-60%, 60-65%, 65-70%, 70-75%, 75-80%, 80-85%, 85-90%, 90-95%, and greater than 95% increased shelf life as compared to wild type grain or flour.

In yet another embodiment, the disclosure relates to wheat grain or flour with one or more mutations in the Lpx-D1 gene exhibiting increased shelf life as compared to wild type wheat grain or flour. In another embodiment, wheat grain or flour with one or more mutations in the Lpx-D1 gene exhibits from 25-30%, 30-35%, 35-40%, 45-50%, 50-55%, 55-60%, 60-65%, 65-70%, 70-75%, 75-80%, 80-85%, 85-90%, 90-95%, and greater than 95% increased shelf life as compared to wild type grain or flour.

In yet another embodiment, the disclosure relates to wheat grain or flour with one or more mutations in the Lpx-D1 and Lpx-B1.2 genes exhibiting increased shelf life as compared to wild type wheat grain or flour. In another embodiment, wheat grain or flour with one or more mutations in the Lpx-D1 and Lpx-B1.2 genes exhibits from 25-30%, 30-35%, 35-40%, 45-50%, 50-55%, 55-60%, 60-65%, 65-70%, 70-75%, 75-80%, 80-85%, 85-90%, 90-95%, and greater than 95% increased shelf life as compared to wild type grain or flour.

X. Food Products

In one embodiment, the disclosure is directed to a flour or other product produced from the grain or flour discussed above. In another embodiments, the flour, the coarse fraction or purified starch may be a component of a food product.

The food product includes but is not limited to a bagel, a biscuit, a bread, a bun, a croissant, a dumpling, an English muffin, a muffin, a pita bread, a quickbread, a refrigerated/frozen dough products, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In one embodiment, the flour is a whole grain flour (ex.—an ultrafine-milled whole grain flour, such as an ultrafine-milled whole grain wheat flour). In one embodiment, the whole grain flour includes a refined flour constituent (ex.—refined wheat flour or refined flour) and a coarse fraction (ex.—an ultrafine-milled coarse fraction). Refined wheat flour may be flour which is prepared, for example, by grinding and bolting (sifting) cleaned wheat. The Food and Drug Administration (FDA) requires flour to meet certain particle size standards in order to be included in the category of refined wheat flour. The particle size of refined wheat flour is described as flour in which not less than 98% passes through a cloth having openings not larger than those of woven wire cloth designated "212 micrometers (U.S. Wire 70)."

In another embodiment, the coarse fraction includes at least one of: bran and germ. For instance, the germ is an embryonic plant found within the wheat kernel. The germ includes lipids, fiber, vitamins, protein, minerals and phytonutrients, such as flavonoids. The bran may include several cell layers and has a significant amount of lipids, fiber, vitamins, protein, minerals and phytonutrients, such as flavonoids.

For example, the coarse fraction or whole grain flour or refined flour of the present invention may be used in various amounts to replace refined or whole grain flour in baked goods, snack products, and food products. The whole grain flour (i.e.—ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In another embodiment, the whole grain flour or coarse fraction or refined flour may be a component of a nutritional supplement. The nutritional supplement may be a product that is added to the diet containing one or more ingredients, typically including: vitamins, minerals, herbs, amino acids, enzymes, antioxidants, herbs, spices, probiotics, extracts, prebiotics and fiber.

In a further embodiment, the nutritional supplement may include any known nutritional ingredients that will aid in the overall health of an individual, examples include but are not limited to carotenoids, vitamins, minerals, other fiber components, fatty acids, antioxidants, amino acids, peptides, proteins, lutein, ribose, omega-3 fatty acids, and/or other nutritional ingredients. Because of the high nutritional content of the endosperm of the present invention, there may be many uses that confer numerous benefits to an individual, including, delivery of fiber and other essential nutrients, increased digestive function and health, weight management, blood sugar management, heart health, diabetes risk reduction, potential arthritis risk reduction, and overall health and wellness for an individual.

In still another embodiments, the whole grain flour or coarse fraction or refined flour may be a component of a dietary supplement. The Code of Federal Regulations defines a dietary supplement as a product that is intended to supplement the diet and contains one or more dietary ingredients including: vitamins, minerals, herbs, botanicals, amino acids, and other substances or their constituents; is intended to be taken by mouth as a pill, capsule, tablet, or liquid; and is labeled on the front panel as being a dietary supplement.

In yet another embodiment, the whole grain flour or coarse fraction or refined flour may be a fiber supplement or a component thereof. The fiber supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage.

In another embodiment, the whole grain flour or coarse fraction or refined flour may be included as a component of a digestive supplement. The whole grain flour or coarse fraction or refined flour may be a component of a digestive supplement alone or in combination with one or more prebiotic compounds and/or probiotic organisms. Prebiotic compounds are non-digestible food ingredients that may beneficially affect the host by selectively stimulating the growth and/or the activity of a limited number of microorganisms in the colon. Examples of prebiotic compounds within the scope of the invention, may include, but are not limited to: oligosaccharides and inulins.

Probiotics are microorganisms which, when administered in adequate amounts, confer a health benefit on the host. Probiotic organisms include, but are not limited to: *Lactobacillus, Bifidobacteria, Escherichia, Clostridium, Lactococcus, Streptococcus, Enterococcus*, and *Saccharomyces*.

In yet another embodiment, the whole grain flour or coarse fraction or refined flour may be included as a component of a functional food. The Institute of Food Technologists defines functional foods as, foods and food components that provide a health benefit beyond basic nutrition. This includes conventional foods, fortified, enriched, or enhanced foods, and dietary supplements. The whole grain flour and coarse fraction or refined flour include numerous vitamins and minerals, have high oxygen radical absorption capacities, and are high in fiber, making them ideally suited for use in/as a functional food.

In another embodiment, the whole grain flour or coarse fraction or refined flour may be used in medical foods. Medical food is defined as a food that is formulated to be consumed or administered entirely under the supervision of a physician and which is intended for the specific dietary management of a disease or condition for which distinctive nutritional requirements, based on recognized scientific principles, are established by medical evaluation. The nutrient contents and antioxidant capacities of the whole grain flour and coarse fraction or refined flour make them ideal for use in medical foods.

In yet another embodiment, the whole grain flour or coarse fraction or refined flour may also be used in pharmaceuticals. The whole grain flour and coarse fraction or refined flour are high in fiber and have a very fine granulation making them suitable for use as a carrier in pharmaceuticals.

In still another embodiment, delivery of the whole grain flour or coarse fraction or refined flour as a nutritional supplement, dietary supplement or digestive supplement is contemplated via delivery mechanisms where the whole grain flour or coarse fraction is the single ingredient or one of many nutritional ingredients. Examples of delivery mechanisms include but are not limited to: instant beverage mixes, ready-to-drink beverages, nutritional bars, wafers, cookies, crackers, gel shots, capsules, and chews.

In yet another embodiment, a milling process may be used to make a multi-wheat flour, or a multi-grain coarse fraction. In one embodiment, bran and germ from one type of wheat may be ground and blended with ground endosperm or whole grain wheat flour of another type of wheat. Alternatively bran and germ of one type of grain may be ground and blended with ground endosperm or whole grain flour of another type of grain.

In still another embodiment, bran and germ from a first type of wheat or grain may be blended with bran and germ from a second type of wheat or grain to produce a multi-grain coarse fraction. It is contemplated that the invention encompasses mixing any combination of one or more of bran, germ, endosperm, and whole grain flour of one or more grains. This multi-grain, multi-wheat approach may be used to make custom flour and capitalize on the qualities and nutritional contents of multiple types of grains or wheats to make one flour.

The whole grain flour of the invention may be produced via a variety of milling processes. One exemplary process involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like.

After grinding, the grain is discharged and conveyed to a sifter. Any sifter known in the art for sifting a ground particle may be used. Material passing through the screen of the sifter is the whole grain flour of the invention and requires no further processing. Material that remains on the screen is referred to as a second fraction. The second fraction requires additional particle reduction. Thus, this second fraction may be conveyed to a second passage grinder.

After grinding, the second fraction may be conveyed to a second sifter. Material passing through the screen of the second sifter is the whole grain flour. The material that remains on the screen is referred to as the fourth fraction and requires further processing to reduce the particle size. The fourth fraction on the screen of the second sifter is conveyed back into either the first passage grinder or the second passage grinder for further processing via a feedback loop.

It is contemplated that the whole grain flour, coarse fraction, purified starch and/or grain products of the invention may be produced by a number of milling processes known in the art.

XI. Plant Breeding

In another embodiment, the disclosure is directed to methods for plant breeding using wheat plants and plant parts with one or more non-transgenic mutations in the Lpx1 genes.

One such embodiment is the method of crossing wheat variety with one or more non-transgenic mutations in the Lpx1 genes with another variety of wheat to form a first generation population of F1 plants. The population of first generation F1 plants produced by this method is also an embodiment of the invention. This first generation population of F1 plants will comprise an essentially complete set of the alleles of wheat variety with one or more non-transgenic mutations in the Lpx1 genes. One of ordinary skill in the art can utilize either breeder books or molecular methods to identify a particular F1 plant produced using wheat variety with one or more non-transgenic mutations in the Lpx1 genes, and any such individual plant is also encompassed by this invention. These embodiments also cover use of transgenic or backcross conversions of wheat varieties with one or more mutations in the Lpx1 genes to produce first generation F1 plants.

In another embodiment, the invention relates to a method of developing a progeny wheat plant. A method of developing a progeny wheat plant comprises crossing a wheat variety with one or more non-transgenic mutations in the Lpx1 genes with a second wheat plant and performing a breeding method. A specific method for producing a line derived from wheat variety with one or more non-transgenic mutations in the Lpx1 genes is as follows.

One of ordinary skill in the art would cross wheat variety with one or more non-transgenic mutations in the Lpx1 gene or genes with another variety of wheat, such as an elite variety. The F1 seed derived from this cross would be grown to form a homogeneous population. The F1 seed would contain one set of the alleles from wheat variety with one or more non-transgenic mutations in the Lpx1 gene and one set of the alleles from the other wheat variety.

The F1 genome would be made-up of 50% wheat variety with one or more non-transgenic mutations in the Lpx1 gene and 50% of the other elite variety. The F1 seed would be grown to form F2 seed. The F1 seed could be allowed to self, or bred with another wheat cultivar.

On average the F2 seed would have derived 50% of its alleles from wheat variety with one or more non-transgenic mutations in the Lpx1 gene and 50% from the other wheat variety, but various individual plants from the population would have a much greater percentage of their alleles derived from wheat variety with one or more non-transgenic mutations in the Lpx1 gene (Wang J. and R. Bernardo, 2000, Crop Sci. 40:659-665 and Bernardo, R. and A. L. Kahler, 2001, Theor. Appl. Genet. 102:986-992).

The F2 seed would be grown and selection of plants would be made based on visual observation and/or measurement of traits and/or marker assisted selection. The wheat variety with one or more non-transgenic mutations in the Lpx1 gene-derived progeny that exhibit one or more of the desired wheat variety with one or more non-transgenic mutations in the Lpx1 gene-derived traits would be selected and each plant would be harvested separately. This F3 seed from each plant would be grown in individual rows and allowed to self. Then selected rows or plants from the rows would be harvested and threshed individually. The selections would again be based on visual observation and/or measurements for desirable traits of the plants, such as one or more of the desirable wheat variety with one or more non-transgenic mutations in the Lpx1 gene-derived traits.

The process of growing and selection would be repeated any number of times until a homozygous wheat variety with one or more non-transgenic mutations in the Lpx1 gene-derived wheat plant is obtained. The homozygous wheat variety with one or more non-transgenic mutations in the Lpx1 gene-derived wheat plant would contain desirable traits derived from wheat variety with one or more non-transgenic mutations in the Lpx genes, some of which may not have been expressed by the other original wheat variety to which wheat variety with one or more non-transgenic mutations in the Lpx1 gene was crossed and some of which may have been expressed by both wheat varieties but now would be at a level equal to or greater than the level expressed in wheat variety with one or more non-transgenic mutations in the Lpx1 gene or genes.

The breeding process, of crossing, selfing, and selection may be repeated to produce another population of wheat variety with one or more non-transgenic mutations in the Lpx1 gene-derived wheat plants with, on average, 25% of their genes derived from wheat variety with one or more non-transgenic mutations in the Lpx1 gene, but various individual plants from the population would have a much greater percentage of their alleles derived from wheat variety with one or more non-transgenic mutations in the Lpx1 gene or genes. Another embodiment of the invention is a homozygous wheat variety with one or more non-transgenic mutations in the Lpx gene-derived wheat plant that has received wheat variety with one or more non-transgenic mutations in the Lpx gene-derived traits. This breeding process can be repeated as many times as desired.

The following paragraphs further describe plants, compositions, and methods disclosed herein.

1. A wheat plant comprising a mutation in the Lpx1 gene, wherein said mutation contributes to products from said wheat plant having increased shelf-life compared to products from a wild type wheat plant.

2. A wheat plant comprising a mutation in the Lpx1 gene, wherein said mutation contributes to reduced hexanal production in products produced from grain from said plant as compared to products produced from grain from a wild type wheat plant.

3. The wheat plant of paragraphs 1 or 2, further comprising a mutation in at least two genomes.

4. The wheat plant of paragraphs 1 or 2, further comprising a reduced level of Lpx1 protein, relative to a wild-type wheat plant.

5. The wheat plant of paragraphs 1 or 2, further comprising reduced Lpx1 enzyme activity relative to a wild-type wheat plant.

6. The wheat plant of paragraphs 1 or 2, wherein products from said wheat plant have increased oxidative stability as compared to products from a wild type wheat plant.

7. A wheat plant comprising a mutation in the Lpx1 gene in the D genome, wherein said mutation contributes to products from said wheat plant having increased shelf-life compared to products from a wild type wheat plant.

8. A wheat plant comprising a mutation in the Lpx1 gene in the D genome, wherein said mutation contributes to reduced hexanal production in products from grain from said plant as compared to products produced from grain from a wild type wheat plant.

9. The wheat plant of paragraphs 7 or 8, wherein the Lpx1 gene is Lpx-D1.

10. The wheat plant of paragraphs 7 or 8, further comprising a mutation in the Lpx1 gene of the B genome.

11. The wheat plant of paragraphs 7 or 8, further comprising a reduced level of Lpx1 protein, relative to a wild-type wheat plant.

12. The wheat plant of paragraphs 7 or 8, further comprising reduced Lpx1 enzyme activity relative to a wild-type wheat plant.

13. The wheat plant of paragraphs 7 or 8, wherein products from said wheat plant have increased oxidative stability as compared to products from a wild type wheat plant.

14. A wheat plant comprising a mutation in the Lpx1 gene in the B genome, wherein said mutation contributes to products from said wheat plant having increased shelf-life compared to products from a wild type wheat plant.

15. A wheat plant comprising a mutation in the Lpx1 gene in the B genome, wherein said mutation contributes to reduced hexanal production in products from grain from said plant as compared to products from grain from a wild type wheat plant.

16. The wheat plant of paragraphs 14 or 15, wherein the Lpx1 gene is Lpx-B1.2.

17. A wheat plant of paragraphs 14 or 15 further comprising a mutation in the Lpx1 gene of the D genome.

18. The wheat plant of paragraphs 14 or 15, further comprising a reduced level of Lpx1 protein, relative to a wild-type wheat plant.

19. The wheat plant of paragraphs 14 or 15, further comprising reduced Lpx1 enzyme activity relative to a wild-type wheat plant.

20. The wheat plant of paragraphs 14 or 15, wherein products from said wheat plant have increased oxidative stability as compared to products from a wild type wheat plant.

21. The wheat plant of any of the preceding paragraphs where the wheat plant is homozygous for the mutation.

22. The wheat plant of any of the preceding paragraphs, which is *Triticum aestivum* ssp. *aestivum*.

23. A wheat plant comprising two or more mutations in the Lpx gene, wherein the mutations in the Lpx gene are on at least two different genomes.

24. Whole grain flour from grain from the wheat plant of any of the preceding paragraphs, wherein the production of decomposition products of fatty acids is decreased in whole grain flour as compared to whole grain flour made from wild type grain.

25. Whole grain flour from grain from the wheat plant of any of the preceding paragraphs, wherein the production of decomposition products of fatty acids is decreased in whole grain flour by at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95% as compared to whole grain flour made from wild type grain.

26. Whole grain flour from the wheat plant of any of the preceding paragraphs, wherein the production of hexanal, or trans-2-nonenal, or trihydroxydecanoic acid or combinations thereof is decreased in whole grain flour by at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95% as compared to whole grain flour made from wild type grain.

27. Whole grain flour from the grain of the wheat plant of any of the preceding paragraphs, wherein shelf life of whole grain flour is increased by 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, or greater than 30 months as compared to the shelf life of whole grain flouor made from wild-type grain.

28. Whole grain flour from grain comprising a mutation in an Lpx1 gene, wherein said mutation contributes to reduced hexanal production in whole grain flour as compared to whole grain flour from a wild type wheat plant.

29. Whole grain flour comprising a mutation in an Lpx1 gene, wherein said mutation contributes to increased shelf-life in whole grain flour as compared to whole grain flour from a wild type wheat plant.

30. Whole grain flour comprising a mutation in an Lpx1 gene, wherein said mutation contributes to increased shelf-life in whole grain flour stored at a higher temperature as compared to whole grain flour from a wild type wheat plant.

31. Whole grain flour from the wheat plant of any of the preceding paragraphs, wherein shelf life of whole grain flour made from wheat grain is improved as determined by sensory characteristics including color, flavor, texture, aroma, performance or overall preference of the finished product.

32. The wheat plant of any of the preceding claims, wherein the mutation is recited in any one of Tables 1-10.

33. Wheat grain from a wheat plant of any of the preceding paragraphs.

34. Flour comprising wheat grain of any of the preceding paragraphs.

35. A food product comprising a component of a wheat plant of any of the preceding paragraphs.

36. A wheat seed, plant part or progeny thereof from a wheat plant of any of the preceding paragraphs.

37. A wheat plant substantially as shown and described herein.

38. Grain substantially as shown and described herein.

39. Wheat seed, plant part or progeny thereof from a wheat plant substantially as shown and described herein.

40. A wheat plant comprising one or more mutations in the Lpx1 gene in one or both of the B and D genomes, wherein milled grain from said wheat plant has a property selected from the group consisting of: (a) increased shelf-life; (b) increased oxidative stability; (c) decreased production of Lpx1 protein; (d) decreased activity of the Lpx1 protein; (e) decreased hexanal production; (f) decreased pinellic acid production; (g) decreased decomposition products from fatty acids; or (h) improved sensory characteristics as compared to milled grain from a wild type wheat plant.

41. A wheat plant comprising one or more mutations in the Lpx1 gene in one or both of the B and D genomes, wherein products produced from grain from said wheat plant has a property selected from the group consisting of: (a) increased shelf-life; (b) increased oxidative stability; (c) decreased production of Lpx1 protein; (d) decreased activity of the Lpx1 protein; (e) decreased hexanal production; (0 decreased pinellic acid production; (g) decreased decomposition products from fatty acids; or (h) improved sensory characteristics as compared to products produced from grain of a wild type wheat plant.

42. A nucleic acid comprising a coding sequence that encodes a polypeptide having at least one mutation recited in Table 2 of SEQ ID NO:3.

43. A nucleic acid comprising a coding sequence having at least one mutation in Table 2 of SEQ ID NO. 1 or SEQ ID NO. 2.

44. A nucleic acid comprising a coding sequence that encodes a polypeptide having at least one mutation recited in Table 1 of SEQ ID NO:6.

45. A nucleic acid comprising a coding sequence having at least one mutation in Table 1 of SEQ ID NO. 4 or SEQ ID NO. 5.

Example 1

This example describes the identification of novel alleles of Lpx1.

Mutagenesis

In accordance with one exemplary embodiment of the present invention, wheat seeds of the hexaploid cultivar (*Triticum aestivum*) Express were vacuum infiltrated in $H_2O$ (approximately 1,000 seeds/100 ml $H_2O$ for approximately 4 minutes). The seeds were then placed on a shaker (45 rpm) in a fume hood at room temperature. The mutagen ethyl methanesulfonate (EMS) was added to the imbibing seeds to final concentrations ranging from about 0.75% to about 1.2% (v/v). Following an 18-hour incubation period, the EMS solution was replaced 4 times with fresh $H_2O$. The seeds were then rinsed under running water for about 4-8 hours. Finally, the mutagenized seeds were planted (96/tray) in potting soil and allowed to germinate indoors. Plants that were four to six weeks old were transferred to the field to grow to fully mature M1 plants. The mature M1 plants were allowed to self-pollinate and then seeds from the M1 plant were collected and planted to produce M2 plants.

A. DNA Preparation

DNA from the M2 plants produced in accordance with the above description was extracted and prepared in order to identify which M2 plants carried a mutation at one or more of their Lpx1 loci. The M2 plant DNA was prepared using methods and reagents based on the Qiagen® (Valencia, Calif.) DNeasy® 96 Plant Kit. Approximately 50 mg of frozen plant sample was placed in each sample tube with a stainless steel bead, frozen in liquid nitrogen and ground 2 times for 45 seconds each at 21.5 Hz using the Retsch® Mixer Mill MM 300. Next, 300 μl of solution AP1 [Buffer AP1, solution DX and RNAse (100 mg/ml)] at 80° C. was added to each sample. The tubes were sealed and shaken for 15 seconds, then briefly centrifuged at 5,200×g. Following the addition of 100 μl Buffer P3, the tubes were shaken for 15 seconds. The samples were placed in a freezer at −20° C. for at least 20 min. The samples were then centrifuged for 20 minutes at 5,200×g. A filter plate was placed on the vacuum unit of Tecan Evo liquid handling robot and 400 μl of Buffer AW1 was added to each well. Following the addition of a 300 μl aliquot of supernatant to each well, vacuum was applied until dryness. Next, 650 μl of Buffer AW2 was added to each well of the filter plate. The filter plate was placed on a square well block and centrifuged for 20 minutes at 5,200×g. The filter plate was then placed on a new set of sample tubes and 90 μl of Buffer AE was applied to the filter. It was incubated at room temperature for 1 minute and then spun for 2 minutes at 5,200×g. This step was repeated with an additional 90 μl Buffer AE. The filter plate was removed and the tubes containing the pooled filtrates were capped. The individual samples were then normalized to a DNA concentration of 5 to 10 ng/μl for TILLING, or left un-normalized for genotyping applications.

B. Tilling

The M2 wheat DNA was pooled into groups of two individual plants. The DNA concentration for each individual within the pool was approximately 2 ng/μl with a final concentration of 4 ng/μl for the entire pool. Then, 5 μl of the pooled DNA samples (or 20 ng wheat DNA) was arrayed on microtiter plates and subjected to gene-specific PCR.

PCR amplification was performed in 15 μl volumes containing 20 ng pooled DNA, 0.75×ExTaq buffer (Clonetech, Mountain View, Calif.), 1.1 mM additional $MgCl_2$, 0.3 mM dNTPs, 0.3 μM primers, 0.009 U Ex-Taq DNA polymerase (Clonetech, Mountain View, Calif.), 0.02 units DyNAzyme II DNA Polymerase (Thermo Scientific), and if necessary 0.33M Polymer-Aide PCR Enhancer (Sigma-Aldrich®). PCR amplification was performed using an MJ Research® thermal cycler as follows: 95° C. for 2 minutes; 8 cycles of "touchdown PCR" (94° C. for 20 second, followed by annealing step starting at 70-68° C. for 30 seconds and decreasing 1° C. per cycle, then a temperature ramp of 0.5° C. per second to 72° C. followed by 72° C. for 1 minute); 25-45 cycles of 94° C. for 20 seconds, 63 or 65° C. for 30 seconds, ramp 0.5° C./sec to 72° C., 72° C. for 1-2 minutes; 72° C. for 8 minutes; 98° C. for 8 minutes; 80° C. for 20 seconds; 60 cycles of 80° C. for 7 seconds −0.3 degrees/cycle.

PCR products (2-4 μl) were digested in 96-well plates. 3 μl of a solution containing 6 mM HEPES [4-(2-hydroxyethyl)-1-piperazineethanesulfonic acid] (pH 7.0), 6 mM $MgCl_2$, 6 mM NaCl, 0.012× Triton® X-100, 0.03 mg/ml of bovine serum albumin, 0.5× T-Digest Buffer [Advanced Analytical Technologies, Inc (AATI), Ames, Iowa], 0.912 U each of Surveyor® Endonuclease and Enhancer (Transgenomic®, Inc.), and 0.5×dsDNA Cleavage Enzyme (AATI, Ames, Iowa) was added to the PCR product. Digestion reactions were incubated at 45° C. for 45 minutes. The specific activity of the Surveyor enzyme was 800 units/μl, where a unit was defined by the manufacturer as the amount of enzyme required to produce 1 ng of acid-soluble material from sheared, heat denatured calf thymus DNA at pH 8.5 in one minute at 37° C. Reactions were stopped by addition of 20 μl of Dilution Buffer E (AATI, Ames, Iowa) or 1×TE. The reactions were stored in the freezer until they were run on the Fragment Analyzer™ (AATI, Ames, Iowa) Capillary Electrophoresis System. Samples were run on the Fragment Analyzer™ utilizing the DNF-920-K1000T Mutation Discovery Kit (AATI, Ames, Iowa) according to the manufacturer's protocol.

After electrophoresis, the assays were analyzed using PROSize® 2.0 Software (AATI, Ames, Iowa). The gel image showed sequence-specific pattern of background bands common to all 96 lanes. Rare events, such as mutations, create new bands that stand out above the background pattern. Plants with bands indicative of mutations of interest were evaluated by TILLING individual members of a pool mixed with wild type DNA and then sequencing individual PCR products.

Example 2: Genotyping and Plant Breeding of Lpx1 Lines

Plants carrying mutations confirmed by sequencing were grown up as described above (e.g., the M2 plant could be backcrossed or outcrossed multiple times in order to eliminate background mutations and self-pollinated in order to create a plant that was homozygous for the mutation) or crossed to another plant containing Lpx1 mutations in a different homoeolog. At each generation, the novel alleles were validated in the plant materials by extracting DNA, and genotyped by sequencing or by use of allele specific KASP (Kompetitive Allele Specific PCR) molecular markers (LGC Genomics, Beverly, Mass.) developed specifically for alleles of interest.

KASP genotyping was performed on DNA extracted from young leaves as describe in Example 1. Each reaction consisted of 5 μl master mix (KASP High-Rox Universal 2× Master Mix, LGC Genomics) 0.14 μl KASP Assay Mix, and 40-60 ng DNA in a total reaction volume of 10.14 μl. The reaction mixture was then PCR amplified in a 96-well format using the following thermal cycling conditions: 94° C. for 15 minutes, then 10 cycles at 92° C. for 20 seconds followed by 61° C. for 60 seconds dropping 0.6° C. per cycle until reaching 55° C., then 35-40 cycles of 94° C. for 20 seconds followed by 55° C. for 60 seconds, and finally held at 8° C. until measurement. The subsequent reaction was evaluated at room temperature with a 7900 HT Fast Real-Time PCR system using controls of known genotypes (Applied Biosystems, Inc, Foster City, Ca, USA).

Example 3: Lipoxygenase Activity

Lipoxygenase activity in mature whole grains was measured by either of two methods: (a) conjugated diene formation or (b) colorimetric assay.

A. Method 1: Lipoxygenase Enzyme Activity by Conjugated Diene Formation

For conjugated diene analysis, total lipoxygenase activity in whole grain wheat flour was measured spectrophotometrically as described by Surrey, *Plant Physiology* 39: 65-70, (1964). The assay determines the formation of linoleate hydroperoxide containing conjugated dienes at 25° C. measured at 234 nm using a NanoDrop 2000c Spectrophotometer (Thermo Scientific, Waltham, Mass., USA). Whole grain flour was milled from mature seeds for 20 sec at 22 1/s vibration frequency using a MixerMill 300 (Retsch GmbH, Haan, Germany). 200 mg of whole grain flour was suspended in 1.5 mL of 50 mM sodium phosphate buffer (pH 6.6). The suspension was incubated in an ice-water bath for 1 hour, vortexed for 1 min at 15 min intervals, and centrifuged twice at 16,100×g at 4° C. for a total of 20 min. After centrifugation, the supernatant was collected as the crude enzyme solution, stored in an ice-water bath, and used within 12 hours. Protein concentration was determined according to the Bradford method (Bio-Rad, Hercules, Calif., USA) using bovine serum albumin as the standard according to the manufacturer's instructions. Linoleate substrate solution consisted of 50 mM sodium phosphate buffer pH 6.6, 2 mM linoleic acid >99% (Sigma Chemical, St Louis, Mo., USA), and 0.2% Tween20 (Bio-Rad, Hercules, Calif., USA), and was stored in an air tight container containing 5-7 oxygen scavenging packets (Oxyrase, Mansfield, Ohio, USA) to minimize auto-oxidation of substrate. Linoleate hydroperoxidation reaction was started by the addition of 0.1 mg of crude enzyme solution into 2 mL of linoleate substrate solution at 25° C. The reaction was monitored from 0 to at least 3 minutes. Results were subjected to statistical analysis by ANOVA followed by t-tests using InStat Software (GraphPad, La Jolla, Calif., USA). One unit of Lipoxygenase activity was defined as the increase in absorbance at 234 nm of 0.001 per mg of protein per minute. Negative controls of the samples were prepared by inactivating the crude enzymes by heat treatment at 100° C. for 20 min.

B. Method 2: Lipoxygenase Activity by Colorimetric Assay

Total lipoxygenase activity in whole grain wheat flour was also measured using a modified colorimetric assay using the coupled reaction of 3-(di-methylamino)benzoic acid (DMAB) and 3-methyl-2-benzothiazolinone (MBTH) as described by Anton and Barret, *Journal of Agriculture Food Chemistry* 49: 32-37, (2001). The assay determines the product formation of linoleate hydroperoxides with MBTH and DMAB in the presence of hemoglobin. Whole grain flour was milled from mature seeds for 20 seconds at 22 1/s vibration frequency using a MixerMill 300 (Retsch GmbH, Haan, Germany). 200 mg of whole grain flour was suspended in 1.5 mL of 50 mM sodium phosphate buffer (pH 6.6). The suspension was incubated in an ice-water bath for 1 hour, vortexed for 1 min at 15 minute intervals, and centrifuged twice at 16,100×g at 4° C. for a total of 20 minutes. After centrifugation, the supernatant was collected as the crude enzyme solution, stored in an ice-water bath, and used within 12 hours. Protein concentration was determined according to the Bradford method (Bio-Rad, Hercules, Calif., USA) using bovine serum albumin as the standard according to the manufacturer's instructions. DMAB-linoleate substrate solution consisted of 20 mM DMAB and 100 µM sodium phosphate (pH 6.6) with 25 mM linoleic acid >99% and 0.1% Tween20. MBTH-hemoglobin solution consisted of 10 mM MBTH and 0.1 mg/mL bovine hemoglobin (Sigma Chemical, St Louis, Mo., USA).

The linoleate hyroperoxidation/DMAB-MBTH coupling reaction was started by adding 0.5 ml of the DMAB-linoleate substrate solution to 0.1 mg crude enzyme and incubated at 25° C. for 20 minutes. After 20 minutes, 0.5 ml of the MBTH-hemoglobin solution was then added and incubated for an additional 10 minutes. The reaction was terminated by adding 0.5 ml of 1% (w/v) sodium dodecyl sulfate (SDS). Color formation at an absorbance value of 595 nm was measured using a NanoDrop 2000c Spectrophotometer (Thermo Scientific, Waltham, Mass., USA). Results were subjected to statistical analysis using InStat Software (GraphPad, La Jolla, Calif., USA). One unit of lipoxygenase activity was defined as the absorbance value at 595 nm per mg of protein times 100. Negative controls of the samples were prepared by inactivating the crude enzymes by heat treatment at 100° C. for 20 min.

Grains from homozygous wheat plants with mutations in either Lpx-D1 or LpxB1.2 of the D or B genome or both genomes were analyzed for lipoxygenase activity. In addition, selected plants identified with severe mutations in Lpx1 of the B or D genome (Tables 1 and 2) were crossed with other plants that contained severe mutations in Lpx1 in other genomes. Grains from homozygous plants resulting from these crosses having novel mutant alleles in both genomes were also analyzed for lipoxygenase activity. Sibling plants from these crosses with wild-type alleles for the Lpx1 mutations were used as controls when they were available. Mutant alleles analyzed for lipoxygenase activity included missense mutations that were predicted to have a deleterious effect on protein function by their SIFT and PSSM scores, as well as those mutations that resulted in the introduction of a stop codon (truncation mutation) or a mutation at a splice junction. Table 5 shows examples of mutant lines analyzed for lipoxygenase activity.

TABLE 5

Representative cultivars with mutations in Lpx-D1 and/or Lpx-B1.2

| Line | Gene | Nucleotide Mutation | A.A. Mutation |
|---|---|---|---|
| 1 | Lpx-D1 | G626A | W81* |
| 2 | Lpx-D1 | G685A | W101* |
| 3 | Lpx-D1 | C1471T | P170S |
| 4 | Lpx-D1 | G1646A | R228H |
| 5 | Lpx-D1 | C1531T | Q190* |
| 6 | Lpx-D1 | C1633T | P224S |
| 7 | Lpx-D1 | G2386A | Splice Junction |
| 8 | Lpx-D1 | C2553T | P469L |
| 9 | Lpx-D1 | G2629A | W494* |
| 10 | Lpx-D1 | G2828A | W517* |
| 11 | Lpx-D1 | G2875A | R533Q |
| 12 | Lpx-D1 | C2895T | P540S |
| 13 | Lpx-D1 | C2919T | H548Y |
| 14 | Lpx-D1 | G3049 | W591* |
| 15 | Lpx-D1 | G3181A | W635* |
| 16 | Lpx-D1 | G3272A | W665* |
| 17 | Lpx-D1 | G3275A | W666* |
| 18 | Lpx-D1 | G3364A | C696Y |
| 19 | Lpx-D1 | G3379A | W701* |
| 20 | Lpx-D1 | G3644A | W789* |
| 21 | Lpx-B1.2 | G2982A | W510* |
| 22 | Lpx-D1 | G2629A | W494* |
|  | Lpx-B1.2 | G2982A | W510* |
| 23 | Lpx-D1 | C2528T | P461S |
|  | Lpx-B1.2 | G2933A | W494* |

With regard to Tables 5-7, genomic nucleic acid designations of the mutations in Lpx1 of the D genome named Lpx-D1 correspond to the position in the reference sequence SEQ ID NO: 1. Amino acid designations of the Lpx1 polypeptide of the D genome named Lpx-D1 correspond to the amino acid position of reference sequence SEQ ID NO: 3. Genomic nucleic acid designations of the mutations in one of two of Lpx1 genes of the B genome named Lpx-B1.2 correspond to the position in the reference sequence SEQ ID NO: 4. Amino acid designations of the mutations in one of two of Lpx1 genes of the B genome named Lpx-B1.2 correspond to the amino acid position of reference sequence SEQ ID NO: 6. "Wt" indicates material that is homozygous for the parental wild-type allele and "homozygous" refers to material that is homozygous for the mutant allele indicated.

TABLE 6

Lipoxygenase Activity of Novel Alleles of Lpx1 in Wheat Variety Express.

| Line | Gene | Nucleotide Mutation | A.A. Mutation | Zygosity of Mutation | Lipoxygenase Activity Colorimetric Assay (Units/mg protein) | Lipoxygenase Activity Conjugated Diene Assay (Units/min/mg) |
|---|---|---|---|---|---|---|
| Parent Express | Lpx-D1 + Lpx-B1.2 | Wt | None | Wt | 1915 +/− 29 | 1231 +/− 62 |
| 1 | Lpx-D1 | G626A | W81* | Homozygous | 709 +/− 47 | |
| 2 | Lpx-D1 | G685A | W101* | Homozygous | 593 +/− 63 | |
| 3 | Lpx-D1 | C1471T | P170S | Homozygous | 1912 +/− 25 | |
| 4 | Lpx-D1 | C1531T | Q190* | Homozygous | 1039 +/− 40 | |
| 5 | Lpx-D1 | G1646A | R228H | Homozygous | 1879 +/− 29 | |
| 6 | Lpx-D1 | C1633T | P224S | Homozygous | 1873 +/− 18 | |
| 7 | Lpx-D1 | G2386A | Splice Junction | Homozygous | 358 +/− 21 | |
| 8 | Lpx-D1 | C2553T | P469L | Homozygous | 1883 +/− 18 | |
| 9 | Lpx-D1 | G2629A | W494* | Homozygous | 502 +/− 7 | 33 +/− 26 |
| 10 | Lpx-D1 | G2828A | W517* | Homozygous | 401 +/− 2 | 80 +/− 32 |
| 11 | Lpx-D1 | G2875A | R533Q | Homozygous | 1690 +/− 66 | 476 +/− 56 |
| 12 | Lpx-D1 | C2895T | P540S | Homozygous | 1418 +/− 44 | 427 +/− 13 |
| 13 | Lpx-D1 | C2919T | H548Y | Homozygous | 1763 +/− 3 | |
| 14 | Lpx-D1 | G3049A | W591* | Homozygous | 707 +/− 90 | |
| 15 | Lpx-D1 | G3181A | W635* | Homozygous | 866 +/− 68 | |
| 16 | Lpx-D1 | G3272A | W665* | Homozygous | 681 +/− 56 | |
| 17 | Lpx-D1 | G3275A | W666* | Homozygous | 1441 +/− 41 | |
| 18 | Lpx-D1 | G3364A | C696Y | Homozygous | 1304 +/− 61 | |
| 19 | Lpx-D1 | G3379A | W701* | Homozygous | 681 +/− 160 | |
| 20 | Lpx-D1 | G1646A + G3644A | R228H + W789* | Both Homozygous | 799 +/− 10 | |
| 21 | Lpx-B1.2 | G2982A | W510* | Homozygous | 1860 +/− 40 | 798 +/− 105 |
| 22 | LpxD1 + Lpx-B1.2 | G2629A + G2982A G2629G + G2982G | W494* + W510* W494W + W510W | Homozygous Wt Sibling | 387 +/− 2 1914 +/− 2 | |
| 23 | Lpx-D1 + Lpx-B1.2 | C2528T + G2933A | P461S + W494* | Both Homozygous | 1912 +/− 2 | 853 +/− 109 |

Table 6 demonstrates the range of lipoxygenase activity of various lines with novel alleles in the Lpx-D1 gene, the Lpx-B1.2 gene or combinations of the two.

TABLE 7

Lipoxygenase Activity of Various Varieties of Wheat. Activity is expressed in Units/mg protein using the colorimetric assay (+/− standard error).

| Wheat Variety | Type | D Genome | B Genome | B Genome | A Genome | Lipoxygenase Activity |
|---|---|---|---|---|---|---|
| California | HRS | Lpx-D1 | Lpx-B1.1c | Lpx-B1.2 | Lpx-A1 | 1915 +/− 29 |
| Mexico | HWS | Lpx-D1 | Lpx-B1.1c | Lpx-B1.2 | Lpx-A1 | 2024 +/− 38 |
| Mexico | HWS | Lpx-D1 | Lpx-B1.1c | Lpx-B1.2 | Lpx-A1 | 1863 +/− 61 |
| Colorado | HWW | Lpx-D1 | Lpx-B1.1c | Lpx-B1.2 | Lpx-A1 | 2032 +/− 32 |
| Colorado | HWW | Lpx-D1 | Lpx-B1.1c | Lpx-B1.2 | Lpx-A1 | 2020 +/− 18 |
| Midwest | HRS | Lpx-D1 | Lpx-B1.1a or b | Lpx-B1.2 | Lpx-A1 | 1935 +/− 79 |
| Midwest | HRS | Lpx-D1 | Lpx-B1.1a or b | Lpx-B1.2 | Lpx-A1 | 1955 +/− 15 |
| Pacific Northwest | HRS | Lpx-D1 | Lpx-B1.1c | Lpx-B1.2 | Lpx-A1 | 1958 +/− 50 |
| Pacific Northwest | SWS | Lpx-D1 | Lpx-B1.1a or b | Lpx-B1.3 | Lpx-A1 | 1960 +/− 15 |
| Australia | SWS | Lpx-D1 | Lpx-B1.1c | Lpx-B1.2 | Lpx-A1 | 2051 +/− 23 |
| Australia | SWS | Lpx-D1 | Lpx-B1.1c | Lpx-B1.2 | Lpx-A1 | 1973 +/− 17 |

Key:
HRS, hard red spring,
HWW, hard white winter,
SWS, soft white spring,
HWS, hard white spring Table 7 demonstrates the range of lipoxygenase activity achieved in various combinations of novel alleles in the Lpx-D1 gene, the Lpx-B1.2 gene and combinations of the two. Table 7 further demonstrates that despite the range of different allele combinations available in the Lpx-B genes in multiple varieties of bread wheat, all the varieties tested still have a high level of lipoxygenase activity in mature grains. Evaluation of numerous additional varieties from multiple regions around the world has shown the same result.

Example 4

Improved Shelf Life by Sensory Characteristics of Lpx1 Novel Alleles

Shelf life can be determined by sensory characteristics of the flour and products made from it including color, flavor, texture, aroma, appearance, performance or overall preference of the finished product. In one embodiment, trained panelists can be used to assess differences between materials.

For example, Lpx1 flour can be stored for various lengths of time, at various temperatures and/or humidities and compared to the wild-type sibling flour and/or parental flour by the panelists for preference in aroma, color, flavor, appearance and texture among other attributes. The flour can also be made into products, such as bread, and the crumb and crust compared for in aroma, color, flavor, appearance or texture among other attributes. Bread or other products can also be stored for various lengths of time, at various temperatures and/or humidities and compared to the wild-type sibling flour and/or parental flour by the panelists for preference in in aroma, color, flavor, appearance or texture among other attributes.

Other methods can also be employed to assess sensory characteristics. For example, texture can be measured by a texture analyzer. Color can be measured by a Minolta chroma meter test. Compounds contributing to aroma or taste can be analyzed by liquid or gas chromatography and mass spectrometry.

Example 5: Improved Shelf-Life of Lpx1 Novel Alleles

Lipid oxidation by lipoxygenase produces hydroperoxides that are substrates for further decomposition into multiple compounds including aldehydes such as hexanal. Hexanal levels produced in a sample can be used as a measure of oxidative rancidity (Fritz and Gale, Hexanal as a measure of rancidity in low fat foods, *JAOCS* 54:225 (1977)). In order to test shelf-life of whole grain flour derived from grain of novel lipoxygenase mutant alleles, whole grain samples were milled and stored for various lengths of time up to 20 weeks at 37° C. and analyzed for hexanal levels as described below. Longer incubation times and a range of additional temperature and humidity conditions can also be employed for testing shelf life.
Methods: Hexanal Analysis Whole grain flour was milled from mature seeds for 20 seconds at 22 1/s vibration frequency using a MixerMill 300 (Retsch GmbH, Haan, Germany) and stored in closed polyethylene bags. Accelerated aging of flour was conducted in a Percival E30BC8 (Percival Scientific Inc, Perry, Iowa, USA) with the temperature set at 37° C. 10 g samples of flour were stored for 1-16 weeks at 37° C. Hexanal levels were analyzed by Medallion Labs (Minneapolis, Minn., USA) using a method based on gas chromatography. Units were reported in parts per million (ppm) with a lower detection limit of <0.3 ppm and an upper limit of detection of 50 ppm.

An accelerated aging time-course of whole grain flour incubated at 37° C. for up to 20 weeks was evaluated for hexanal production as an indicator of rancidity. Flour from the non-mutagenized parental variety, Express, was tested at 1, 6, 8, 10, 16 and 20 weeks after incubation at 37° C. and compared to hexanal levels in freshly milled flour samples.

As shown in FIG. 1, hexanal levels were below the limit of detection of <0.3 ppm in freshly ground and 1 week old samples. But starting at the 6 week time point and continuing to 20 weeks, hexanal levels increased from 0.6 ppm up to 1 ppm demonstrating the progression of oxidative rancidity. For cereals, a 16 week incubation time at 37° C. is estimated to be equivalent to approximately 1 year of storage at room temperature (Sewald and DeVries, Food product shelf life, Medallion Laboratories Analytical Progress (2012) http://www.medlabs.com/Downloads/food_product_shelf_life_web.pdf).

Wheat line 9 (Table 6) homozygous for the Lpx-D1 (W494*) allele and wheat line 22 (Table 6) homozygous for both the Lpx-D1(W494*) and Lpx-B1.2(W510*) alleles were tested for hexanal production in whole grain flour stored at 37° C. for up to 16 weeks. In addition, sibling lines that were homozygous wild-type for these alleles and were grown at the same time were used as controls (wild-type siblings). Grains were bulked from 2-6 plants of the same genotype to provide enough material for analysis over the entire time-course.

Figure 2:
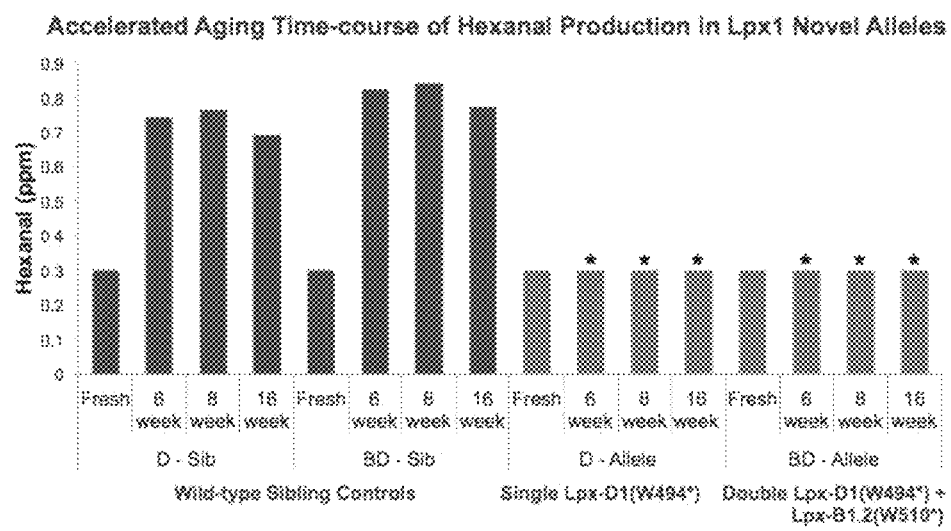
FIG. 2 is a bar graph showing the improved shelf life of novel Lpx-D1 and Lpx-B1.2×Lpx-D1 alleles during an accelerated aging time course at 37° C.

As shown in FIG. 2, hexanal levels increased at 6, 8 and 16 weeks of incubation at 37° C. in wild-type siblings. This result was similar to hexanal production in the parental material (FIG. 1). In contrast, hexanal levels remained below the limit of detection of <0.3 ppm in the whole grain flour samples from lines homozygous for the Lpx-D1(W494*) mutant allele and in lines homozygous for both the Lpx-D1 (W494*)+LpxB1.2(W510*) mutant alleles for up to 16 weeks at 37° C. (asterisks in FIG. 2). The disclosure herein demonstrates that novel alleles in Lpx-D1 with reduced lipoxygenase activity singly and in combination with novel alleles in Lpx-B1.2 significantly improve shelf-life of whole grain flour by reducing the accumulation of breakdown products of fatty acids such as hexanal. Additional alleles of Lpx1 can also be used to improve shelf life.

Example 6

Altered Lipoxygenase Activity of Wheat Lines with Lpx-D1 Promoter Alleles

Table 8 provides additional examples of mutations created and identified in Lpx-D1 promoter in the D genome of wheat plants, variety Express. Nucleotide changes are identified according to their positions in SEQ ID NO: 15. Zygosity refers to whether the mutation is heterozygous (Het) or homozygous (Hom) in the M2 plant.

TABLE 8

Additional representative mutations in
the Lpx-D1 promoter in the D genome.

| Primer SEQ IDs | Nucleotide Mutation (SEQ ID NO: 15) | Description | Zygosity of Mutation |
|---|---|---|---|
| 16, 17 | G1269A | 2176F08 | Het |
| 16, 17 | C1276T | 2168C09 | Het |
| 16, 17 | G1474A | 2163B03 | Het |
| 16, 17 | C1779T | 2166F07 | Hom |
| 16, 17 | C1834T | 1686B02 | Hom |

Table 9 demonstrates the range of lipoxygenase activity achieved in wheat lines with novel alleles in the Lpx-D1 promoter region in the D genome. Nucleotide changes of the mutations correspond to the position in the reference sequence SEQ ID NO: 15. "Wt" indicates material that is homozygous for the parental wild-type allele and "homozygous" refers to material that is homozygous for the mutant allele indicated. In Table 9, Line 5 Lpx-D1 promoter allele (G1538A) has reduced lipoxygenase activity compared to the parent variety and other Lpx-D1 promoter alleles.

TABLE 9

Lipoxygenase activity of novel alleles of
Lpx1-D1 promoter in the D genome of wheat

| Line | Gene | Nucleotide Mutation (SEQ ID NO: 15) | Zygosity of Mutation | Lipoxygenase Activity Colorimetric Assay (Units/mg protein) |
|---|---|---|---|---|
| Parent Express | Lpx-D1 Promoter | Wt | Wt | 2045 +/− 34 |
| 1 | Lpx-D1 Promoter | G1269A | Homozygous | 1956 +/− 36 |
|   |   | G1269G | Wt Sibling | 1922 +/− 8.5 |
| 2 | Lpx-D1 Promoter | C1276T | Homozygous | 1941 +/− 17 |
|   |   | C1276C | Wt Sibling | 1935 +/− 18 |
| 3 | Lpx-D1 Promoter | C1339T | Homozygous | 1947 +/− 22 |
| 4 | Lpx-D1 Promoter | G1474A | Homozygous | 2034 +/− 21 |
|   |   | G1474G | Wt Sibling | 2092 +/− 40 |
| 5 | Lpx-D1 Promoter | G1538A | Homozygous | 736 +/− 47 |
| 6 | Lpx-D1 Promoter | C1779T | Homozygous | 1996 +/− 17 |
| 7 | Lpx-D1 Promoter | C1834T | Homozygous | 1957 +/− 36 |
| 8 | Lpx-D1 Promoter | G1966A | Homozygous | 1983 +/− 9 |
|   |   | G1966G | Wt Sibling | 1977 +/− 19 |

Example 7

Improved Shelf-Life of Multiple Lpx-D1 Novel Alleles in 8 Week Accelerated Aging Studies Hexanal is a degradation product of fatty acids that can be used as a measure of oxidative rancidity. Grains from plants with different alleles in Lpx-D1 were tested for hexanal levels after milling and accelerated aging at 37° C. for 8 weeks as described in Example 5. These included single allele wheat lines from Table 5 including Line 1 homozygous for the Lpx-D1(W81*) allele, Line 6 homozygous for the Lpx-D1(P2245) allele, Line 8 homozygous for the Lpx-D1(P469L) allele, Line 9 homozygous for the Lpx-D1 (W494*) allele, Line 7 homozygous for the Lpx-D1(Splice Junction) allele, Line 11 homozygous for the Lpx-D1 (R533Q) allele, Line 12 homozygous for the Lpx-D1 (P540S), Line 15 homozygous for the Lpx-D1(W635*) allele, Line 17 homozygous for the Lpx-D1(W666*) allele, Line 18 homozygous for the Lpx-D1(C696Y) allele and Line 20 homozygous for the Lpx-D1(W789*) allele.

Figure 3:
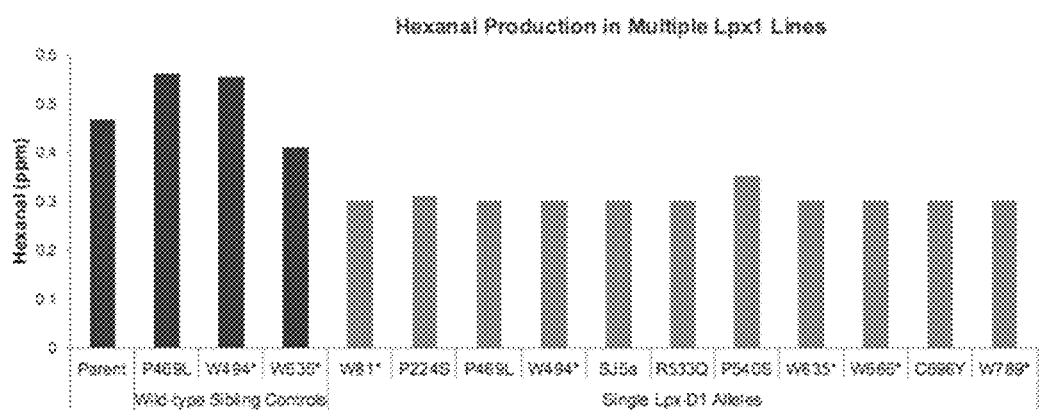
FIG. 3 is a bar graph showing reduced rancidity and improved shelf-life in whole grain flour of multiple Lpx-D1 alleles during an 8 weeks accelerated aging time-course at 37° C.

In addition, grain from the Parent Line Express (Parent) and sibling lines of wheat Lines 8, 9 and 15 that had wild-type alleles were grown at the same time, milled and used as controls (Wild-type Siblings). Hexanal levels were measured at Medallion Labs as described in Example 5. As shown in FIG. 3, the Parent line and Wild-type Siblings lines had elevated levels of hexanal after 8 weeks accelerated aging of whole grain flour, whereas all single homozygous Lpx-D1 lines had reduced hexanal levels. Lines 1, 8, 9, 7, 11, 15, 17, 18 and 20 had hexanal levels below the level of detection (<0.3 ppm), whereas Lines 6 and 12 had slightly elevated hexanal levels of 0.311 and 0.351 ppm.

Figure 4:
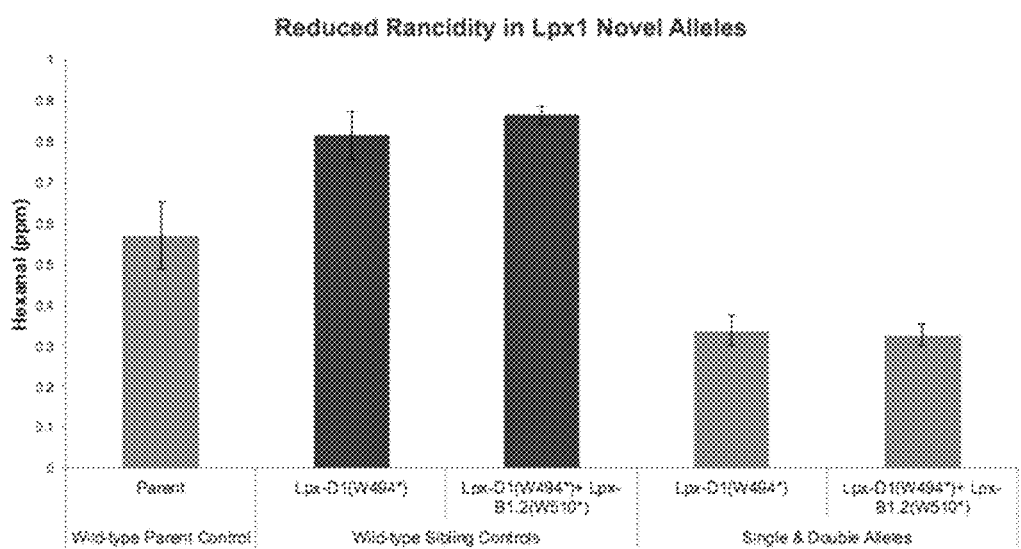
FIG. 4 is a bar graph showing reduced rancidity and improved shelf-life of novel Lpx-D1 and Lpx-B1.2/Lpx-D1 alleles during an 8 weeks accelerated aging time course at 37° C. Triplicate biological replicates were assayed and analyzed for hexanal levels.

In order to further test reduced rancidity and increased shelf-life of whole grain flour derived from grain of novel lipoxygenase mutant alleles, wheat Line 9 (Table 5) homozygous for the Lpx-D1(W494*) allele and wheat Line 22 (Table 5) homozygous for both the Lpx-D1(W494*) and Lpx-B1.2(W510*) alleles were milled as described in Example 5. In addition, sibling lines of wheat Lines 9 or 22 that had homozygous wild-type alleles were milled and used as controls (wild-type siblings). Triplicate biological repeats of whole grain flour were subjected to accelerated aging for 8 weeks and analyzed for hexanal levels as described in Example 5. As shown in FIG. 4, aged grain from plants with homozygous alleles of Line 9 or Line 22 had hexanal levels significantly less than controls (P<0.05), whereas control lines all had increased levels of hexanal.

Example 8

Long Term Reduced Rancidity and Improved Shelf-Life of Lpx1 Novel Alleles Up to the Equivalent of 24 Months at Room Temperature In order to further test reduced rancidity and increased shelf-life of whole grain flour derived from grain of novel lipoxygenase mutant alleles, wheat Line 9 (Table 5) homozygous for the Lpx-D1(W494*) allele and wheat Line 22 (Table 5) homozygous for both the Lpx-D1(W494*) and Lpx-B1.2(W510*) alleles were milled as described in Example 5. In addition, sibling lines of either Lines 9 or 22 that were homozygous wild-type were grown at the same time and then milled and used as controls (wild-type siblings). The whole grain flours were subjected to accelerated aging for 12 or 30 weeks at 37° C., equivalent to an estimated 10 or 24 months at room temperature, respectively. Hexanal levels were measured at Medallion Labs as described in Example 5.

Figure 5:
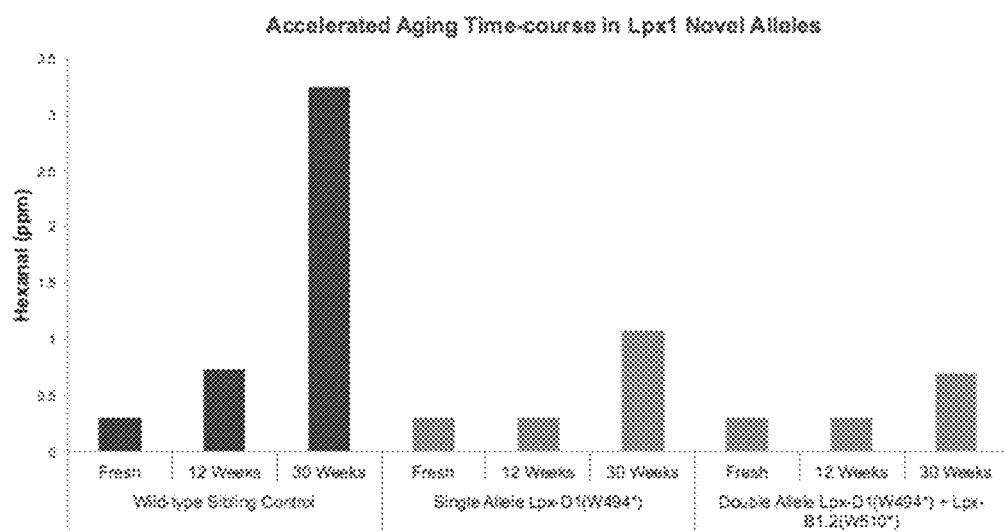
FIG. 5 is a bar graph showing the improved shelf-life of novel Lpx-D1 and Lpx-B1.2×Lpx-D1 alleles during an accelerated aging time-course at 37° C. for 12 and 30 weeks (equivalent to 10 and 24 months at room temperature, respectively).

As shown in FIG. 5, hexanal levels increased to 0.736 ppm in the wild-type sibling aged at 12 weeks. In contrast, hexanal values remained under the limit of detections of <0.3 ppm in wheat Lines 9 and 22 aged at 12 weeks. After 30 weeks of aging, hexanal values of Line 22 wild-type sibling had much higher levels of 3.25 ppm. In even greater contrast, hexanal values of wheat Line 9 aged at 30 weeks only increased to 1.08 ppm and hexanal values of wheat Line 22 aged to 30 weeks only increased to 0.691 ppm. This data demonstrates that novel alleles in Lpx-D1 with reduced lipoxygenase activity singly and in combination with novel alleles in Lpx-B1.2 significantly improve shelf-life of whole grain flour.

Example 9

Reduced Production of Bitter Compound in Milled Whole Grain Flour and Dough Made from Grain of Lpx1 Novel Alleles Oxidative degradation of free linoleic acid in whole wheat flour is the main contributor to the bitter taste in bread crumb (Bin & Peterson, Identification of bitter compounds in whole wheat bread crumb, Food Chemistry, 203:8-15 (2016)). The bitter compound 9,12,13-trihydroxy-trans-10-octadecenoic (pinellic) acid is thought to be a product of substrate epoxidation created during peroxidation by lipoxygenase enzymes (Gardner, Decomposition of linoleic acid hydroperoxides, JOAF 23:129-136 (1975)). To measure the improvement of bitter taste in flour and dough made from grain of novel Lpx1 mutant alleles, whole grain samples were milled and stored for 6 months at 37° C. (equivalent to 19 months at room temperature). Fresh whole grain flour samples were milled immediately prior to analysis. Quantification of 9,12,13-trihydroxy-trans-10-octadecenoic (pinellic) acid in flour and dough was performed using ultra-performance liquid chromatography tandem mass spectrometry (UPLC/MS/MS) at the Flavor Research and Education Center (University of Minnesota).

In a 15 mL reaction volume, 3 g of flour was extracted with an ethanol-chloroform mix (75:25 v/v) spiked with a butyl 4-hydroxybenzoate at 100 mg/mL internal standard. Duplicate reactions were incubated on an orbital shaking table set to 120 rpm for 3 hours followed by centrifugation at 8000 rpm for 15 minutes at 10° C. After centrifugation, the supernatant was carefully separated from the organic phase, pooled in a 250 mL flat bottom flask, and concentrated via rotary evaporation. The residue was re-solubilized in 4 mL of 10% methanol and then subjected to solid phase extraction using a preconditioned 500 mg C18 cartridge (Supelco, Bellefonte, Pa., USA). Each sample was then eluted with 2 mL of methanol and filtered through 0.20 μm Nylon syringe filters (Millex, Billerica, Calif., USA) for further cleanup.

Dough was created by mixing 12 g of flour with 7.2 g of nanopure water and then rested for 20 minutes to ensure adequate formation of pinellic acid. The dough was then divided into thirds by mass and each portion was suspended in 20 mL of 75% (v/v) ethanol solution spiked with a butyl 4-hydroxybenzoate (100 ng/mL) internal standard. The samples were then incubated on an orbital shaking table set to 120 rpm for 3 hours, followed by centrifugation at 8000 rpm for 15 minutes at 10° C. 2 mL of the supernatant was subjected to solid phase extraction using a preconditioned 500 mg C18 cartridge (Supelco, Bellefonte, Pa., USA). Each sample was then eluted with 2 mL of methanol, and the pooled mixture was further diluted with 2 mL of nanopure water to prevent sample breakthrough during mass spectral analysis.

Injections (2 μL) of flour or dough samples were separated on a 2.1 mm×50 mm ACQUITY UPLC BEH C18 1.7 μm column (Waters, Milford, Mass., USA) held at 25° C. MS conditions were as follows: ESI negative, desolvation temperature, 500° C.; source temperature, 120° C.; capillary voltage, 2.7 kV; desolvation gas, 700 L/hr; cone gas, 65 L/hr. UPLC mobile phase was maintained at a flow rate of 300 μL/min using a binary solvent system of (A) 0.1% formic acid in ultrasonicated nanopure water as the aqueous phase, and (B) 0.1% formic acid in acetonitrile for the organic phase. The elution gradient started at 5% B (0-1 min), linearly increased to 50% B (1-6 min), then increased to 100% B (6-8 min) held at 100% B (8-10 min), and re-equilibrated at 5% B (10-15 min). MS/MS ion transitions and collision energy were as follows: 9,12,13trihydroxytrans-10-octadecenoicacid, ESI-329→211 (15 eV); butyl4hydroxybenzoate, ESI-193→136 (15 ev).

Whole grain flour milled from wheat Line 9 (Table 5) homozygous for the Lpx-D1(W494*) allele and a sibling line that was wild-type for the Lpx-D1 allele in Line 9 were aged for 6 months at 37° C. Freshly milled material from these lines was also analyzed. In addition, freshly milled material from wheat Line 22 (Table 5) homozygous for the Lpx-D1(W494*) and Lpx-B1.2(W510*) alleles and a sibling line wild-type for these alleles was also analyzed.

Figure 6:
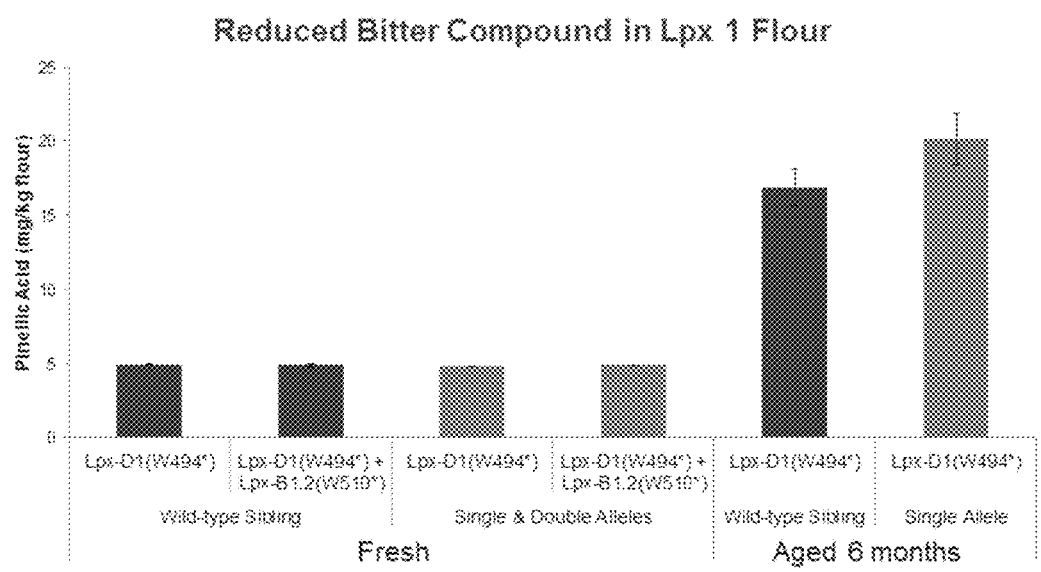
FIG. 6 is a bar graph showing reduced bitter compound, pinellic acid, in aged whole grain flour made from grains with Lpx-D1 novel alleles.

As shown in FIG. 6, fresh milled whole grain flour made from wheat Line 9 and Line 22 and their wild-type siblings had pinellic acid concentrations of around 5 mg/kg flour. In whole grain flour aged for 6 months, pinellic acid levels increased up to 20 mg/kg flour. However, Line 9 had a 15% decrease in pinellic acid formation compared to the wild-type sibling aged for the same length of time. This data shows that novel alleles in Lpx-D1 significantly reduces the production of bitter compounds in aged whole grain flour.

Figure 7:
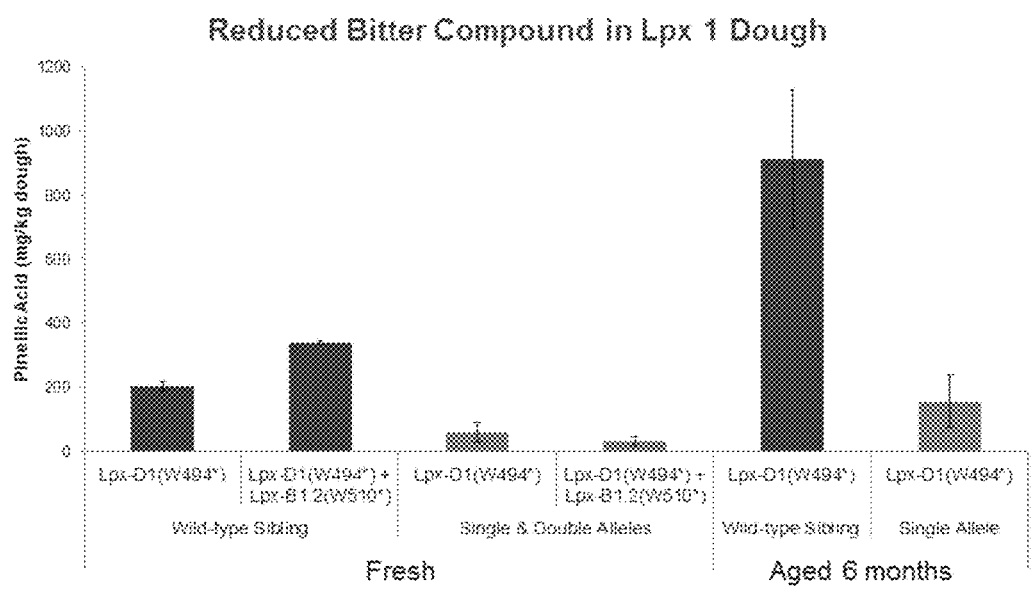
FIG. 7 is a bar graph showing reduced levels of bitter compound, pinellic acid, in dough made from freshly milled or aged whole grain flour from grains with Lpx1 novel alleles.

The effect of Lpx1 novel alleles on bitter compound formation in dough made from whole grain is shown in FIG. 7. Dough made from freshly milled whole grain flour from wheat Line 9 had a low pinellic acid concentration of 60 mg/kg dough compared to the wild-type Line 9 sibling that had over triple the amount of pinellic acid (200 mg/kg dough). Similarly, dough made from freshly milled whole grain flour of Line 22 had a very low pinellic acid concentration of 32 mg/kg dough, while the wild-type Line 22 sibling had over ten times the amount of pinellic acid (340 mg/kg). This data demonstrates that dough made from whole grain flour from wheat with novel alleles in Lpx-D1 and in combination with novel alleles in Lpx-B1.2 significantly reduces the concentration of the major bitter compound found in whole grain products.

Also shown in FIG. 7, dough made from whole grain flour of wheat Line 9 aged for 6 months had significantly reduced pinellic acid concentration (160 mg/kg of dough) compared to the wild-type sibling line had concentration at over six times this amount at 910 mg/kg dough demonstrating improved shelf life of flour containing novel Lpx1 alleles. This data shows that dough made from aged whole grain flour from wheat with novel alleles in Lpx-D1 significantly reduces the concentration of the major bitter compound found in whole grain products.

The above examples are provided to illustrate the invention but not limit its scope. Other variants of the invention will be readily apparent to one of ordinary skill in the art and are encompassed by the appended claims and all their equivalents. The examples above used TILLING technology to create and identify mutations in one or more Lpx genes of wheat but one of ordinary skill in the art would understand that other methods such as targeted mutagenesis (also known as site-directed mutagenesis, site-specific mutagenesis, oligonucleotide-directed mutagenesis or genome editing) could be used to create the useful mutations disclosed herein in one or more Lpx1 loci of wheat (see for example Zhang et al., PNAS 107(26):12028-12033, 2010; Saika et al., Plant Physiology 156:1269-1277, 2011). All publications, patents, and patent applications cited herein are hereby incorporated by reference.

| | | |
|---|---|---|
| | Informational Sequence Listing | |
| SEQ ID NO | Name | Sequence Length |
| 1 | Lpx-D1 Genomic Sequence | 3863 bp |
| 2 | Lpx-D1 Coding Sequence | 2586 bp |
| 3 | Lpx-D1 Protein Sequence | 862 amino acids |
| 4 | Lpx-B1.2 Genomic Sequence | 4263 bp |
| 5 | Lpx-B1.2 Coding Sequence | 2586 bp |
| 6 | Lpx-B1.2 Protein Sequence | 862 amino acids |
| SEQ ID NO: 1 | Lpx-D1 genomic nucleic acid sequence | ATGATACTGGGCGGGCTCATCGACAGCCTGACCGGCGCG<br>AACAAGAACGCACGTCTCAAGGGCACGGCGGTGCTGATG<br>AGGAAGAACGTGCTGGACCTCACCGACTTCGGCGCCACC<br>ATCATGGACGGCATCGGCGACTTCCTCGGCAAGGGCGTC<br>ACCTGCCAGCTTATCAGCTCCACCCTCATCGACCACGGTA<br>AGCAGTGCACCCTTCTCCTCTTCCTCCTCCTCTCCTCT<br>CCTTACTAGATATGTCTTTTAATTTGTGTTGTCGGCCATGG<br>ATGCATGGATGTATCTCGATCGGCTAAAGATAGAGATAG<br>CCTCGGTCGGTCGGTCGTCTTTAGCTGAGCATGGGCATGC<br>CATGGAAAGAAGAGACAATAGTAGCATGGTGCGTGCACC<br>AGAGCTTGCAGAGCATCGGATGCTCGAGACAAAGCAATA<br>GAACAAGCAAGCACACGTCAAAAGTAACTATCACAACCT<br>AAACTAAAGCTTTGAACTCGACTCCCAACAATCAATCAG<br>GTTGACACGTACTAGTAAACTAAAGCACATGTGAGAACG<br>AACGAACTGCGTGCGTGCGTGCAGACAACGGCGGGCGCG<br>GGAAGGTGGGCGCGGAGGCGGAGCTGGAGCAGTGGGTG<br>ACGAGCCTGCCGTCGCTGACGACGGGGGAGTCCAAGTTC<br>GGCCTCACCTTCGACTGGGAGGTGGAGAAGCTGGGGGTG<br>CCCGGCGCCATCGTCGTCAACAACTACCACAGCTCCGAGT<br>TCCTGCTCAAGACGGTCACCCTCCACGACGTCCCCGGCCG<br>CGGCAACCTCTCCTTCGTCGCCAACTCCTGGATCTACCCC<br>GCCGCCACCTACACCTACAGCCGCGTCTTCTTCGCCAACG<br>ATGTGAGTTGTGAGCCTCCCTTGTTTCCTCTCCTTTCCTTT<br>CCATTTCACTGCCTTCGTCATTCATGGTCATTAAGTCTTCT<br>TTGAGATAAGATAAGATTAGTAGGTGCAGAATTTATTCCG<br>TGTTGGTAGAGAAAAAGGATATGGCTAGGTGCAGCAGAA<br>GATTGAATGAAACCGGCACCGTGGCACCGTGGTAGGTGA<br>AGAAAACTGTTGCCCTTGCCTGACCAAGTGTGCGACCTGC<br>TGCTGCCGGGTTATTTCTTTGAGATAAGACACGTACGTGG<br>GCTCACATGAACGCAAGCATGGCTCCACCACCATGGGAC<br>GACCTCGGTCGCTACATGGCCGCCTCAGAACTTTTAAAAG<br>ATGTTGCATGATACGGTAGTAGCACTCAATCCGGTTTACT<br>TTGCCGAAACGGTGACATAAAACACATGAAAGAAAAAGC<br>GATTATACTGCTCTAGTTGGCAAAGCAAAATCATCTAATT<br>CACGTACTTCTTTTGTCATGAGCAAGCCATCGATCGGCTT<br>CCGGCCTGCAGGTTCAGTGCTCGTCTAAAATGACAAATTT<br>TCTTGCCATGTTACGCGCGTACAGACGTACCTGCCGAGCC<br>AGATGCCGGCGGCGCTGAAGCCGTACCGCGACGACGAGC<br>TCCGGAACCTGCGGGGCGACGATCGGCAGGGGCCCTACC<br>AGGAGCACGACCGCGTCTACCGCTACGACGTCTACAACG<br>ACCTCGGCGAGGGCCGCCCGGTCCTCGGCGGCAGCGCCG<br>AGCACCCTTACCCGCGGCGCGGCCGCACGGGCCGCAAGC<br>CCAACGCCAGCGACCCGAGCCTGGAGAGCCGGCTGTCGC<br>TGCTGGAGCAGATCTACGTGCCGCGGGACGAGAAGTTCG<br>GCCACCTCAAGACGTCCGACTTCCTGGGCTACTCCATCAA<br>GGCCATCACGCAGGGCATCCTGCCGGCGGTGCGCACCTA<br>CGTCGACACCACCCCCGGCGAGTTCGACTCCTTCCAGGAC<br>ATCATGAACCTCTACGAGGGCGGCATCAAGCTGCCCATG<br>GTGCCCGCCCTCGAGGAGCTGCGCAAGCAGTTCCCGCTCC<br>AGCTCATCAAGGACCTGCTCCCCGTGGGCGGCGACTCGCT<br>GCTGAAGCTCCCTGTGCCACATATCATCCAGGCGGACCA<br>GCAGGCGTGGAGGACCGACGAGGAGTTCGCGCGCGAGGT<br>GCTCGCCGGCGTCAACCCGGTCATGATCACGCGTCTCACG<br>GTCAGTCAACGGTTACTATGTGTAGAATATGTATGTTGTC<br>CATGGTGAGAGCACGCAAATCTTACTTGGTGTTGGGTCGG<br>CATGCATGCAGGAGTTCCCGCCAAAAAGTAGTCTTGACC<br>CTAGCAAGTTTGGTGACCACACCAGCACCATCACGGCGG<br>CACACATCCAGAAGAACCTCGAGGGCCTCACCGTGCAGC<br>AGGTAATAATATACACGATCGAGTTGGCCAACCCATCGC<br>GATCAACTGTGATTTGGTGGGAGCAGGTCTAAGTAATTTT<br>GGCTTGTTGCATGCAGGCGCTGGAAAGTAACAGGCTCTA<br>CATACTTGATCACCACGACCGGTTCATGCCGTTCCTGATC<br>GAAGTCAACAACCTGCCCGGCAACTTCATCTACGCCACC<br>AGGACCCTCTTCTTCCTGCGCGGCGACGGCAGGCTCACGC<br>CGCTCGCCATCGAGCTGAGCGAGCCCGTCATCCTGGGCG |

| Informational Sequence Listing | | |
|---|---|---|
| SEQ ID NO | Name | Sequence Length |
| | | GCCTCACCACCGCCAAGAGCAAGGTGTACACGCCGGTGC
CGAGCGGCAGCGTCGAAGGCTGGGTGTGGGAGTTCGCCA
AGGCCTACGTCGCCGTCAACGACTCCGGCTGGCACCAGC
TCGTCAGCCACTGGCTACGTGCACTACGGATTAACCAAAC
AATGCGACACACCCCTCAAAAAAGAAAAGAAAAACAA
TGGCGACACTGACTCGGTGTGATTCAGTCAGTCGATGCAC
AACTGACCTATGATTGAAACGTGTAGGCTGAACACCCAC
GCGGTGATGGAGCCGTTTGTGATCTCGACGAACCGGCAC
CTCAGCGTGACGCACCCGGTGCACAAGCTGCTGAGCCCG
CACTACCGCGACACCATGACCATCAACGCGCTGGCGCGG
CAGACGCTCATCAACGCCGGCGGCATCTTCGAGATGACG
GTGTTCCCGGGCAAGTTTGCGCTGGGGATGTCGTCGGTGG
TGTACAAGGACTGGAAGTTCACCGAGCAGGGCCTGCCCG
ACGATCTCATCAAGAGGGGCATGGCGGTGGAGGACCTAT
CGAGCCCTTACAAGGTGCGGCTTCTGGTGTCGGACTACCC
GTACGCGGCGGACGGGCTGGCGATCTGGCACGCCATCGA
GCAGTACGTGGGCGAGTACCTGGCCATCTACTACCCGGA
CGACGGCGTGCTGCGGGGCGACACGGAGCTGCAGGCGTG
GTGGAAGGAGGCGCGCGAGGTCGGGCACGGCGACCTCAA
GGACGCGCCGTGGTGGCCGAGGATGCAGGGCGTGGGGGA
GCTGGCCAAGGCGTGCACCACCATCATCTGGATCGGGTC
GGCGCTGCACGCGGCGGTCAACTTCGGGCAGTACCCGTA
CGCGGGGTTCCTCCCGAACCGGCCGACGGTGAGCCGGCG
CCGCATGCCGGAGCCCGGGACGGACGCGTACGCGGAGCT
GGAGCGCGACCCGGAGCGGGCCTTCATCCACACCATCAC
CAGCCAGATCCAGACCATCATCGGCATCTCGCTGTTGGAG
GTGCTGTCCAAACACTCCTCTGACGAGCTCTACCTGGGGC
AGCGCGACACGCCGGAGTGGACCTCGGACCCCAAGGCCC
TGGAGGTGTTCAAGCGGTTCAGCGAGCGGCTGGTGGAGA
TCGAGAGCAAGGTGGTGGGCATGAACCACGACCCGCAGC
TGTTGAACCGCAACGGCCCGGCCAAGCTCCCCTACATGCT
GCTCTACCCCAACACCTCCGACCACAAGGGCGCGCCGC
CGGCCTCACCGCCAAGGGCATCCCCAACAGCATCTCCATC
TGA |
| SEQ ID NO: 2 | Lpx-D1 Coding sequence | ATGATACTGGGCGGGCTCATCGACAGCCTGACCGGCGCG
AACAAGAACGCACGTCTCAAGGGCACGGCGGTGCTGATG
AGGAAGAACGTGCTGGACCTCACCGACTTCGGCGCCACC
ATCATGGACGGCATCGGCGACTTCCTCGGCAAGGGCGTC
ACCTGCCAGCTTATCAGCTCCACCCTCATCGACCACGACA
ACGGCGGGCGCGGGAAGGTGGGCGCGGAGGCGGAGCTG
GAGCAGTGGGTGACGAGCCTGCCGTCGCTGACGACGGGG
GAGTCCAAGTTCGGCCTCACCTTCGACTGGGAGGTGGAG
AAGCTGGGGGTGCCCGGCGCCATCGTCGTCAACAACTAC
CACAGCTCCGAGTTCCTGCTCAAGACGGTCACCCTCCACG
ACGTCCCCGGCCGCGGCAACCTCTCCTTCGTCGCCAACTC
CTGGATCTACCCCGCCGCCACCTACACCTACAGCCGCGTC
TTCTTCGCCAACGATACGTACCTGCCGAGCCAGATGCCGG
CGGCGCTGAAGCCGTACCGCGACGACGAGCTCCGGAACC
TGCGGGCGACGATCGGCAGGGGCCCTACCAGGAGCACG
ACCGCGTCTACCGCTACGACGTCTACAACGACCTCGGCG
AGGGCCGCCCGGTCCTCGGCGGCAGCGCCGAGCACCCTT
ACCCGCGGCGCGGCCGCACGGGCCGCAAGCCCAACGCCA
GCGACCCGAGCCTGGAGAGCCGGCTGTCGCTGCTGGAGC
AGATCTACGTGCCGCGGGACGAGAAGTTCGGCCACCTCA
AGACGTCCGACTTCCTGGGCTACTCCATCAAGGCCATCAC
GCAGGGCATCCTGCCGGCGGTGCGCACCTACGTCGACAC
CACCCCCGGCGAGTTCGACTCCTTCCAGGACATCATGAAC
CTCTACGAGGGCGGCATCAAGCTGCCCATGGTGCCCGCC
CTCGAGGAGCTGCGCAAGCAGTTCCCGCTCCAGCTCATCA
AGGACCTGCTCCCCGTGGGCGGCGACTCGCTGCTGAAGC
TCCCTGTGCCACATATCATCCAGGCGGACCAGCAGGCGT
GGAGGACCGACGAGGAGTTCGCGCGCGAGGTGCTCGCCG
GCGTCAACCCGGTCATGATCACGCGTCTCACGGAGTTCCC
GCCAAAAAGTAGTCTTGACCCTAGCAAGTTTGGTGACCA
CACCAGCACCATCACGGCGGCACACATCCAGAAGAACCT
CGAGGGCCTCACCGTGCAGCAGGCGCTGGAAAGTAACAG
GCTCTACATACTTGATCACCACGACCGGTTCATGCCGTTC
CTGATCGAAGTCAACAACCTGCCCGGCAACTTCATCTACG
CCACCAGGACCCTCTTCTTCCTGCGCGGCGACGGCAGGCT
CACGCCGCTCGCCATCGAGCTGAGCGAGCCCGTCATCCTG
GGCGGCCTCACCACCGCCAAGAGCAAGGTGTACACGCCG
GTGCCGAGCGGCAGCGTCGAAGGCTGGGTGTGGGAGTTC
GCCAAGGCCTACGTCGCCGTCAACGACTCCGGCTGGCAC
CAGCTCGTCAGCCACTGGCTGAACACCCACGCGGTGATG |

| Informational Sequence Listing | | |
|---|---|---|
| SEQ ID NO | Name | Sequence Length |
| | | GAGCCGTTTGTGATCTCGACGAACCGGCACCTCAGCGTG<br>ACGCACCCGGTGCACAAGCTGCTGAGCCCGCACTACCGC<br>GACACCATGACCATCAACGCGCTGGCGCGGCAGACGCTC<br>ATCAACGCCGGCGGCATCTTCGAGATGACGGTGTTCCCG<br>GGCAAGTTTGCGCTGGGGATGTCGTCGGTGGTGTACAAG<br>GACTGGAAGTTCACCGAGCAGGGCCTGCCCGACGATCTC<br>ATCAAGAGGGGCATGGCGGTGGAGGACCTATCGAGCCCT<br>TACAAGGTGCGGCTTCTGGTGTCGGACTACCGTACGCGG<br>CGGACGGGCTGGCGATCTGGCACGCCATCGAGCAGTACG<br>TGGGCGAGTACCTGGCCATCTACTACCCGGACGACGGCG<br>TGCTGCGGGGCGACACGGAGCTGCAGGCGTGGTGGAAGG<br>AGGCGCGCGAGGTCGGGCACGGCGACCTCAAGGACGCGC<br>CGTGGTGGCCGAGGATGCAGGGCGTGGGGGAGCTGGCCA<br>AGGCGTGCACCACCATCATCTGGATCGGGTCGGCGCTGC<br>ACGCGGCGGTCAACTTCGGGCAGTACCCGTACGCGGGGT<br>TCCTCCCGAACCGGCCGACGGTGAGCCGGCGCCGCATGC<br>CGGAGCCCGGGACGGACGCGTACGCGGAGCTGGAGCGCG<br>ACCCGGAGCGGGCCTTCATCCACACCATCACCAGCCAGA<br>TCCAGACCATCATCGGCATCTCGCTGTTGGAGGTGCTGTC<br>CAAACACTCCTCTGACGAGCTCTACCTGGGGCAGCGCGA<br>CACGCCGGAGTGGACCTCGGACCCCAAGGCCCTGGAGGT<br>GTTCAAGCGGTTCAGCGAGCGGCTGGTGGAGATCGAGAG<br>CAAGGTGGTGGGCATGAACCACGACCCGCAGCTGTTGAA<br>CCGCAACGGCCCGGCCAAGCTCCCCTACATGCTGCTCTAC<br>CCCAACACCTCCGACCACAAGGGCGCCGCCGCCGGCCTC<br>ACCGCCAAGGGCATCCCCAACAGCATCTCCATCTGA |
| SEQ ID NO:3 | Lpx-D1 Amino acid sequence | MILGGLIDSLTGANKNARLKGTAVLMRKNVLDLTDFGATIM<br>DGIGDFLGKGVTCQLISSTLIDHDNGGRGKVGAEAELEQWV<br>TSLPSLTTGESKFGLTFDWEVEKLGVPGAIVVNNYHSSEFLL<br>KTVTLHDVPGRGNLSFVANSWIYPAATYTYSRVFFANDTYL<br>PSQMPAALKPYRDDELRNLRGDDRQGPYQEHDRVYRYDV<br>YNDLGEGRPVLGGSAEHPYPRRGRTGRKPNASDPSLESRLS<br>LLEQIYVPRDEKFGHLKTSDFLGYSIKAITQGILPAVRTYVDT<br>TPGEFDSFQDIMNLYEGGEKLPMVPALEELRKQFPLQLIKDL<br>LPVGGDSLLKLPVPHIIQADQQAWRTDEEFAREVLAGVNPV<br>MITRLTEFPPKSSLDPSKFGDHTSTITAAHIQKNLEGLTVQQA<br>LESNRLYILDHHDRFMPFLIEVNNLPGNFIYATRTLFFLRGDG<br>RLTPLAIELSEPVILGGLTTAKSKVYTPVPSGSVEGWVWEFA<br>KAYVAVNDSGWHQLVSHWLNTHAVMEPFVISTNRHLSVTH<br>PVHKLLSPHYRDTMTINALARQTLINAGGEFEMTVFPGKFAL<br>GMSSVVYKDWKFTEQGLPDDLIKRGMAVEDLSSPYKVRLL<br>VSDYPYAADGLAIWHAIEQYVGEYLAIYYPDDGVLRGDTEL<br>QAWWKEAREVGHGDLKDAPWWPRMQGVGELAKACTTII<br>WIGSALHAAVNFGQYPYAGFLPNRPTVSRRRMPEPGTDAY<br>AELERDPERAFIHTITSQIQTIIGISLLEVLSKHSSDELYLGQRD<br>TPEWTSDPKALEVFKRFSERLVEIESKVVGMNHDPQLLNRN<br>GPAKLPYMLLYPNTSDHKGAAAGLTAKGIPNSISI |
| SEQ ID NO: 4 | Lpx-B1.2 genomic nucleic acid sequence | ATGATACTGGGCGGGCTCGTCGACAGCCTGACCGGCGCG<br>AACAAGAGCGCACGGCTCCAGGGCACGGTGGTGCTCATG<br>AGGAAGAACGTGCTGGACCTCAACGACTTCGGCGCCACC<br>ATCATGGACGGCATCGGCGAGTTCATCGGCAAGGGCGTC<br>ACCTGCCAGCTTATCAGCTCCACCCTCGTCGACCACGGTA<br>AGCAGTGCACCATTCTCCTCTTCCTCCTCCTCCTCTCCTTG<br>GTAGATATTTCTTTTGTGTTGTCGGCCATGGATGCATGGA<br>TGTATCTCGATCGGCTAAAGAATGATAGATAGATAGCCA<br>TGGTCGGTCGTCTTTAGCTGAGCATGGGCATGGAAAGAA<br>GAGACGAGAGCATGGTGCGTGCACCAGAGCTTACAGAGC<br>ACCAGATGCTCCAGACAAAGCAATAGAACAAGCAAGGAC<br>ACGTCGCCAAAAGCAACAAACACAACCTAAACTAAAGCA<br>CAAAGACGTAGCGATGAAAAAAGCATCGTGGGCAGATGC<br>TCTAACCATGCGAGACCGTGCTCCGTGCAGACAACGGCG<br>GGCGTGGGAAGGTGGGCGCGGAGGCGGAGCTGGAGCAG<br>TGGGTGACGAGCCTGCCGTCGCTGACGACGGGGAGTCC<br>AAGTTCGGCCTCACCTTCGACTGGGAGGTGGAGAAGCTG<br>GGCGTGCCGGGCGCCATCATCGTCAACAACCACCACAGC<br>TCCGAGTTCCTGCTCAAGACCGTCACCCTCCACGACGTCC<br>CCGGCCGCGGCAACCTCTCCTTCGTCGCCAACTCCTGGAT<br>CTACCCCGTTGGCAGCTACACCTACAGCCGCGTCTTCTTC<br>GCCAACGATGTGAGTTGTGACTTGTGAGCCTTGCCTTTCC<br>TCTCCTTTCCTTTTCACTGGCTTCCTCATTCATGGTCATTT<br>AAGTCTTCTCTGAGATAAGATAAGATTAGTAGGTGCAGA<br>ATTTATTCCATGTTGGTAGAAAAAAGATATGGCTAGGTGC<br>AGCAGAAGATTGAATGAATGTGGCACCGTGGTTGGTGAA |

| Informational Sequence Listing | | |
|---|---|---|
| SEQ ID NO | Name | Sequence Length |
| | | GACAACTGCTGCCCTTGACTGACCTGCTGCTGGGTTCTTC |
| | | CTTTGGGATAAGAACACCGAGCGAGACACGTACGTACGT |
| | | GAGCTCAAACGAACCCATGGCTCCACCTCCATGACCTGAT |
| | | CCTTCCCTTGAAACGACCTAAGATAGTTACATGGCCGAGC |
| | | CCAGAACAAACTTTTAAAAAGAGATGCTGCATAGTCATG |
| | | ATACAGTGACATAATAAAACACATGAAAGAAGAGGCGAT |
| | | TATTGCTCTAGTTGGCAAAGCAAAATAATCTACTAACTCT |
| | | TGTGTAGTACTACTAGCTAGCAACATACGTACGGGAGTTC |
| | | TTTTGTCATAAACAAGCGATCGATCGGCTTCCTGCAGGTT |
| | | CAGTGCTCATCTAAAATGACAAATTTTTTGGTATGTGTAC |
| | | CTACGCGCAGACGTACCTGCCGAGCCAGATGCCAGCGGC |
| | | GCTGAAGCCGTACCGCGACGACGAGCTCCGGAACCTGCG |
| | | GGGCGACGACCGGCAGGGCCCCTACCAGGAGCACGACCG |
| | | CGTCTACCGCTACGACGTCTACAACGACCTCGGCGAGGG |
| | | CCGCCCCGTCCTCGGCGGCAGCGCCGAGCACCCCTATCCG |
| | | CGCCGCGGCCGCACCGGGCGCAAGCCCAACGCCAACGAC |
| | | CCGAGCTTGGAGAGCCGGCTGTCGCTGCTGGAGCAGATC |
| | | TACGTGCCGCGGGACGAGAAGTTCGGCCACCTCAAGACG |
| | | TCCGACTTCCTGGGCTACTCCATCAAGGCCATCACGCAGG |
| | | GCATCCTGCCGGCGGTGCGCACCTACGTCGACACCACCCC |
| | | CGGCGAGTTCGACTCCTTCCAGGACATCATCAACCTCTAC |
| | | GAGGGCGGCATCAAGCTGCCCAACGTCCCCGCCCTCGAG |
| | | GAGCTGCGCAAGCAGTTCCCGCTCCAGCTCATCAAGGAC |
| | | CTCCTCCCCGTGGGTGGCGACTCGCTGCTCAAGCTCCCCG |
| | | TCCCCCACATCATCCAGGCGGACCAGCAGGCGTGGCGGA |
| | | CCGACGAGGAGTTCTCCCGGGAGGTCCTTGCCGGCGTCA |
| | | ACCCGGTCATGATCACGCGTCTCACGGTGAGTCAACAAT |
| | | AATTGAACAGTCTTACTAAAGGCCCGTTCGGAGGCTCTCC |
| | | ACTCCTCAACTCTCTCCCGGAGCGGCCGGAGCTTCAGTTT |
| | | AAAATTATGGAGTGGCCGAAGAGGTACTCCGCAGATCCT |
| | | TGTATTCTGCGGAGCTGGGCCAGTGCCGAACAGGGCCTA |
| | | AGTCTCAGTCGATCTATATCCGACAGATCTTACATTAAGA |
| | | TTCTTTTCAGTTTTTCTTTTTCTTTTTTTGCATGTTATATCA |
| | | AATTTGACTAAGACTTCATTAAATCTCGGTCGACAGAAAC |
| | | TTAGCCACACACCATAATTGAACGATGAATGAGTATGCT |
| | | ATCCATGGATCGAGAACCGAGAGGTGAGAGCGTGCCTGA |
| | | TCTTAATTTGTGTTGGGTGGCATGCATACAGGAGTTCCCG |
| | | CCAAAAAGTAGTCTGGACCCTAGCAAGTTTGGTGACCAC |
| | | ACCAGCACCGTCACGGCGGCGCACATCGAGAAAAACCTC |
| | | GAAGGCCTCACCGTGCAGCAGGTAATAATACTACAATAC |
| | | ACGAGTCGGCCAACCCATCGCGATCAACTGTGATTTGATG |
| | | GAAGCAGGTGTAACTAATTTTGGCATGTTGCAACTTGTTG |
| | | CATGCAGGCCCTTGAAAGCAACCGGTTGTACATCCTTGAT |
| | | CACCACGACCGGTTCATGCCGTTCCTCATCGACGTCAACA |
| | | ACCTGCCCGGCAACTTCATCTACGCCACGAGGACCCTCTT |
| | | CTTCCTGCGCGGCGACGGCAGGCTCACGCCGCTCGCCATC |
| | | GAGCTCAGCGAGCCTGTCATACAGGGCGGCCTCACCACC |
| | | GCCAAGAGCAAGGTGTACACGCCGGTGCCGAGCGGCAGC |
| | | GTCGAAGGATGGGTGTGGGAGTTCGCCAAGGCCTACGTC |
| | | GCCGTCAACGACTCTGGGTGGCACCAGCTCGTCAGCCACT |
| | | GGTACGTGCACTACGGACTAACCAAACAACTGAGAACAG |
| | | TCTTACTAAGTCTCAGTCGATCTATATCCGACACTGACTC |
| | | GGTGTGATTCAGTCAGTCGATGCACAACTGACCTATGATT |
| | | GAAACGTGCAGGCTGAACACTCATGCGGTGATGGAGCCG |
| | | TTTGTGATCTCGACGAACCGGCAGCTCAGCGTGACGCACC |
| | | CGGTGCACAAGCTGCTGAGCCCGCACTACCGCGACACGA |
| | | TGACCATCAACGCGCTAGCGCGGCAGACGCTCATCAACG |
| | | CCGGCGGCATCTTCGAGATGACGGTGTTCCCGGGCAAGTT |
| | | CGCGTTGGGGATGTCGTCAGTGGTGTACAAGGACTGGAA |
| | | GTTCACGGAGCAGGGCCTGCCCGACGATCTCATCAAGAG |
| | | GTACGTACCAAGTATAATGTACTAATGAAACTGTGTTACA |
| | | AATCATGCTTTTAGATGACTGACGACACATACGTGGTGCA |
| | | TAACAAAAAAATGCAGGGGCATGGCGGTGGAGGACCCGT |
| | | CGAGCCCGTACAAGGTGAGGCTGCTGGTGTCTGACTACC |
| | | CGTACGCGGCGGACGGGCTGGCGATCTGGCACGCCATCG |
| | | AGCAGTACGTGAGCGAGTACCTGGCCATTTACTACCCGA |
| | | ACGATGGCGTGGTGCAGGGCGACGTGGAGCTGCAGGCGT |
| | | GGTGGAAGGAGGTGCGCGAGGTGGGGCACGGCGACCTCA |
| | | AGGTCGCGCCATGGTGGCCGAGGATGCAAGCCGTGGGCG |
| | | AGCTGGCCAAGGCGTGCACCACCATCATCTGGATCGGGT |
| | | CGGCGCTGCATGCGGCGGTCAACTTCGGGCAGTACCCAT |
| | | ACGCGGGGTTCCTCCCGAACCGGCCGACGGTGAGCCGGC |
| | | GCCGCATGCCGGAGCCGGGGACCGAGCAGTACGCGGAGC |
| | | TGGAGCGCGACCCGGAGCGGGCCTTCATCCACACCATCA |
| | | CTAGCCAGATCCAGACCATCATCGGCATCTCGCTGCTGGA |

| SEQ ID NO | Name | Sequence Length |
|---|---|---|
| | | GGTGCTGTCGAAGCACTCCTCCGACGAGCTCTACCTCGGG
CAGCGTGACACGCCGGAGTGGACCTCGGACCCCAAGGCC
CTGGAGGTGTTCAAGCGGTTCAGCGAGCGGCTAGCGGAG
ATCGAGAGCAAGGTGGTGGGCATGAACCACGACCCGCAG
CTGTTGAACCGCAACGGTCCGGCCAAGTTCCCCTACATGT
TGCTCTACCCCAACACCTCCGATCACAAGGGCGCCGCCGC
CGGGGCTCACCGCTAAGGGCATCCCCAACAGCATCTCCATC
TGA |
| SEQ ID NO: 5 | Lpx-B1.2 Coding sequence | ATGATACTGGGCGGGCTCGTCGACGCCTGACCGGCGCG
AACAAGAGCGCACGGCTCCAGGGCACGGTGGTGCTCATG
AGGAAGAACGTGCTGGACCTCAACGACTTCGGCGCCACC
ATCATGGACGGCATCGGCGAGTTCATCGGCAAGGGCGTC
ACCTGCCAGCTTATCAGCTCCACCCTCGTCGACCACGACA
ACGGCGGGCGTGGGAAGGTGGGCGCGGAGGCGGAGCTG
GAGCAGTGGGTGACGAGCCTGCCGTCGCTGACGACGGGG
GAGTCCAAGTTCGGCCTCACCTTCGACTGGGAGGTGGAG
AAGCTGGGCGTGCCGGGCGCCATCATCGTCAACAACCAC
CACAGCTCCGAGTTCCTGCTCAAGACCGTCACCCTCCACG
ACGTCCCCGGCCGCGGCAACCTCTCCTTCGTCGCCAACTC
CTGGATCTACCCCGTTGGCAGCTACACCTACAGCCGCGTC
TTCTTCGCCAACGATACGTACCTGCCGAGCCAGATGCCAG
CGGCGCTGAAGCCGTACCGCGACGACGAGCTCCGGAACC
TGCGGGGCGACGACCGGCAGGGCCCCTACCAGGAGCACG
ACCGCGTCTACCGCTACGACGTCTACAACGACCTCGGCG
AGGGCCGCCCCGTCCTCGGCGGCAGCGCCGAGCACCCCT
ATCCGCGCCGCGGCCGCACCGGGCGCAAGCCCAACGCCA
ACGACCCGAGCTTGGAGAGCCGGCTGTCGCTGCTGGAGC
AGATCTACGTGCCGCGGGACGAGAAGTTCGGCCACCTCA
AGACGTCCGACTTCCTGGGCTACTCCATCAAGGCCATCAC
GCAGGGCATCCTGCCGGCGGTGCGCACCTACGTCGACAC
CACCCCCGGCGAGTTCGACTCCTTCCAGGACATCATCAAC
CTCTACGAGGGCGGCATCAAGCTGCCCAACGTCCCCGCC
CTCGAGGAGCTGCGCAAGCAGTTCCCGCTCCAGCTCATCA
AGGACCTCCTCCCCGTGGGTGGCGACTCGCTGCTCAAGCT
CCCCGTCCCCCACATCATCCAGGCGGACCAGCAGGCGTG
GCGGACCGACGAGGAGTTCTCCCGGGAGGTCCTTGCCGG
CGTCAACCCGGTCATGATCACGCGTCTCACGGAGTTCCCG
CCAAAAAGTAGTCTGGACCCTAGCAAGTTTGGTGACCAC
ACCAGCACCGTCACGGCGGCGCACATCGAGAAAAACCTC
GAAGGCCTCACCGTGCAGCAGGCCCTTGAAAGCAACCGG
TTGTACATCCTTGATCACCACGACCGGTTCATGCCGTTCC
TCATCGACGTCAACAACCTGCCCGGCAACTTCATCTACGC
CACGAGGACCCTCTTCTTCCTGCGCGGCGACGGCAGGCTC
ACGCCGCTCGCCATCGAGCTCAGCGAGCCTGTCATACAG
GGCGGCCTCACCACCGCCAAGAGCAAGGTGTACACGCCG
GTGCCGAGCGGCAGCGTCGAAGGATGGGTGTGGGAGTTC
GCCAAGGCCTACGTCGCCGTCAACGACTCTGGGTGGCAC
CAGCTCGTCAGCCACTGGCTGAACACTCATGCGGTGATG
GAGCCGTTTGTGATCTCGACGAACCGGCAGCTCAGCGTG
ACGCACCCGGTGCACAAGCTGCTGAGCCCGCACTACCGC
GACACGATGACCATCAACGCGCTAGCGCGGCAGACGCTC
ATCAACGCCGGCGGCATCTTCGAGATGACGGTGTTCCCG
GGCAAGTTCGCGTTGGGGATGTCGTCAGTGGTGTACAAG
GACTGGAAGTTCACGGAGCAGGGCCTGCCCGACGATCTC
ATCAAGAGGGGCATGGCGGTGGAGGACCCGTCGAGCCCG
TACAAGGTGAGGCTGCTGGTGTCTGACTACCCGTACGCG
GCGGACGGGCTGGCGATCTGGCACGCCATCGAGCAGTAC
GTGAGCGAGTACCTGGCCATTTACTACCCGAACGATGGC
GTGGTGCAGGGCGACGTGGAGCTGCAGGCGTGGTGGAAG
GAGGTGCGCGAGGTGGGGCACGGCGACCTCAAGGTCGCG
CCATGGTGGCCGAGGATGCAAGCCGTGGGCGAGCTGGCC
AAGGCGTGCACCACCATCATCTGGATCGGGTCGGCGCTG
CATGCGGCGGTCAACTTCGGGCAGTACCCATACGCGGGG
TTCCTCCCGAACCGGCCGACGGTGAGCCGGCGCCGCATG
CCGGAGCCGGGGACCGAGCAGTACGCGGAGCTGGAGCGC
GACCCGGAGCGGGCCTTCATCCACACCATCACTAGCCAG
ATCCAGACCATCATCGGCATCTCGCTGCTGGAGGTGCTGT
CGAAGCACTCCTCCGACGAGCTCTACCTCGGGCAGCGTG
ACACGCCGGAGTGGACCTCGGACCCCAAGGCCCTGGAGG
TGTTCAAGCGGTTCAGCGAGCGGCTAGCGGAGATCGAGA
GCAAGGTGGTGGGCATGAACCACGACCCGCAGCTGTTGA
ACCGCAACGGTCCGGCCAAGTTCCCCTACATGTTGCTCTA
CCCCAACACCTCCGATCACAAGGGCGCCGCCGCCGGGCT
CACCGCTAAGGGCATCCCCAACAGCATCTCCATCTGA |

-continued

| SEQ ID NO | Name | Sequence Length |
|---|---|---|
| SEQ ID NO:6 | Lpx-B1.2 Amino acids sequence | MILGGLVDSLTGANKSARLQGTVVLMRKNVLDLNDFGATI<br>MDGIGEFIGKGVTCQLISSTLVDHDNGGRGKVGAEAELEQW<br>VTSLPSLTTGESKFGLTFDWEVEKLGVPGAIIVNNHHSSEFLL<br>KTVTLHDVPGRGNLSFVANSWIYPVGSYTYSRVFFANDTYL<br>PSQMPAALKPYRDDELRNLRGDDRQGPYQEHDRVYRYDV<br>YNDLGEGRPVLGGSAEHPYPRRGRTGRKPNANDPSLESRLS<br>LLEQIYVPRDEKFGHLKTSDFLGYSIKAITQGILPAVRTYVDT<br>TPGEFDSFQDIINLYEGGIKLPNVPALEELRKQFPLQUKDLLP<br>VGGDSLLKLPVPHIIQADQQAWRTDEEFSREVLAGVNPVMI<br>TRLTEFPPKSSLDPSKFGDHTSTVTAAHIEKNLEGLTVQQAL<br>ESNRLYILDHHDRFMPFLIDVNNLPGNFIYATRTLFFLRGDG<br>RLTPLAIELSEPVIQGGLTTAKSKVYTPVPSGSVEGWVWEFA<br>KAYVAVNDSGWHQLVSHWLNTHAVMEPFVISTNRQLSVTH<br>PVHKLLSPHYRDTMTINALARQTLINAGGEFEMTVFPGKFAL<br>GMSSVVYKDWKFTEQGLPDDLIKRGMAVEDPSSPYKVRLL<br>VSDYPYAADGLAIWHAIEQYVSEYLAIYYPNDGVVQGDVE<br>LQAWWKEVREVGHGDLKVAPWWPRMQAVGELAKACTTII<br>WIGSALHAAVNFGQYPYAGFLPNRPTVSRRRMPEPGTEQYA<br>ELERDPERAFIHTITSQIQTIIGISLLEVLSKHSSDELYLGQRDT<br>PEWTSDPKALEVFKRFSERLAEIESKVVGMNHDPQLLNRNG<br>PAKFPYMLLYPNTSDHKGAAAGLTAKGEPNSISI |
| SEQ ID NO: 7 | TaLpx1D_4_L-1 | TGGTGAGAGCACGCAAATCTTACTTGG |
| SEQ ID NO: 8 | TaLpxB1.2-D1-5R1 | CGTTTCAATCATAGGTCAGTTGTGCATCGA |
| SEQ ID NO: 9 | TaLpx1D_67 R 3 | CGCGTACGGGTAGTCCGACACCAGAAG |
| SEQ ID NO: 10 | TaLpx1D_In1_L4 | GCATGCCATGGAAAGAAGAGACAATAGTAGC |
| SEQ ID NO: 11 | TaLpx1D_3_R-1 | TGCGTGCTCTCACCATGGACAACATACATA |
| SEQ ID NO: 12 | TaLpx1D_Ex5_L6 | GCAGGCGCTGGAAAGTAACAGGCTCT |
| SEQ ID NO: 13 | TaLpx1D_Ex7_R3 | TGGACGAGACGAAGCTCCGATGTACCA |
| SEQ ID NO: 14 | TaLpx1.2B_4_L-1 | GAGGTGAGAGCGTGCCTGATCTTAATTTG |
| SEQ ID NO: 16 | LpxD1proL | TCATGCCGCTGATCGTCGC |
| SEQ ID NO: 17 | LpxD1proR | CTTGCTGCTATTTCAGTACCG |
| SEQ ID NO: 15 | Lpx-D1 Promoter and Exon1 | CACCGCTGTAACAGCCCCATTGTCTAGCTCAAAGAACTCT<br>CTCATGGCCACAATTACATCAGGAGGAAGCTGCTCTTTGA<br>ACTTTACAGCGAAGGCATCCAGGGTGGCAGTGGTGACGT<br>CCTGCCCGTTCTTGATGATGCCCAGGCTGCGGCCAATAAA<br>CTGCTCAGCCGCCTGTGCCGCCGGCGTCGTTGCTGCGAGG<br>ACAGCAGGGCGCCTGATCCTCTGCAGGGAGAGGCCACCC<br>ACCTTGGAGATCTTCACGCCAGCGAGAGTTTTCCGACGGG<br>CTGCCGGCTTCCTGGGTGGTGTTGAAGCAGGGGAAGGAG<br>GGAGATCCGGGGCAGACATCAAGAGCGCAGGCTGGCGA<br>GCACAGAACAGTGGTTCCGGGAGAGCCACCCCCAGGCTT<br>GGCACAAGCAGCTCAGCAAGCCCCGCCGGCAACACGTCA<br>TCATCTGCACGTTTACGAGCCGTGGAGATGTCGGGGTTC<br>GCTGCAGGGGCCACTGCTGAGGACGGGTGGTGTAGGAG<br>ATGCCTCAAAGCCGGGAGGCGTACTGGCGAGACGTGGA<br>GGAGGGGGCTCAACATGGAGACCGCGAGCAAAGCTCA<br>ATGAGTGCTGGACTCCTCTCTTGAATGGCCTCTGTAGCAA<br>CCCTAGCCTCATCACGCTTGGAGGGGGGTGGTGAGCGGA<br>GCACGGACTTGGGGGAGAGGGGCGGCGAAGCCGGAGGA<br>GTGCGGGCGTCCCTTGAGTCCCGCCTGGCACTGCCTGGGC<br>GCGCGTGCCTATACGGGCTGCGACCACGAGCCTCCACCG<br>GAGCAGCCAGAGCGGTGGCCGGAGGGGCTCGACCCATCT<br>CCAGGGCGCAAGCCTCGGGGTCGCAGACTGCGCCGGAGC<br>CGAAGAGGAGAGGGGCGGCGCCGGAGCCCAAGAGGACA |

| SEQ ID NO | Name | Sequence | Length |
|---|---|---|---|
| | | GGGGCGGCGGCCGGCGGGGGCGGCGGCGATGCAGCGCG<br>CCTGCGGCCGTCGCGGTTGCCGCGATGGTCATCCCTGCTT<br>CCCCTGTCTTGGTCATGCCGCTGATCGTCGCGTGGCGCAC<br>GGGAAAGGCTCCTGTGGACACGTGCACCGCTGTCTTGAC<br>CTCCCCTGGACGCGTCGCGCCCGTCGCGGCCACGACCGC<br>GGTCACCATCTTCATCTCGATCGCGCCGATCCTGACGCAC<br>GGGACAAGAGACGCGCTCACGCCTGTCGCGAGCTTTGGC<br>CTCGCCATCCACGATGTTGTAGCGCCACGTCTCGGTCGGC<br>GGACTATTCACACAACCGATGCGTCGCCGCTCTCGGCCCG<br>CGTGCATGTATGGCGCGCCCCGCCGCTCGCGGACGCGTA<br>CGTTTGGCCGCCAAATCCACCGGACGCAAAGATATATCCT<br>CGTCGTAGCGACGGAAGGACGCTTGCATGTATGGATGGA<br>GAAGCCGGTGAAACAAAAGGGAAAACAAGATGGACGCC<br>GCCGTCTCGCCAATCTCGCCCACCCACACTAGATCCCGGC<br>GCTCCATGGAGACTTGGGGAAGACACGTCCCCCAACTCT<br>ATAATGCCGCCTCCAGCGCCGCCGTGGAGGAACCGGAGT<br>TGCGGAAGATGTATTGGACACTAGTGCGCGGCCACCACC<br>CGGACGAAGCCAAACGAAAACCTAACCCTACAGCTATCT<br>ACAAACGGAATGCATGCACCACTCGGCCAACTATTCACA<br>CGACCAACGCGTCGCCGCTCTCGGTCCGCATGTATGTATG<br>GCGCGCCCCGCCGGTCGCCGACGCGTACGTTTGACCGCC<br>AAATGCACCGGACGCAAAAATATGTCCTCGTCGCAGCGA<br>CGTGCGCGGATGCCCCATCCCTGGAGCTGGACCGCGCCA<br>TGCGAAAGACGAGCCGGGCGCGTCGCCGTCCGGCGCTGC<br>GGGTAGTCCGATCCGATCGAGCCAGCCGCTACGCGCCGG<br>CGCCGCTTGCAGCAGAAAAGGACGGGGCGATGGATCCAT<br>CGCAACAAGCGCGGGCAGGCGCCACGCCATCCACGTAAC<br>AGCCAGGCCAAGAAAACTCGTGTACGAAGCTCCGTGCTC<br>AGCGCTGGGCACGCGCGCGCTCTCGCCGCACCCCCACCC<br>CCTATAAATTGGCCGGCCCGCGCTGCGACCTCCTCACACG<br>CTTTCCCTCACACAACACACACCCATCTCCTTCCGCACAG<br>CTCTCCACCGAAAGGCACTGGTAGTGCAGTTGAAGTAGC<br>GACGGTACTGAAATAGCAGCAAGATGATACTGGGCGGGC<br>TCATCGACAGCCTGACCGGCGCGAACAAGAACGCACGTC<br>TCAAGGGCACGGCGGTGCTGATGAGGAAGAACGTGCTGG<br>ACCTCACCGACTTCGGCGCCACCATCATGGACGGCATCG<br>GCGACTTCCTCGGCAAGGGCGTCACCTGCCAGCTTATCAG<br>CTCCACCCTCATCGACCACG | |

What is claimed is:

1. A wheat plant comprising at least one mutation in an Lpx1 gene in at least one of a B or D genome, wherein the Lpx1 gene of the B genome is Lpx-B1.2, and the at least one mutation in the Lpx-B1.2 gene comprises a tryptophan substitution to a stop codon at amino acid position 510 (W510*) of SEQ ID No. 6, or a tryptophan substation to a stop codon at amino acid position 494 (W494*) of SEQ ID No. 6, or a guanine substitution to an adenine at nucleotide position 2691 of SEQ ID No. 4, and further wherein the Lpx1 gene of the D genome is Lpx-D1, and at least one mutation in the Lpx-D1 gene comprises a tryptophan substitution to a stop codon at amino acid position 494 (W494*) of SEQ ID No. 3, or a tryptophan substitution to a stop codon at amino acid position 81 (W81*) of SEQ ID No. 3, or a tryptophan substitution to a stop codon at amino acid position 101 (W101*) of SEQ ID No. 3, or a tryptophan substitution to a stop codon at amino acid position 517 (W517*) of SEQ ID No. 3, or a guanine substitution to an adenine at nucleotide position 1538 of SEQ ID No. 15.

2. The wheat plant of claim 1 comprising at least one mutation in the B genome of the Lpx-B1.2 gene, wherein the at least one mutation in the Lpx-B1.2 gene comprises a tryptophan substitution to a stop codon at amino acid position 510 (W510*) of SEQ ID No. 6.

3. Wheat grain from the wheat plant of claim 2.

4. Flour comprising wheat grain of claim 3.

5. The wheat plant of claim 1 comprising at least one mutation in the D genome of the Lpx-D1 gene, wherein the at least one mutation in the Lpx-D1 gene comprises a tryptophan to a stop codon at amino acid position 494 (W494*) of SEQ ID No. 3.

6. Wheat grain from the wheat plant of claim 5.

7. Flour comprising wheat grain of claim 6.

8. Wheat grain from the wheat plant of claim 1.

9. Flour comprising wheat grain of claim 8.

10. A wheat seed, plant part or progeny thereof from a wheat plant of claim 1, wherein said progeny comprises the Lpx1 mutation or mutations.

11. The wheat plant of claim 1, wherein milled grain from said wheat plant has a property selected from the group consisting of: (a) increased shelf-life; (b) increased oxidative stability; (c) decreased production of Lpx1 protein; (d)

decreased activity of the Lpx1 protein; (e) decreased hexanal production; (f) decreased pinellic acid production; (g) decreased decomposition products from fatty acids; or (h) improved sensory characteristics as compared to milled grain from a wild type wheat plant.

12. A wheat plant comprising at least one mutation in an Lpx1 gene in each of a B and a D genome, wherein the Lpx1 gene of the B genome is Lpx-B1.2, and the at least one mutation in the Lpx-B1.2 gene comprises a tryptophan substitution to a stop codon at amino acid position 510 (W510*) of SEQ ID No. 6, or a tryptophan substitution to a stop codon at amino acid position 494 (W494*) of SEQ ID No. 6, or a guanine substitution to an adenine at nucleotide position 2691 of SEQ ID No. 4, and further wherein the Lpx1 gene of the D genome is Lpx-D1, and the at least one mutation in the Lpx-D1 gene comprises a tryptophan substitution to a stop codon at amino acid position 494 (W494*) of SEQ ID No. 3, or a tryptophan substitution to a stop codon at amino acid position 81 (W81*) of SEQ ID No. 3, or a tryptophan substitution to a stop codon at amino acid position 101 (W101*) of SEQ ID No. 3, or a tryptophan substitution to a stop codon at amino acid position 517 (W517*) of SEQ ID No. 3, or a guanine substitution to an adenine at nucleotide position 1538 of SEQ ID No. 15.

13. The wheat plant of claim 12, wherein the at least one mutation in the B genome of the Lpx-B1.2 gene comprises a tryptophan substitution to a stop codon at amino acid position 510 (W510*) of SEQ ID No. 6.

14. The wheat plant of claim 12, wherein the at least one mutation in the D genome of the Lpx-D1 gene comprises a tryptophan substitution to a stop codon at amino acid position 494 (W494*) of SEQ ID No. 3.

15. Wheat grain from the wheat plant of claim 12.

16. Flour comprising wheat grain of claim 15.

17. A wheat seed, plant part or progeny thereof from a wheat plant of claim 12, wherein said progeny comprises the Lpx1 mutations.

18. The wheat plant of claim 12, wherein the at least one mutation in the B genome of the Lpx-B1.2 gene comprises a tryptophan substitution to a stop codon at amino acid position 510 (W510*) of SEQ ID No. 6 and the at least one mutation in the D genome of the Lpx-D1 gene comprises a tryptophan substitution to a stop codon at amino acid position 494 (W494*) of SEQ ID No. 3.

19. The wheat plant of claim 18, wherein milled grain from said wheat plant has a property selected from the group consisting of: (a) increased shelf-life; (b) increased oxidative stability; (c) decreased production of Lpx1 protein; (d) decreased activity of the Lpx1 protein; (e) decreased hexanal production; (f) decreased pinellic acid production; (g) decreased decomposition products from fatty acids; or (h) improved sensory characteristics as compared to milled grain from a wild type wheat plant.

20. Wheat grain from the wheat plant of claim 18.

21. Flour comprising wheat grain of claim 20.

22. A wheat seed, plant part or progeny thereof from a wheat plant of claim 18, wherein said progeny comprises the Lpx1 mutations.

23. The wheat plant of claim 12, wherein milled grain from said wheat plant has a property selected from the group consisting of: (a) increased shelf-life; (b) increased oxidative stability; (c) decreased production of Lpx1 protein; (d) decreased activity of the Lpx1 protein; (e) decreased hexanal production; (f) decreased pinellic acid production; (g) decreased decomposition products from fatty acids; or (h) improved sensory characteristics as compared to milled grain from a wild type wheat plant.

* * * * *